(12) United States Patent
Pulé et al.

(10) Patent No.: US 11,701,386 B2
(45) Date of Patent: Jul. 18, 2023

(54) CELL

(71) Applicant: AUTOLUS LIMITED, London (GB)

(72) Inventors: Martin Pulé, London (GB); Shaun Cordoba, London (GB); Simon Thomas, London (GB); Shimobi Onuoha, London (GB); Matteo Righi, London (GB)

(73) Assignee: AUTOLUS LIMITED, London (GB)

( * ) Notice: Subject to any disclaimer, the term of this patent is extended or adjusted under 35 U.S.C. 154(b) by 289 days.

(21) Appl. No.: 16/646,906

(22) PCT Filed: Sep. 12, 2018

(86) PCT No.: PCT/GB2018/052583
§ 371 (c)(1),
(2) Date: Mar. 12, 2020

(87) PCT Pub. No.: WO2019/053420
PCT Pub. Date: Mar. 21, 2019

(65) Prior Publication Data
US 2020/0297766 A1    Sep. 24, 2020

(30) Foreign Application Priority Data
Sep. 13, 2017 (GB) .................................. 1714718

(51) Int. Cl.
| C12N 15/62 | (2006.01) |
| A61K 35/17 | (2015.01) |
| C07K 14/47 | (2006.01) |
| C07K 14/705 | (2006.01) |

(52) U.S. Cl.
CPC .......... *A61K 35/17* (2013.01); *C07K 14/4705* (2013.01); *C07K 14/705* (2013.01); *C12N 15/62* (2013.01); *C07K 2319/02* (2013.01); *C07K 2319/20* (2013.01); *C07K 2319/50* (2013.01); *C07K 2319/70* (2013.01)

(58) Field of Classification Search
CPC .......... C12N 15/61; C12N 15/62; A61K 35/17
See application file for complete search history.

(56) References Cited

U.S. PATENT DOCUMENTS

| 2022/0025001 A1* | 1/2022 | Sentman ................. A61P 35/00 |
| 2022/0145325 A1 | 5/2022 | Pulé et al. |
| 2022/0364116 A1 | 11/2022 | Pulé et al. |

FOREIGN PATENT DOCUMENTS

| WO | WO-01/09326 A1 | 2/2001 |
| WO | WO-2015/150771 A1 | 10/2015 |
| WO | WO-2017/029512 A1 | 2/2017 |
| WO | WO-2017/190100 A1 | 11/2017 |
| WO | WO-2017/218850 A1 | 12/2017 |
| WO | WO-2020/183131 A1 | 9/2020 |

OTHER PUBLICATIONS

Ding et al., "IL-7 signaling imparts polyfunctionality and sternness potential to CD4+ T cells," Oncoimmunology 5(6):e1171446, 13 pages (2016).
Hassuneh et al., "Evidence for the Participation of Interleukin-2 (IL-2) and IL-4 in the Regulation of Autonomous Growth and Tumorigenesis of Transofmred Cells of Lymphoid Origin," Blood 89:610-620 (1997).
Hurton et al., "Tethered IL-15 augments antitimor activity and promotes a stem-cell memory subset in tumor-specific T cells," PNAS 113(48):E7788-E7797 (2016).
International Search Report and Written Opinion from International Application No. PCT/GB2018/052583 dated Nov. 23, 2018.
Kagoya et al., "A novel chimeric antigen receptor containing a JAK-STAT signaling domain mediates superior antitumor effects," Nat Med 24(3):352-359 (2018).
Milner et al., "Early-onset lymphoproliferation and autoimmunity caused by germline STAT3 gain-of-function mutations," Blood 125:591-599 (2015).
Nagarkatti et al., "Constitutive activation of the interleukin 2 gene in the induction of spontaneous in vitro transformation and tumorigenicity of T cells," Proc. Natl. Acad. Sci. 91:7638-7642 (1994).
Onishi et al., "Identification and Characterization of a Constitutively Active STAT5 Mutant That Promotes Cell Proliferation," Molecular and Cellular Biology 18(7):3871-3879 (1998).
Vogtenhuber et al., "Constitutively active Stat5b in CD4+ T cells inhibits graft-versus-host disease lethality associated with increased regulatory T-cell potency and decreased T effector cell responses," Blook 116(3):466-474 (2010).
Baker et al., "Hematopoietic cytokine receptor signaling," Oncogene 26:6724-6737 (2007).
Burchill et al., "Distinct Effects of STAT5 Activation on CD4+ and CD8+ T Cell Homeostasis: Development of CD4+ CD25+ Regulatory T Cells versus CD8+ Memory T Cells", The Journal of Immunology, 171(11):5853-5864 (2003).

\* cited by examiner

*Primary Examiner* — Maryam Monshipouri
(74) *Attorney, Agent, or Firm* — Marshall, Gerstein & Borun LLP

(57) ABSTRACT

The present invention relates to a cell comprising a chimeric antigen receptor (CAR) and a constitutively active or inducible Signal Transducer and Activator of Transcription (STAT) molecule.

7 Claims, 18 Drawing Sheets

Specification includes a Sequence Listing.

Figure 7

SEQ ID NO: 7 (STAT3 – Linker – STAT5)

STAT3: MAQWNQLQQLDTRYLEQLHQLYSDSFPMELRQFLAPWIESQDWAYAASKESHATLVFHNLLGEIDQQYSRFLQESNVLYQHNLRRIKQFL
QSRYLEKPMEIARIVARCLWEESRLLQTAATAAQQGGQANHPTAAVTEKQQMLEQHLQDVRKRVQDLEQKMKVVENLQDFDFNYKTLKSQGDMQ
DLNGNNQSVTRQKMQQLEQMLTALDQMRRSIVSELAGLLSAMEYVQKTLTDEELADWKRRQQIACIGGPPNICLDRLENWITSLAESLQTRQQIK
KLEELQQKVSYKGDPIVQHRPMLEERIVELFRNLMKSAFVVERQPCMPMHPDRPLVIKTGVQFTTKVRLLVKFPELNYQLKIKVCIDKDSGDVAAL
RGSRKFNILGTNTKVMNMEESNNGSLSAEFKHLTLREQRCGNGGRANCDASLIVTEELHLITFETEVYHQGLKIDLETHSLPVVVISNICQMPNAW
ASILWYNMLTNNPKNVNFFTKPPIGTWDQVAEVLSWQFSSTTKRGLSIEQLTTLAEKLLGPGVNYSGCQITWAKFCKENMAGKGFSFWWLDNIID
LVKKYILALWNEGYIMGFISKERERAILSTKPPGTFLLRFSESSKEGGVTFTWVEKDISGKTQIQSVEPYTKQQLNNMSFAEIMGYKIMDATNIL
VSPLVYLYPDIPKEEAFGKYCRPESQEHPEADPGSAAPYLKTKFICVTPTTCSNTIDLPMSPRTLDSLMQFGNNGEGAEPSAGGQFESLTFDMELT
SECATSPM

Linker: SGGGGSGGGGSGGGGSGGGGSGGGGSGGGGS

STAT5: MAGWIQAQQLQGDALRQMVLYGQHFPIEVRHYLAQWIESQPWDAIDLDNPQDRAQATQLLEGLVQELQKKAEHQVGEDGFLLKIKLGHY
ATQLQKTYDRCPLELVRCIRHILYNEQRLVREANNCSSPAGILVDAMSQKHLQINQTFEELRLVTQDTENELKKLQQTQEYFIIQYQESLRIQAQF
AQLAQLSPQERLSRETALQQKQVSLEAWLQREAQTLQQYRVELAEKHQKTLQLLRKQQTIILDDELIQWKRRQQLAGNGGPPEGSLDVLQSWCEKL
AEIIWQNRQQIRRAEHLCQQLPIPGPVEEMLAEVNATITDIISALVTSTFIIEKQPPQVLKTQTKFAATVRLLVGGKLNVHMNPPQVKATIISEQQ
AKSLLKNENTRNECSGEILNNCCVMEYHQATGTLSAHFRNMSLKRIKRADRRGAESVTEEKFTVLFESQFSVGSNELVFQVKTLSLPVVIVHGSQ
DHNATATVLWDNAFAEPGRVPFAVPDKVLWPQLCEALNMKFKAEVQSNRGLTKENLVFLAQKLFNNSSSHLEDYSGLSVSWSQFNRENLPGWNYTF
WQWFDGVMEVLKKHHKPHWNDGAILGFVNKQQAHDLLINKPDGTFLLRFSDSEIGGITIAWKFDSPERNLWNLKPFTTRDFSIRSLADRLGDLSYL
IYVFPDRPKDEVFSKYTPVLAKAVDGYVKPQIKQVVPEFVNASADAGGSSATYMDQAPSPAVCPQAPYNMYPQNPDHVLDQDGEFDLDETMDVAR
HVEELLRRPMDSLDSRLSPPAGLFTSARGSLS

Figure 8

SEQ ID NO: 8 (TIP – STAT3 – Linker – STAT5 – 2a – Myristoylation and palmitoylation sequence – Ridge Linker – TetRB)

TIP:MWTWNAYAFAAP
Linker:SGGGS
STAT3:AQWNQLQQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQQGQANHPTAAVTEKQQMLEQHLQDVRKRVQDLEQMKVVENLQDDFENYKTLKSQGDMQDLNGNNQSVTRQKMQQLEQ
MLTALDQMRRSIVSELAGLLSAMEYVQKTLTDEELADWKRRQIACIGGPPNICLDRLENWITSLAESQLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKFNILGTNTKVMNEESNNGLSAEFKHLTLRE
QRCGNGGRANCDASLIVTEELHLITFETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWVWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNILVSPLVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM Linker:
SGGGSSGGGGSGGGGSGGGGSGGGGS STAT5:
MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYDRCPLEL
VRCIRHILYNEQRLVREAANNCSSPAGILVDAMSQKHLQINQTFEELRLVTQDTENELKKLQQTQEYFIIQYQESLRIQAQFAQLAQLSPQERLSRETALQQKQVS
LEAWLQREAQTLQQYRVELAEKHQKTLQLLRKQQTIILDDELIQWKRRQQLAGNGGPPEGSLDVLQSWCEKLAEIIWQNRQQIRRAEHLCQQLPIPGPVEEMLAE
VNATITDIISALVTSTFIIEKQPPQVLKTQTKFAATVRLLVGGKLNVHMNPPQVKATIISEQQAKSLLKNENTRNECSGEILNNCCVMEYHQATGTLSAHFRNMS
LKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEVQSNRGL
TKENLVFLAQKLFNNSSSHLEDYSGLSVSWSQFNRENLPGWNYTFWQWFDGVMEVLKKHHKPHWNDGAILGFVNKQQAHDLLINKPDGTFLLRFSDSEIGGITIA
WKFDSPERNIWNLKPFTTRDFSIRSLADRLGDLSYLIYVFPDRPKDEVFSKYYTPVLAKAVDGYVKPQIKQVVPEFVNASADAGGSSATYMDQAPSPAVCPQAPY
NMYPQNPDHVLDQDGEFDLDETMDVARHVEELLRRPMDSLDSRLSPPAGLFTSARGSLS

2A:EGRGSLLTCGDVEENPGP

Myristoylation and Palmitoylation sequence (10aa_Lck):MGCGCSSHPE

Ridge linker:LEAEAAAKEAAAKEAAAKEAAAKEAAAKALEAEAAAKEAAAKEAAAKEAAAKALESGGGS

TetRb:MSRLDKSKVINSALELLNEVGIEGLTTRKLAQKLGVEQPTLYWHVKNKRALLDALAIEMLDRHHTHFCPLEGESWQDFLRNNAKSFRCALLSHRDGAKV
HLGTRPTEKQYETLENQLAFLCQQGFSLENALYALSAVGHFTLGCVLEDQEHQVAKEERETPTTDSMPPLLRQAIELFDHQGAEPAFLFGLELIICGLEKQLKCE
SGS

Figure 9

SEQ ID NO: 9 (SH2 ZAP70 – Linker – TEV – 2a - Myristoylation and palmitoylation sequence – linker – TEV cleavage site – STAT3 – Linker – STAT5 – 2a – aCD19)

DZap70SH2domains:MPDPAAHLPFFYGSISRAEAEEHLKLAGMADGLFLLRQCLRSLGGYVLSLVHDVRFHHFPIERQLNGTYAIAGGKAHCGPAELCEFYS
RDPDGLPCNLRKPCNRPSGLEPQPGVFDCLRDAMVRDYVRQTWKLEGEALEQAIISQAPQVEKLIATTAHERMPWYHSSLTREEAERKLYSGAQTDGKFLLRPRK
EQGTYALSLIYGKTVYHYLISQDKAGKYCIPEGTKFDTLWQLVEYLKLKADGLIYCLKEACPNSSASNASGAAAPTLPAHPSTLTHP Linker: SGGGGS TEV:SLFKGPRDYNPISSTICHLTNESDGHTTSLYGIGFGPFIITNKHLFRRNNGTLLVQSLHGVFKVKNTTTLQQHLIDGRDMIIRMPKDFPFPQKLKFREP
QREERICLVTTNFQTKSMSSMVSDTSCTFPSSDGIFWKHWIQTKDGQCGSPLVSTRDGFIVGIHSASNFTNTNNYFTSVPKNFMELLTNQEAQQWVSGWRLNADS
VLWGGHKVFMSKPEEFQPVKEATQLMNELVYSQ

2A: EGRGSLLTCGDVEENPGP

Myristoylation and Palmitoylation sequence (10aa_Lck): MGCGCSSHPE

Linker: SGGGSGGGGS

TEV cleavage site x3: ENLYFQGENLYFQGENLYFQG

STAT3:AQWNQLQQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQQGQANHPTAAVTEKQQMLEQHLQDVRKRVQDLEQKMKVVENLQDDFDENYKTLKSQGDMQDLNGNNQSVTRQKMQQLEQ
MLTALDQMRRSIVSELAGLLSAMEYVQKTLTDEELADWKRRQQIACIGGPPNICLDRLENWITSLAESLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKFNILGTNTKVMNMEESNNGSLSAEFKHLTLRE
QRCGNGGRANCDASLIVTEELHLITETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWVWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNILVSPLIVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM

Linker: SGGGGSGGGGSGGGGSGGGGSGGGGS

STAT5:MAGWIQAQQLGDALRQMQVLYGQHFPIEVRHYLAQWIESQPWDAIDLDNPQDRAQATQLLEGLVQELQKKAEHQVGEDGFLLKIKLGHYATQLQKTYD
RCPLEIVRCIRHILYNEQRLVREANNCSSPAGIIVDAMSQKHLQINQTFEELRLVTQDTENELKKLQQTQEYFIIQYQESLRIQAQFAQLAQLSPQERLSRETAL
QKQVSLEAWLQREAQTLQQYRVELAEKHQKTLQLLRKQQTIILDDELIQWKRRQQLAGNGGPPEGSLDVLQSWCEKLAEIIWQNRQQIRRAEHLCQQLPIPGPV
EEMLAEVNATITDIISALVTSTFIIEKQPPQVLKTQTKFAATVRLLVGGKLNVHMNPPQVKATIISEQQAKSLLKNENTRNECSGEILNNCCVMEYHQATGTLSA
HFRNMSLKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEV
QSNRGLTKENLVFLAQKLFNNSSSHLEDYSGLSVSWSQFNRENLPGWNYTFWQWFDGVMEVLKKHHKPHWNDGAILGFVNKQQAHDLLINKPDGTFLLRFSDSEI
GGITIAWKFDSPERNLWNLKPFTTRDFSIRSLADRLGDLSYLIYVFPDRPKDEVFSKYYTPVLAKAVDGYVKPQIKQVVPEFVNASADAGGSSATYMDQAPSPAV
CPQAPYNMYPQNPDHVLDQDGEFDLDETMDVARHVEELLRRPMDSLDSRLSPPAGLFTSARGSLS

Linker: EGRGSLLTCGDVEENPGP aCD19CAR:METDTLLLWVLLLWVPGSTGDIQMTQTTSSLSASLGDRVTISCRASQDISKYLNWYQQKPDGTVKLLIYHTSRLHSGVPSRFSGSGSGTDYSLTIS
NLEQEDIATYFCQQGNTLPYTFGGGTKLEITKAGGGGSGGGGSGGGGSEVKLQESGPGLVAPSQSLSVTCTVSGVSLPDYGVSWIRQPPRKGLEWLGVIW
GSETTYNSALKSRLTIIKDNSKSQVFLKMNSLQTDDTAIYYCAKHYYYGGSYAMDYWGQGTSVTVSSDPTTTPAPRPPTPAPTIASQPLSLRPEACRPAAGGAV
HTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGERRRGKGHDGLYQGLSTATKDTYDALHMQALPPR

Figure 10

SEQ ID NO: 10 (TIP - Linker - dZap70SH2 - linker - TEV - 2a - Truncated CD22 - CD19TM - Tyro-1 endodomain - Linker - TetRB - 2A - aCD19 - linker - TEV cleavage site x 3 - GOFSTAT5(S710F))

TIP: MWTWNAYAFAAP
Linker: SGGGS
dZap70SH2domains: MPDPAAHLPFFYGSISRAEAEEHLKLAGMADGLFLLRQCLRSLGGYVLSLVHDVRFHHFPIERQLNGTYAIAGGKAHCGPAELCEFYSRDPDGLPCNLR
KPCNRPSGLEPQPGVFDCLRDAMVRDYVVRQTWKLEGEALEQAIISQAPQVEKLIATTAHERMPWYHSSLTREEAERKLYSGAQTDGKFLLRPRKEQGTYALSLIYGKTVYHYLISQ
DKAGKYCIPEGTKFDTLWQLVEYLKLKADGLIYCLKEACPNSSASNASGAAAPTLPAHPSTLTHP
Linker: SGGGGS
TEV: SLFKGPRDYNPISSTICHLTNESDGHTTSLYGIGFGPFIITNKHLFRRNNGTLLVQSLHGVFKVKNTTLQQHLIDGRDMIIIRMPKDFPFPQKLKFREPQREERICLVTT
NFQTKSMSSMVSDTSCTFPSSDGIFWKHWIQTKDGQCGSPLVSTRDGFIVGIHSASNFTNTNNYFTSVPKNFMELLTNQEAQOWVSGWRLNADSVLWGGHKVFMSKPEEFFQPVKE
ATQLMNELVYSQ
2A: EGRGSLLTCGDVEENPGP
TruncatedCD22: METDTLLLWVLLLWVPGSTGDSSGKPIPNPLLGLDSSGGGSAPRDVRVRKIKPLSEIHSGNSVSLQCDFSSSHPKEVQFFWEKNGRLLGKESQLNFDSISPE
DAGSYSCWVNNSIGQTASKAWTLEVLYAPRRLRVSMSPGDQVMEGKSATLTCESDANPPVSHYTWFDWNNQSLPYHSQKLRLEPVKVQHSGAYWCQGTNSVGKGRSPLSTLTVYYS
PETIGRR
CD19TM: AVTLAYLIFCLCSLVGILHL
Tyrp-1 endodomain: RARRSMDEANQPLLTDQYQCYAEEYEKLQNPNQSVV
Linker: GGSGGS
TETRb: MSRLDKSKVINSALELLNEVGIEGLITTRKLAQKLGVEQPTLYWHVKNKRALLDALAIEMLDRHHTHFCPLEGESWQDFLRNNAKSFRCALLSHRDGAKVHLGTRPTEKQY
ETLENQLAFLCQQGFSLENALYALSAVGHFTLGCVLEDQEHQVAKEERETPTTDSMPPLLRQAIELFDHQGAEPAFLFGLELIICGLEKQLKCESGS
2A: EGRGSLLTCGDVEENPGP
aCD19CAR: METDTLLLWVLLLWVPGSTGDIQMTQTTSSLSASLGDRVTISCRASQDISKYLNWYQQKPDGTVKLLIYHTSRLHSGVPSRFSGSGSGTDYSLTISNLEQEDIATYF
CQQGNTLPYTFGGGTKLEITKAGGGSGGGGSGGGGSSEVKLQESGPGLVAPSQSLSVTCTVSGVSLPDYGVSWIRQPPRKGLEWLGVIWGSETTYNSALKSRLTIIKDNS
KSQVFLKMNSLQTDDTAIYYCAKHYYYGGSYAMDYWGQGTSVTVSSDPTTTPAPRPPTPAPTIASQPLSLRPEACRPAAGGAV
HTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKDTYDALHMQALPPR
Linker: GGSGGS
TEV cleavage site x3: ENLYFQGENLYFQGENLYFQG
GOF_STAT5(S710F): MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYD
RCPLELVRCIRHILYNEQRLVREANNCSSPAGILVDAMSQKHLQINQTFEELRLVTQDTENELKKLQQTQEYFIIQYQESLRIQAFAQLAQLSPQERLSRETALQQKQVSLEAWL
QREAQTLQQYRVELAEKHQKTLQLLRKQQTIILDDELIQWKRRQQLAGNGGPPEGSLDVLQSWCEKLAEIIWQNRQQIRRAEHLCQQLPIPGPVEEMLAEVNATITDIISALVTST
FIIEKQPPQVLKTQTKFAATVRLLVGGKLNVHMNPPQVKATIISEQQAKSLLKNENTRNECSGEILNNCCVMEYHQATGTLSAHFRNMSLKRIKRADRRGAESVTEEKFTVLFESQ
FSVGSNELVFQVKTLSLPVVVIVHGSQDHNATATVLWDNAFAEPGRVFEAVPDKVLWPQLCEALNMKFKAEVQSNRGLTKENLVFLAQKLFNSSSHLEDYSGLSVSWSQFNRENL
PGWNYTFWQWFDGVMEVLKKHHKPHWNDGAILGFVNKQQAHDLLINKPDGTFLLRFSDSEIGGITIAWKFDSPERNLWNLKPFTTRDFSIRSLADRLGDLSYLIYVFPDRPKDEVF
SKYYTPVLAKAVDGYVKPQIKQVVPEFVNAFADAGGSSATYMDQAPSPAVCPQAPYNMYPQNPDHVLDQDGEFDLDETMDVARHVEELLRRPMDSLDSRLSPPAGLFTSARGSLS

Figure 11

SEQ ID NO: 11 (FRB – linker - STAT5 - 2a – FKBP12 – linker - STAT3)

FRB: ILWHEMWHEGLEEEASRLYFGERNVKGMFEVLEPLHAMMERGPQTLKETSFNQAYGRDLMEAQEWCRKYMKSGNVKDLLQAWDLYYHVFRRISK
Linker: SGGGGSGGGGSGGGGS
STAT5: MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYD
RCPLELVRCIRHILYNEQRLVREANNCSSPAGILVDAMSQKHLQINQTFEELRLVTQDTENELKKLQQTQEYFIIQYQESLRIQAFAQLAQLSPQERLSRETAL
QQKQVSLEAMLQREAQTLQQYRVELAEKHQKTLQLLRKQQTIILDDELIQWKRRQQLAGNGGPPEGSLDVLQSWCEKLAEIWQNRQQIRRAEHLCQQLPIPGPV
EEMLAEVNATITDIISALVTSTFIIEKQPPQVLKTQTKFAATVRLLVGGKLNVHMNPPQVKATIISEQQAKSLLKNENTRNECSGEILNNCCVMEYHQATGTLSA
HFRNMSLKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEV
QSNRGLTKENLVFLAQKLFNNSSSHLEDYSGLSVSWSQFNRENLPGWNYTFWQWFDGVMEVLKKHHKPHWNDGAILGFVNKQQAHDLLINKPDGTFLLRFSDSEI
GGITIAWKFDSPERNLWNLKPFTTRDFSIRSLADRLGDLSYLIYVFPDRPKDEVFSKYYTPVLAKAVDGYVKPQIKQVVPEFVNASADAGGSSATYMDQAPSPAV
CPQAPYNMYPQNPDHVLDQDGEFDLDETMDVARHVEELLRRPMDSLDSRLSPPAGLFTSARGSLS
2A: EGRGSLLTCGDVEENPGP
FKBP12: GVQVETISPGDGRTFPKRGQTCVVHYTGMLEDGKKVDSSRDRNKPFKFMLGKQEVIRGWEEGVAQMSVGQRAKLTISPDYAYGATGHPGIIPPHATLV
FDVELLKLE
Linker: SGGGGSGGGGSGGGGS
STAT3: AQWNQLQQLQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQQGQANHPTAAVTEKQQMLEQHLQDVRKRVQDLEQKMKVVENLQDDFDFNYKTLKSQGDMQDLNGNNQSVTRQKMQQLEQ
MLTALDQMRRSIVSELAGLLSAMEYVQKTLTDEELADWKRRQQIACIGGPPNICLDRLENWITSLAESLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKFNILGTNTKVMNMEESNNGSLSAEFKHLTLRE
QRCGNGGRANCDASLIVTEELHLITFETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNILVSPLVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM

Figure 12

SEQ ID NO: 12 (TIP – linker - STAT5 – 2a – TetRB – linker - STAT3)

TIP: MWTWNAYAFAAP
Linker: SGGGGSGGGGSGGGGS
STAT5: MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYD
RCPLELVRCIRHILYNEQRLVREANNCSSPAGILVDAMSQKHLQINQTFEELRLVTQDTENELKKLQOTQEYFIIQYQESLRIQAQFAQLAQLSPQERLSRETAL
QQKQVSLEAWLQREAQTLQQYRVELAEKHQKTLQLLRKQQTIILDDELIQWKRRQQLAGNGPPEGSLDVLQSWCEKLAEIWQNRQQIRRAEHLCQQLPIPGPV
EEMLAEVNATITDIISALVTSTFTIEKQPPQVLKTQTKFAATVRLLVGGKLNVHMNPPQVKATIISEQQAKSLLKNENTRNECSGEILNNCCVMEYHQATGTLSA
HFRNMSLKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEV
QSNRGLTKENLVFLAQKLFNNSSSHLEDYSGLSVSWSQFNRENLPGWNYTFWQMFDGVMEVLKKHHKPHWNDGAILGFVNKQQAHDLLINKPDGTFLLRFSDSEI
GGITIAWKFDSPERNLWNLKPFTTRDFSIRSLADRLGDLSYLIYVFPDRPKDEVFSKYYTPVLAKAVDGYVKPQIKQVVPEFVNASADAGGSSATYMDQAPSPAV
CPQAPYNMYPQNPDHVLDQDGEFDLDETMDVARHVEELLRRPMDSLDSRLSPPAGLFTSARGSLS
2A: EGRGSLLTCGDVEENPGP
TetRB: MSRLDKSKVINSALELLNEVGIEGLTTRKLAQKLGVEQPTLYWHVKNKRALLDALAIEMLDRHTHFCPLEGESWQDFLRNNAKSFRCALLSHRDGAKV
HLGTRPTEKQYETLENQLAFLCQQGFSLENALYALSAVGHFTLGCVLEDQEHQVAKEERETPTTDSMPPLLRQAIELFDHQGAEPAFLFGLELIICGLEKQLKCE
SGS
Linker: SGGGGSGGGGSGGGGS
STAT3: AQWNQLQQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQQGQANHPTAAVTEKQQMLEQHLQDVRKRVQDLEQKMKVVENLQDDFDFNYKTLKSQGDMQDLNGNNQSVTRQKMQQLEQ
MLTALDQMRRSIVSELAGLLSAMEYVQKTLTDEELADWKRRQQIACIGGPPNICLDRLENWITSLAESLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKFNILGTNTKVMNMEESNNGSLSAEFKHLTLRE
QRCGNGGRANCDASLIVTEELHLITEEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNIILVSPLVLYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM (a)

CELL

CROSS-REFERENCE TO RELATED APPLICATIONS

This is a U.S. National Phase of International Application No. PCT/GB2018/052583, filed Sep. 17, 2018, which claims priority to Great Britain Application No. 1714718.2, filed Sep. 13, 2017.

FIELD OF THE INVENTION

The present invention relates to a cell comprising a chimeric antigen receptor (CAR) and a constitutively active or inducible Signal Transducer and Activator of Transcription (STAT) molecule.

BACKGROUND TO THE INVENTION

Chimeric Antigen Receptors (Cars)

A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1).

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Car T Cell Engraftment and Proliferation

Function of CAR T cells depends on engraftment within the patients. In some settings, like ALL, engraftment of up to 9 months appears important to prevent relapse and effect sustained remissions. Present strategies to increase CAR T cell engraftment include generation of CAR T-cell product to result in naïve and central-memory T-cells, selection of co-stimulatory signals and/or co-administration of the CAR T cells with prolonged therapies (e.g., kinase inhibitors such as Ibrutinib). CAR T-cell persistence and activity can also be enhanced by administration of cytokines or by the CAR T-cells producing cytokines constitutively and by generating a CAR T cell product to result in a selection of co-stimulatory signals.

However, the above approaches have limitations. For example, prolonged exposure to chemotherapy may have undesirable short term and/or long-term side effects to the patient. In addition, systemic administration of cytokines can be toxic and constitutive production of cytokines may lead to uncontrolled proliferation and transformation (Nagarkatti et al (1994) PNAS 91:7638-7642; Hassuneh et al (1997) Blood 89:610-620).

There is therefore a need for methods for enhancing engraftment and expansion of T cells within a patient which are not associated with the disadvantages and problems mentioned above.

The typical format of a chimeric antigen receptor is shown. These are type I transmembrane proteins. An ectodomain recognizes antigen. This is composed of an antibody derived single-chain variable fragment (scFv) which is attached to a spacer domain. This in turn is connected to a transmembrane domain which acts to anchor the molecule in the membrane. Finally, this is connected to an endodomain which acts to transmits intracellular signals to the cell. This is composed of one or more signalling domains.

Figure 2:
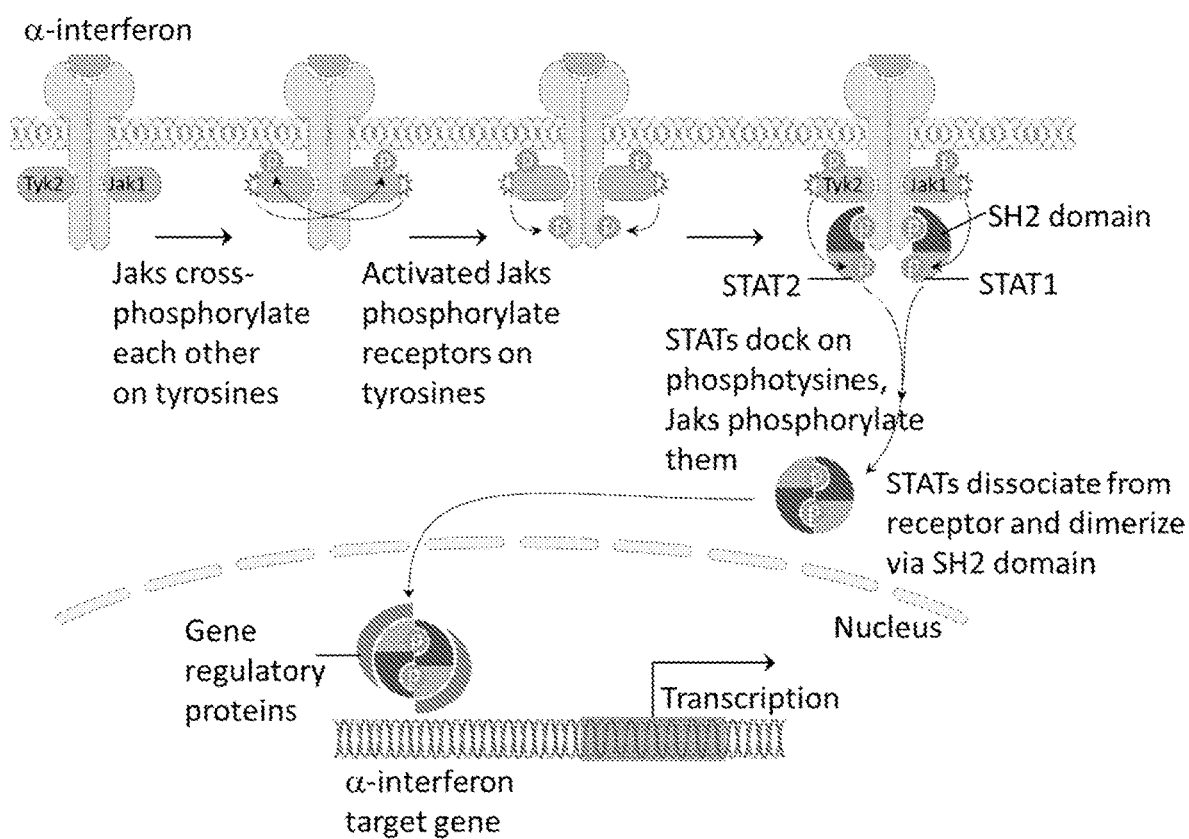

FIG. 2: Schematic diagram illustrating the JAK-STAT signaling pathway (activated by α-interferon).

Figure 3:
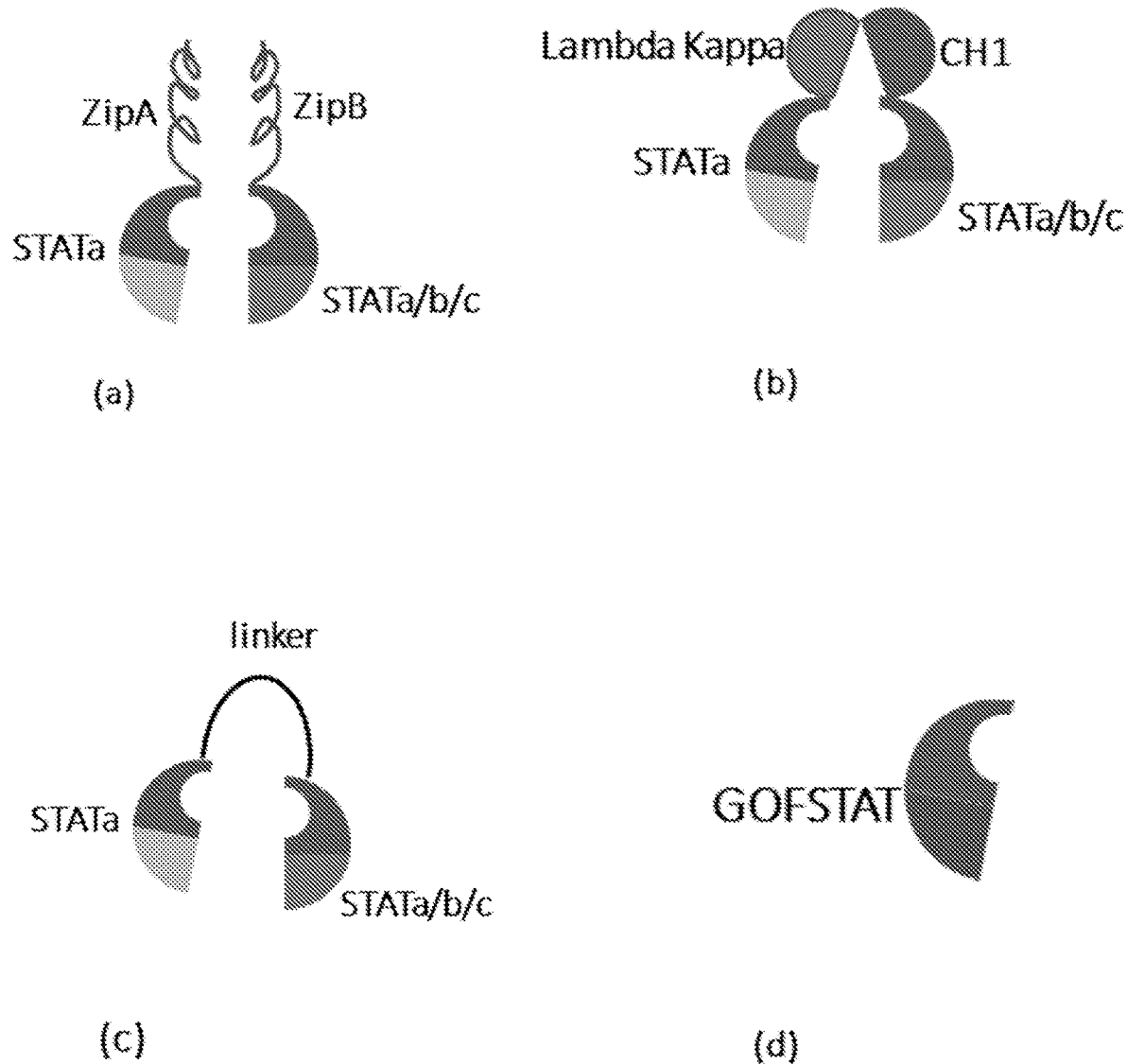

FIG. 3: Constitutively Active STAT Molecule Structures

Various alternative arrangements are shown to produce a constitutively active STAT molecule. The structures shown in (a) and (b) are made up of two polypeptides, each having a dimerization domain. In the structure shown in (a), both polypeptides have leucine zipper dimerization domains. In the structure shown in (b), one polypeptide has an antibody-type heavy chain constant region and one polypeptide has as light chain constant region. The structure shown in (c) has a linker sequence permanently joining the two STAT polypeptides. The STAT molecule of (a) to (c) may be a heterozygous or homozygous STAT molecule, as indicated by STATa and STATa/b/c. In the structure shown as (d) the STAT molecule comprises a gain of function (GOF) mutation.

Figure 4:
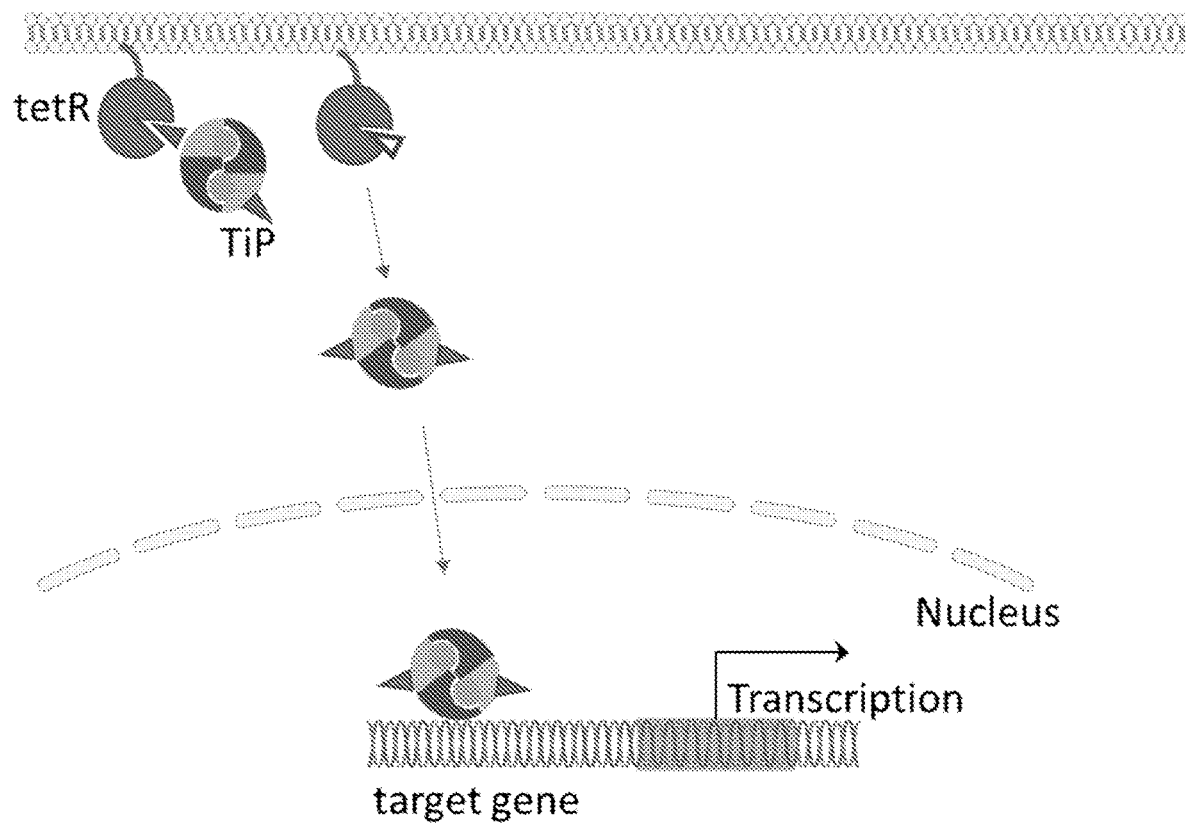

FIG. 4: Schematic diagram of a cell comprising a constitutively active STAT molecule which exerts its effect in the presence/absence of an agent. In this arrangement, the cell comprises a membrane-tethering molecule which has a first binding domain (BD) and a constitutively active STAT molecule which has a second BD. Proliferation/survival can be controlled by administration of an agent which disrupts binding of the first BD to the second BD, and leads to release of the active STAT molecule from the membrane-tethering molecule. Once released, the active STAT molecule is free to translocate to the nucleus, where it triggers DNA transcription.

FIG. 5: Schematic diagram of a cell comprising a constitutively active STAT molecule which is linked to recognition of a target antigen In the arrangement shown in (a) the cell comprises a chimeric molecule which comprises a CAR and a constitutively active STAT molecule. The chimeric molecule comprises a STAT release domain (e.g., protease cleavage site) between the STAT molecule and the CAR. The cell also comprises a STAT release molecule which releases the constitutively active STAT molecule by, for example, proteolytic cleavage.

In the arrangement shown in (a), the STAT release molecule comprises ZAP70 SH2 domains. When the CAR recognises its target antigen, the STAT release molecule binds phosphorylated immunoreceptor tyrosine based activation motifs (ITAMs) in the CAR endodomain. The protease domain of the STAT release molecule is then brought into proximity of the STAT release domain and the constitutively active STAT molecule is cleaved off. Once the constitutively active STAT molecule is released from the CAR, it can translocate to the nucleus and trigger DNA transcription.

In the arrangement shown in (b) the cell comprises a chimeric molecule which comprises a CAR linked to a constitutively active GOF STAT molecule by a STAT release domain having a protease cleavage site. The cell also comprises a STAT release molecule tethered to the endoplasmic reticulum (ER) via a retention motif. The STAT release molecule is released from the ER by addition of a small molecule.

For example, in the arrangement shown, the STAT release molecule comprises TiP and the membrane tethering molecule comprises TetRB so that addition of tetracycline causes dissociation of the STAT release molecule. The STAT release molecule comprises a ZAP70 SH2 domain, so that when the CAR recognises its target antigen, the STAT release molecule binds to the phosphorylated ITAM of the CAR, and the constitutively active STAT is released from the CAR by cleavage at the protease cleavage site. Both (a) and (b) trigger DNA transcription by the activated STAT molecule only when the CAR recognises a target antigen. The latter provides added safety since proliferation/survival can be controlled by administration of an agent (in this case tetracycline).

FIG. 6: Schematic diagram of a cell comprising an inducible STAT molecule

In the arrangement shown in (a), the cell comprises two STAT polypeptides with FKBP12/FRB hetrodimerization domains. Upon addition of an agent (rapamycin), dimerization of FKBP12 and FRB induces activation of the STAT molecule. In the arrangement shown in (b) the cell comprises an inducible STAT molecule which is inactivated in the presence of an agent. The cell of (b) comprises two STAT polypeptides, one with a TetR dimerization domain and one with a TiP dimerization domain. Addition of an agent such as tetracycline, doxycycline or minocycline causes dissociation of the STAT polypeptides.

FIG. 7: Amino acid sequence for a constitutively active STAT molecule of the type shown in FIG. 3c.

FIG. 8: Amino acid sequence for a construct which produces two proteins as illustrated in FIG. 4: a constitutively active STAT molecule with a TiP heterodimerisation domain; and a membrane tethering component having a myristoylation and palmitoylation sequence and a TetRB heterodimerisation domain.

Figure 5A:
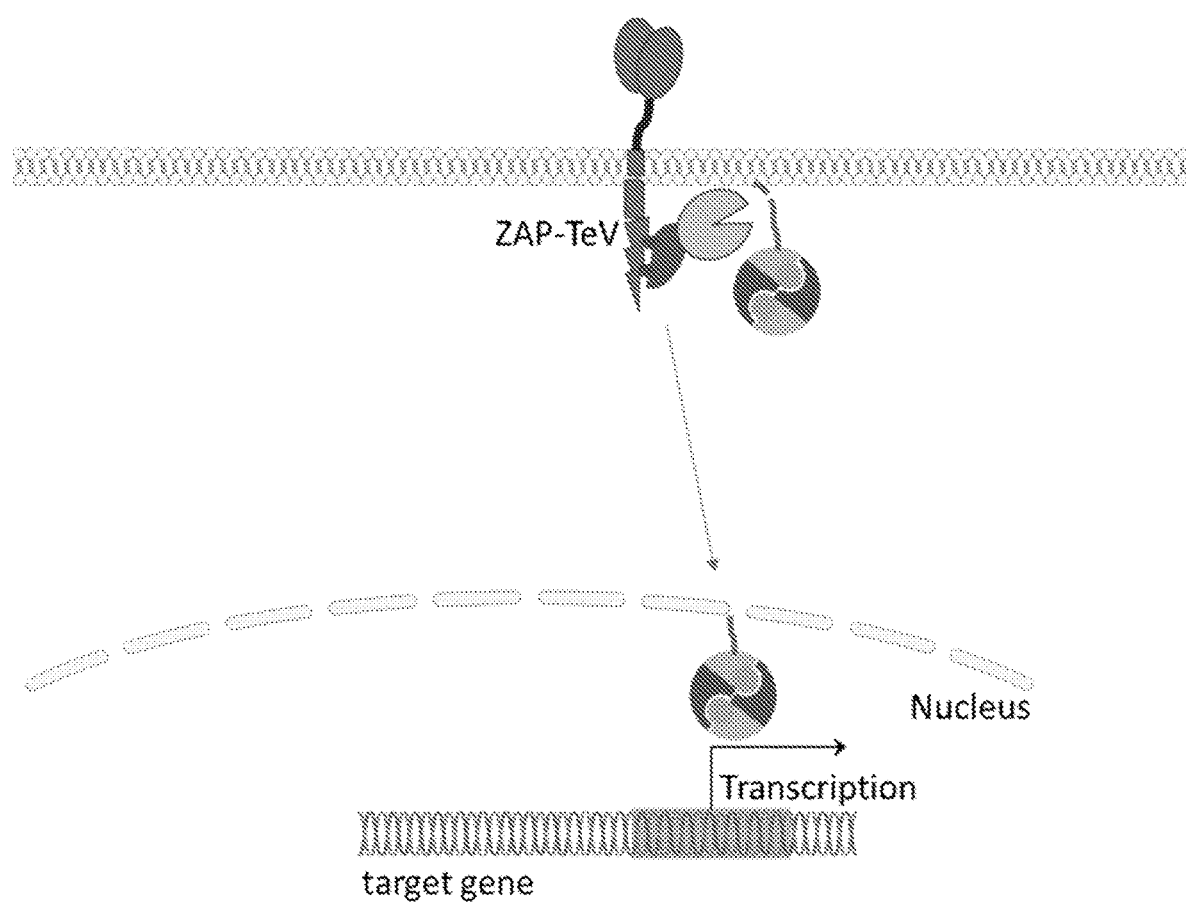

FIG. 9: Amino acid sequence for a construct which produces three proteins as illustrated in FIG. 5a: a chimeric antigen receptor; a membrane-tethered molecule which comprises a Myristoylation and palmitoylation sequence a TEV cleavage site and a constitutively active STAT molecule; and an intracellular molecule which comprises ZAP70 SH2 domains, linked to the TEV protease.

Figure 5B:
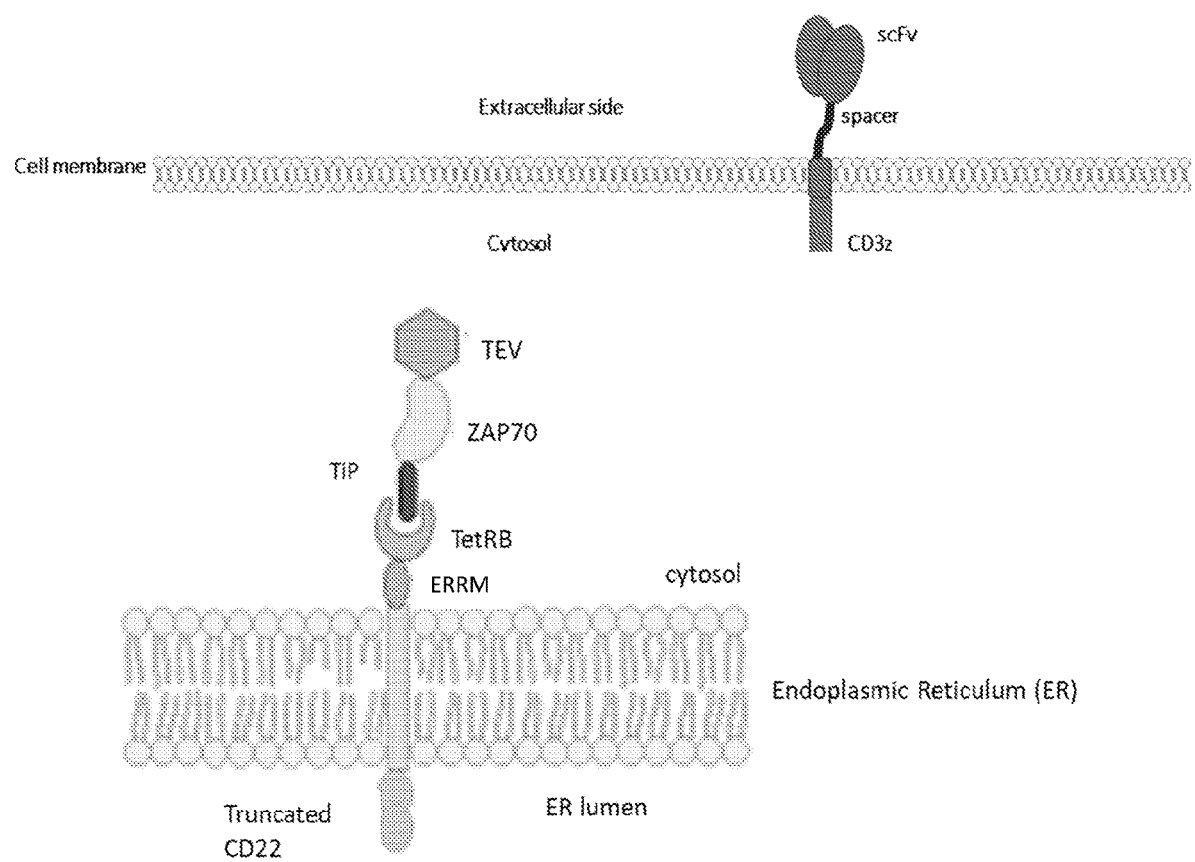

FIG. 10: Amino acid sequence for a construct which produces three proteins as illustrated in FIG. 5b: a chimeric antigen receptor linked an intracellular constitutively active (GOF) STAT molecule by a TEV cleavage site; an intracellular molecule comprising TEV protease, Zap70 SH2 domains and a TiP heterodimerisation domain; and an ER-located protein which comprises truncated CD22 in the ER lumen, a CD19 transmembrane domain, a Tyro-1 endodomain and a TetRB heterodimerasation domain.

Figure 6A:
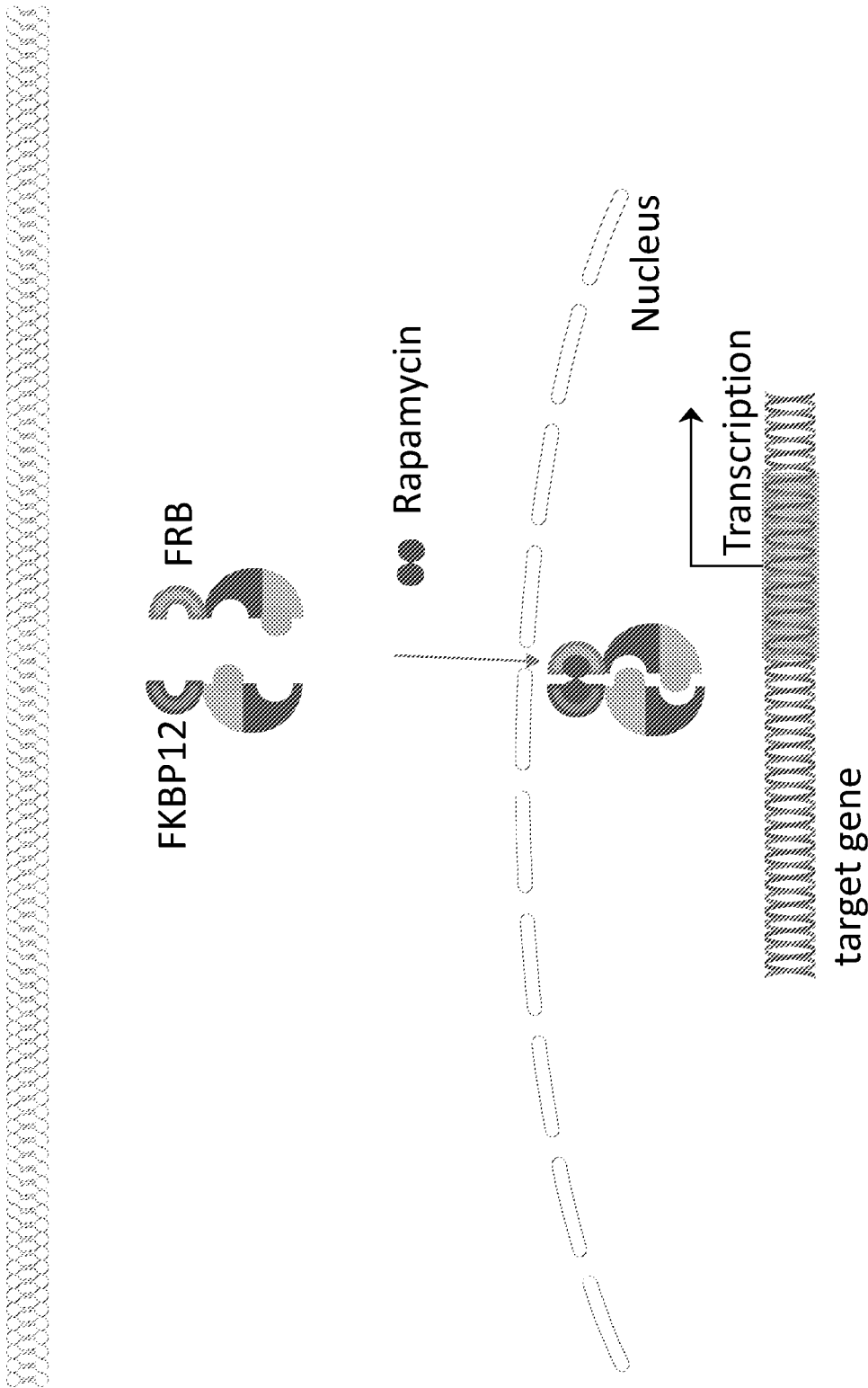

FIG. 11: Amino acid sequence for a construct which produces an inducible active STAT molecule as illustrated in FIG. 6a: a first polypeptide which comprises STAT5 and a FRB heterodimerisation domain; and a second polypeptide which comprises STAT 3 and an FKBP12 heterodimerisation domain.

Figure 6B:
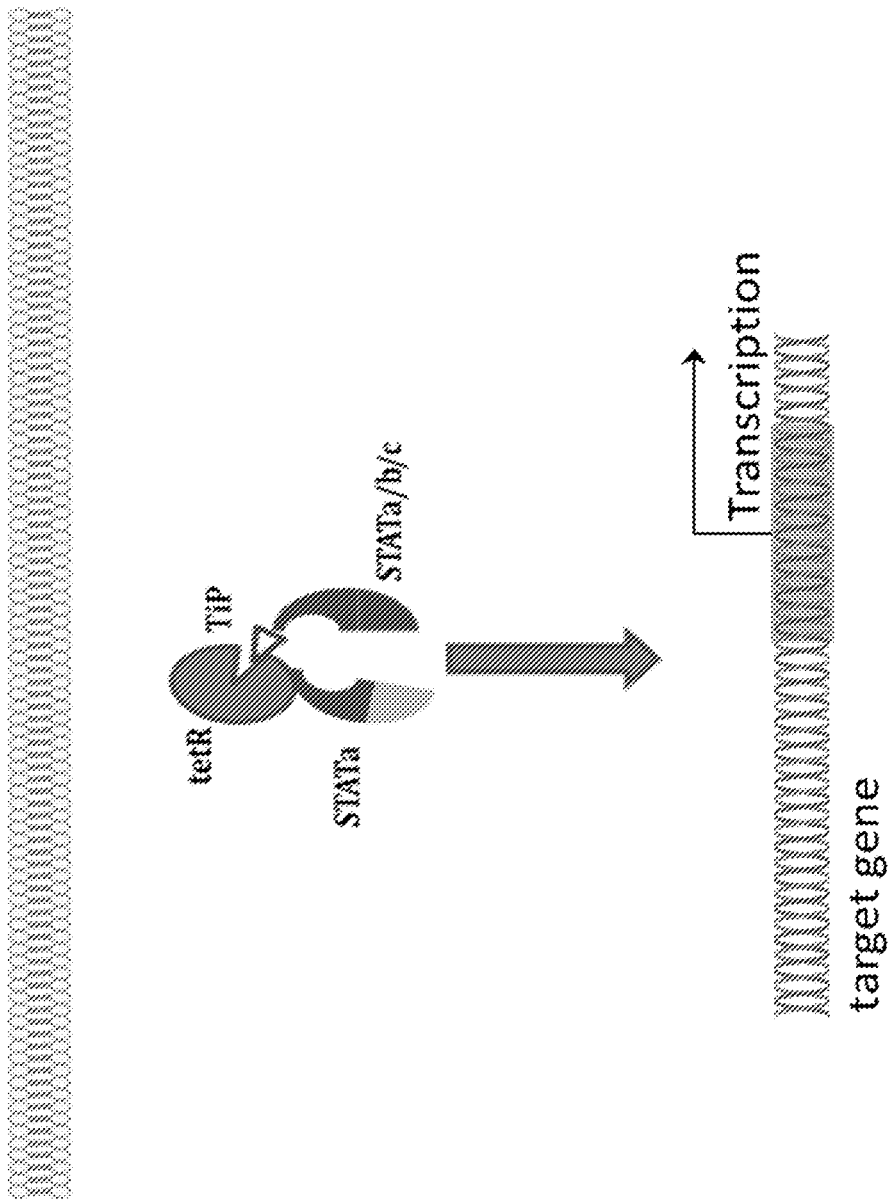

FIG. 12: Amino acid sequence for a construct which produces an inducible active STAT molecule as illustrated in FIG. 6b: a first polypeptide which comprises STAT5 and an TiP heterodimerisation domain; and a second polypeptide which comprises STAT3 and an TetRB heterodimerisation domain.

Figure 13:
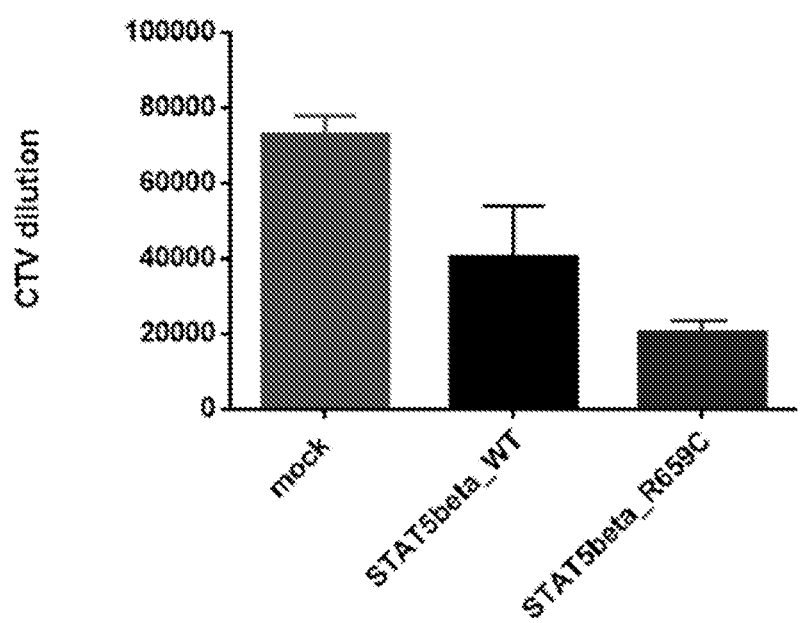

FIG. 13: Assessment of the propensity to proliferate in the absence of stimulation measured by CTV dilution. PBMCs transduced with either the wild type or mutant form of STAT5. They were labelled with cell trace violet (CTV) and left for 4 days in complete media without stimulation or exogenous cytokines. The constitutively active STAT molecule tested (STAT5beta_R659C gain of function mutation) demonstrated decreased CTV dilution values compared to the wild type construct (STAT5beta_WT). These results show that the mutant construct has increased propensity to proliferate compared to the wild type construct.

Figure 14:
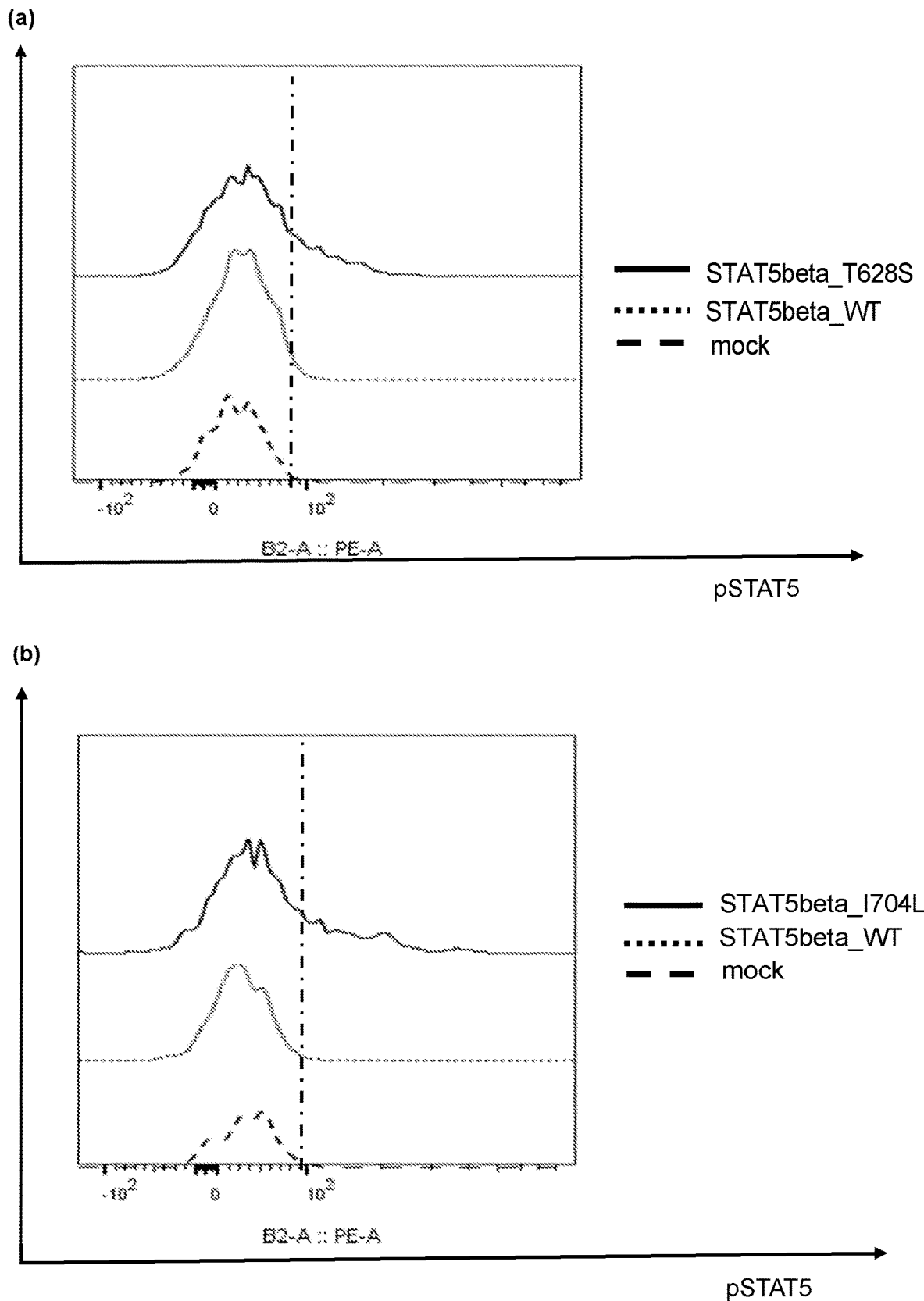

FIG. 14: Assessment of intracellular phosphorylated STAT5beta of constitutively active STAT mutants constructs compared to wild type. PBMCs transduced with either the wild type or mutant forms of STAT5 were left for 3 days in complete media without stimulation or exogenous cytokines. The baseline level of STAT phosphorylation was measured by flow cytometry. Both the constitutively active STAT molecules tested (a) STAT5beta_T628S and (b) STAT5beta_1704F gain of function mutations showed a greater degree of STAT5 phosphorylation as indicated in the histograms of FIGS. 14 (a) and (b), respectively, compared to the wild type constructs or controls. This greater degree of STAT5 phosphorylation in the absence of stimulus indicates baseline activation of these mutants.

Figure 15:
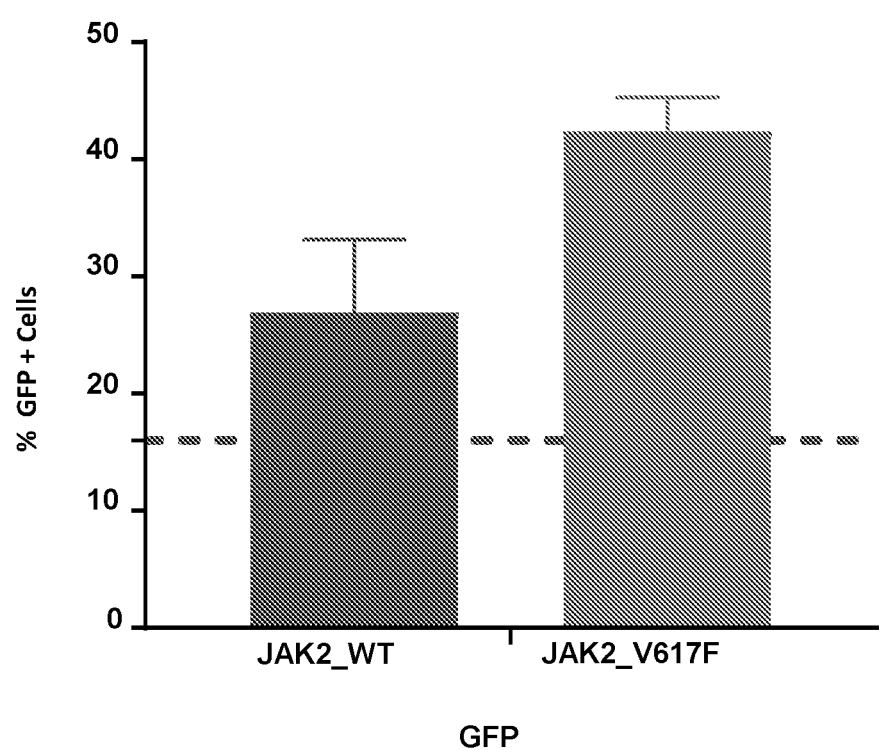
Figure 15:
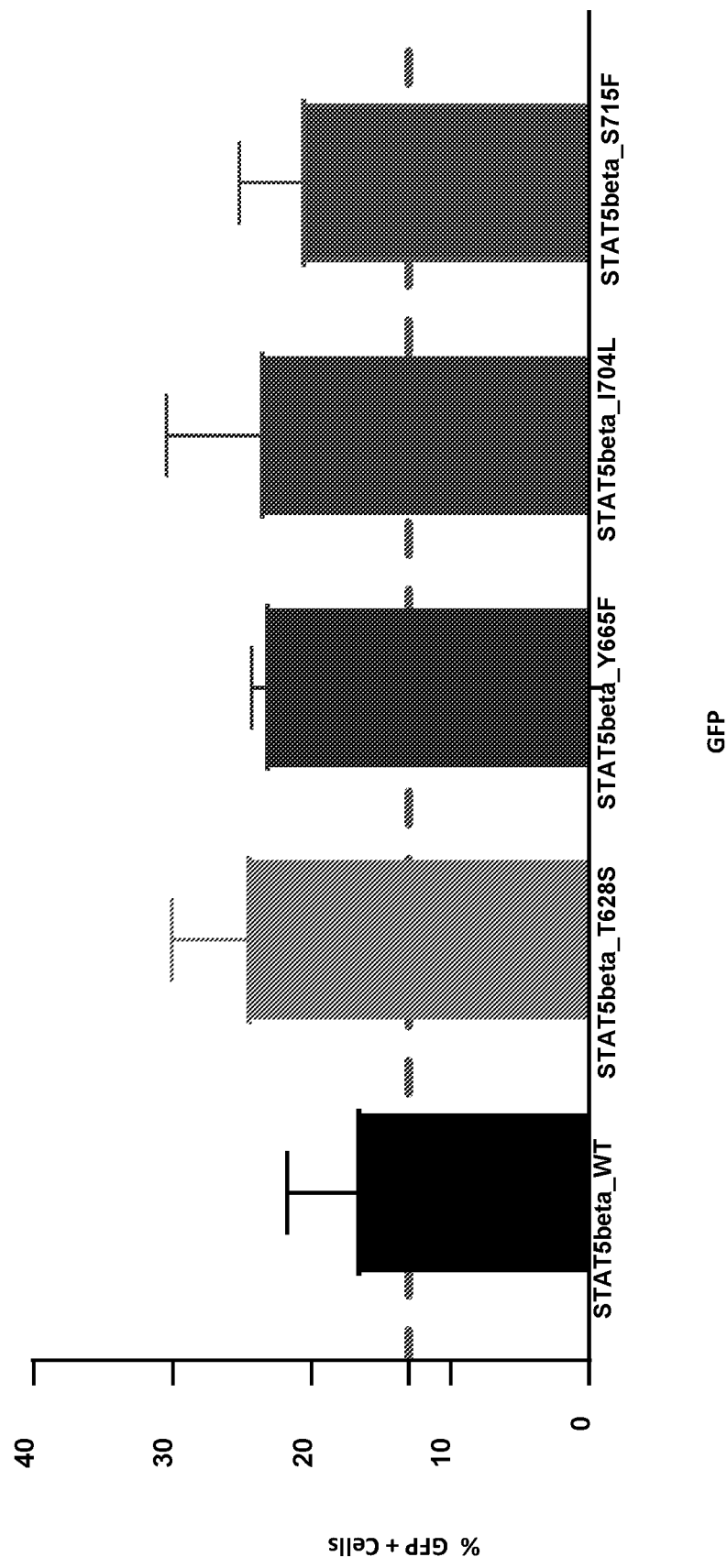

FIG. 15: Assessment of constitutively active JAK2 or STAT5 mutants to induce JAK2 or STAT5 dependent gene expression. A (a) JAK2 and (b) STAT5 dependent GFP reporter cell line was generated by transducing 293T cells with the self-inactivating vector construct comprising 3×STAT5 DNA responsive elements controlling the expression of GFP.

FIG. 15 shows an increase in GFP expression for the constitutively active (a) JAK2_V617F construct and (b) STAT5betaT628S, STAT5betaY665F, STAT5beta1704L, STATbetaS715F constructs, respectively, compared to the corresponding wild type constructs. This data indicates an increase in propensity for these mutants to drive genes from the STAT5 DNA responsive elements.

The dotted horizontal lines on the bar graphs of FIGS. 15(a) and 15(b) represents background expression.

SUMMARY OF ASPECTS OF THE INVENTION

The present inventors have found that it is possible to enhance engraftment and persistence of CAR-expressing cells, by including in the cell a constitutively active or inducible active Janus Kinase (JAK) or Signal Transducer and Activator of Transcription (STAT) molecule. These molecules are involved in the JAK STAT signalling cascade which triggers DNA transcription of cytokine-activated target genes.

In a first aspect, the present invention provides a cell which comprises a CAR and a constitutively active or an inducible Signal Transducer and Activator of Transcription (STAT) molecule.

The cell may be an immune effector cell, such as a T-cell or natural killer (NK) cell. The STAT molecule of the cell may comprise a first STAT polypeptide comprising a first dimerizing domain (DD) and a second STAT polypeptide comprising a second DD, which specifically binds to the first DD.

The first and second DDs of the STAT molecule of the cell may comprise leucine zipper domains.

Alternatively, the first and second DDs of the STAT molecule of the cell may comprise a heavy chain constant region and a light chain constant region, respectively.

The STAT molecule of the cell of the present invention may be inducible. This means that the STAT molecule may be inducibly inactive or inducibly active.

The STAT molecule of the cell may be inducibly active in the presence of an agent which causes dimerization of the first DD and second DD of the STAT molecule, thereby inducing activation of the STAT molecule. The first DD may comprise FRB, the second DD may comprise FKBP12 and the agent may be rapamycin.

Alternatively, the STAT molecule of the cell may be inducibly inactive in the presence of an agent which causes dissociation of the first DD and second DD of the STAT molecule, thereby inducing non-activation of the STAT molecule. The first DD may comprise TetRB and the second DD may comprise TiP and the agent may be tetracycline, doxycycline or minocycline.

The STAT molecule of the cell of the present invention may be constitutively active.

A constitutively active STAT may comprise a Gain of Function (GOF) mutation.

Alternatively, a constitutively active STAT molecule of the cell may comprise a first STAT polypeptide and a second STAT polypeptide linked by a linker sequence.

The cell may comprise a membrane-tethering molecule comprising a tethering domain and a first binding domain (BD), and a constitutively active STAT molecule which comprises a second BD which binds specifically to the first BD. Binding of the first and second BD may be disrupted by the presence of an agent, such that in the presence of the agent the constitutively active STAT molecule dissociates from the membrane-tethering molecule, so that the constitutively active STAT molecule is free to translocate to the nucleus.

The first and second DD of the STAT molecule of the cell; or the first BD of the membrane-tethering molecule of the cell and second BD of the STAT molecule of the cell may comprise a Tet Repressor Protein (TetR) and a Transcription Inducing Peptide (TiP), respectively; and the agent may be tetracycline, doxycycline or minocycline.

The cell may comprise a) a CAR and a constitutively active STAT molecule joined by a STAT release domain and b) a STAT release molecule which releases the constitutively active STAT molecule from the CAR at the STAT release domain only upon recognition of a target antigen specific to the CAR, such that upon release, the constitutively active STAT molecule is free to translocate to the nucleus.

The STAT release molecule of the cell of the present invention may comprise a CAR targeting domain, for example which binds to a phosphorylated immunoreceptors tyrosine based activation motif (ITAM).

The CAR targeting domain of the cell of the present invention may comprise one or more ZAP70 SH2 domains.

The STAT release domain of the cell of the present invention may comprise a protease cleavage site, and the STAT release molecule of the cell may comprise a protease domain, such that upon recognition of a target antigen of the CAR, the protease domain cleaves at the protease cleavage site, releasing the STAT molecule.

The cleavage site may be a Tobacco Etch Virus (TEV) protease cleavage site.

In a second aspect, the present invention provides a cell which comprises a CAR and a constitutively active or an inducible Janus Kinase (JAK) molecule.

In a third aspect, the present invention provides a nucleotide sequence encoding a constitutively active STAT molecule or an inducible STAT molecule as defined in the first aspect of the invention.

In a fourth aspect, the present invention provides a nucleotide construct which comprises a first nucleotide sequence as defined in the third aspect of the invention, and a second nucleotide sequence encoding the CAR.

The nucleotide construct may further comprise a third nucleotide sequence encoding a membrane-tethering molecule as defined in the first aspect of the invention.

The nucleotide construct may comprise a first nucleotide sequence encoding a CAR and a constitutively active STAT molecule joined by a STAT release domain as defined in a first aspect of the invention, and a second nucleotide sequence encoding for a STAT release molecule, as defined in a first aspect of the invention.

In a fifth aspect, the present invention provides a vector comprising a nucleotide sequence according to the third aspect or a nucleotide construct as defined in the fourth aspect.

In a sixth aspect, the present invention provides a pharmaceutical composition comprising a plurality of cells according to the first and/or second aspect of the invention.

In a seventh aspect, the present invention provides a pharmaceutical composition according the sixth aspect of the invention for use in treating and/or preventing a disease.

In an eighth aspect, the present invention provides a method for treating and/or preventing a disease, which comprises the step of administering a pharmaceutical composition according to the fifth aspect of the invention to a subject.

The method may comprise the following steps:
(i) isolation of a cell containing sample;
(ii) transduction or transfection of the cells with a nucleotide sequence according to the third aspect, a nucleotide construct according to a fourth aspect, or a vector according to the fifth aspect of the invention; and
(iii) administering the cells from (ii) to a subject.

The method may involve monitoring the progression of disease and/or monitoring toxic activity in the subject and may comprise the step of administering an agent for use in the cell as defined the first aspect, to the subject to provide acceptable levels of disease progression and/or toxic activity.

In a ninth aspect, the present invention provides a use of a pharmaceutical composition according to sixth aspect of the invention in the manufacture of a medicament for the treatment and/or prevention of a disease.

The disease may be cancer.

T cells, as well as CAR T cells, require cytokines to proliferate and survive. The present invention effectively hijacks the cytokine-activated JAK/STAT intracellular signalling cascade to enhance engraftment of CAR T cell in a patient. The incorporation of a constitutively active or inducible STAT molecule into a cell increases the transmission of information from chemical signals to the nucleus, resulting in increased expression of cytokine-activated target genes, and thereby increases persistence and cell survival of the CAR T cell.

DETAILED DESCRIPTION

Chimeric Antigen Receptors (CARS)

Figure 1:
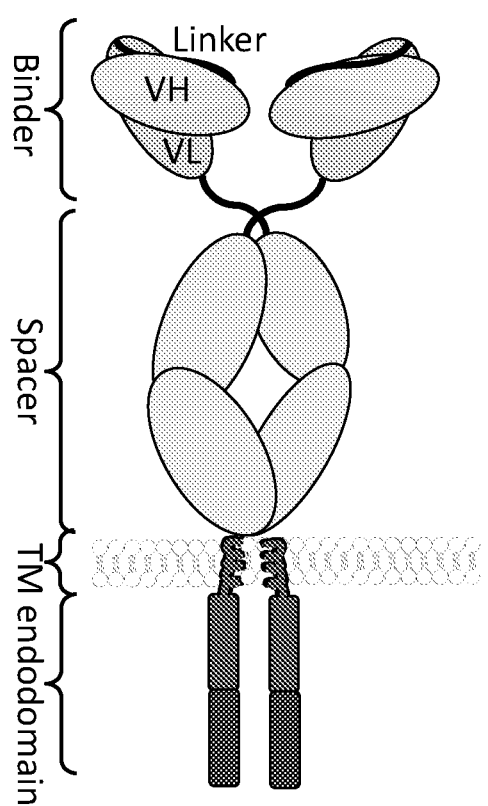
FIG. 1—Standard Design of a Chimeric Antigen Receptor

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A spacer domain may be necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals. CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus, the CAR directs the specificity and cytotoxicity of the T cell towards cells expressing the targeted antigen.

In the first aspect, the present invention relates to a cell which comprises a Chimeric Antigen Receptor (CAR) and a constitutively active or inducible Signal Transduction and Activator of Transcription (STAT) molecule.

The STAT molecule is part of the JAK STAT signalling pathway which plays a role in cytokine-activated immune responses.

JAK/STAT Signalling Pathway

Cytokines are regulatory molecules that coordinate immune responses. The most typical cytokine receptor is a protein that forms a stable association with a cytoplasmic tyrosine kinase known as the cytokine-activated Janus Kinase (JAK). This type of signaling is a rapid way to turn on a set of genes via triggering Signal Transducer and Activator of Transcription (STAT) molecules.

The JAK-STAT signalling pathway consists of three main components: (1) a receptor which penetrates the cell membrane (2) Janus kinase (JAK), which is bound to the receptor and (3) Signal Transducer and Activator of Transcription (STAT), which carries the signal into the nucleus and DNA.

FIG. 2 is a schematic diagram illustrating an α-interferon activated JAK STAT pathway, which activates the α-interferon target gene.

JAK

JAK is a family of intracellular tyrosine kinases that transduce cytokine-mediated signals. JAKs possess two phosphate-transferring domains, one exhibiting kinase activity and the other negatively regulating the kinase activity of the first.

There are four JAK family members: Janus Kinase 1 (JAK1); Janus Kinase 2 (JAK2); Janus Kinase 3 (JAK3); Tyrosine Kinase 2 (TYK2). Somatic activating mutations in JAK1, JAK2, and JAK3 have been identified in paediatric acute lymphoblastic leukemia (ALL) e.g., JAK2 mutations have been detected around the pseudokinase domain R683G in Down syndrome childhood B-ALL.

JAKs range from 120-140 kDa in size and have seven defined regions of homology (JH1-7). At the C-terminal end, JH-1 is the kinase domain important for the enzymatic activity of JAK and contains typical features of a tyrosine kinase such as conserved tyrosine resides (Y1038/Y1039 in JAK1, Y1007/Y1008 in JAK2, Y980/Y981 in JAK3 and Y1054/Y1055 in TYK2). Phosphorylation of these dual tyrosine residues leads to the conformations changes in JAK to facilitate binding of substrate. JH2 is a pseudokinase, structurally similar to JH1 but lacking enzymatic activity. This domain rather regulates the activity of JH1. The JH-3 and JH-4 domains of JAKs share homology with Src homology 2 (SH2) domains.

The tyrosine kinase activity of JAK is activated when the regulatory molecule binds and brings two receptor molecules together to form a dimer. Dimerization brings the two JAKs into close proximity, where they can phosphorylate each other. Phosphorylation further activates JAK, allowing it to phosphorylate the receptor. The phosphotryosine SH2 domains on the receptor proteins are binding sites for STAT proteins.

The binding of various ligands, usually cytokines such as interferon, interleukin and growth factors to cell surface receptors, activate associated JAKs, increasing their kinase activity, which then in turn activates STAT, triggering transcriptional activation of a cytokine-activated gene of interest.

In the context of the present invention, a constitutively active JAK molecule may be made by expressing two JAK polypeptides which spontaneously dimerise or are linked by a linker, as described below for constitutively active STAT molecules. Alternatively, constitutively active JAK may be expressed which comprises a gain-of-function mutation.

An inducible active JAK molecule may be by expressing two JAK polypeptides which dimerise in the presence of absence of an agent, as described below for STAT.

Signal Transducer and Activator of Transcription (STAT)

Signal Transducer and Activator of Transcription (STAT) molecules are a family of transcription factors that are involved in cytokine-mediated signal transduction. STAT transcription factors are recruited to the cytoplasmic region of cell surface receptors and are activated via phosphorylation. Once activated, they dimerize to form an acitvated STAT molecule comprising a first polypeptide and a second polypeptide, and translocate into the cell nucleus where they influence gene expression. They play a role in regulating cell growth processes and cell differentiation.

Each first and second polypeptide of the STAT molecules possess SH2 domains capable of binding phosphotyrosine residues recruited to the receptors, and are themselves tyrosine-phosphorylated by JAKs. These phosphotyrosines then act as binding sites for SH2 domains of other STAT molecules, mediating the dimerization.

Dimerization of the first and second polypeptide of the STAT molecule may be hetero- or homodimerization, for example, represented in FIGS. 3(a)-(d), STATa with STATa is homodimerization whereas STATa with either STATb or STATc is heterodimerization. Activated STAT dimers accumulate in the cell nucleus and activate transcription of their target genes.

There are seven mammalian STAT family members that have been identified: STAT1, STAT2, STAT3, STAT4, STAT5A, STAT5B and STATE. All seven STAT proteins share a common structural motif consisting of an N-terminal domain followed by a coiled-coil, DNA-binding, linker, Src homology 2 (SH2), and a C-terminal transactivation domain. Both the N-terminal and SH2 domains mediate homo or heterodimer formation, while the coiled-coil domain functions partially as a nuclear localization signal (NLS). Transcriptional activity and DNA association are determined by the transactivation and DNA-binding domains, respectively.

The presence of different STAT molecules in cells and activation of different cytokine receptors will result in the formation of different STAT dimers. Each naturally occurring STAT molecule is a dimer and binds to a specific DNA sequence found in the promoters of certain genes. Each cytokine activates a specific set of genes to cause a specific response in the cell. For example the STAT3/STAT1 polypeptide dimer is activated by the gp130 CD receptor and the STAT5/STAT3 polypeptide dimer is activated by the IL-2Rβ ICD.

Constitutitvely Active STAT Molecule

STAT molecules are considered latent transcription factors, meaning that they are always present, and waiting to be activated. A constitutively active STAT molecule triggers signal transduction without the dependency of the intracellular cytokine level or the phosphorylation state of various upstream signalling molecules in the JAK STAT signalling cascade. Co-expressing a constitutively active STAT with a CAR increases the proximity of the STAT molecule to the CAR compared to the physiological level of STAT freely circulating in the cytosol of the cell. The constitutively active STAT molecule in particular is advantageous as it may also bypass the usual requirement to activate JAK upstream of STAT activation.

The present inventors propose a number of different mechanisms to activate DNA transcription of the cytokine-activated target gene via STAT activation. The STAT molecule may be engineered to be constitutively active demonstrated schematically in FIGS. 3(a), (b), (c) and (d). For example, FIGS. 3(a) and (b) comprise a first and second polypeptide that are engineered to be physically bound together via the first and second dimerization domain (DD), without the need for a separate molecule acting as an "inducer" of dimerization.

First and Second Dimierisation Domain (DD)

The cell of the present invention may be engineered such that it comprises a STAT molecule, wherein the STAT molecule comprises a first STAT polypeptide comprising a first dimerizing domain (DD) and a second STAT polypeptide comprising a second DD, and wherein the first and second DD specifically bind to each other. In one embodiment, the dimerization of the first and second dimers occurs spontaneously, in which case the STAT protein will be constitutively active.

A large variety of appropriate dimerization domains are known in the art, examples of which are provided herein.

Leucine Zipper Domain

The first and second dimerization domains may be leucine zippers (FIG. 3(a)).

A leucine zipper is a super-secondary structure that functions as a dimerization domain. Its presence generates adhesion forces in parallel alpha helices. A single leucine zipper consists of multiple leucine residues at approximately 7-residue intervals, which forms an amphipathic alpha helix with a hydrophobic region running along one side. This hydrophobic region provides an area for dimerization, allowing the motifs to "zip" together. Leucine zippers are typically 20 to 40 amino acids in length, for example approximately 30 amino acids.

The first and/or second dimerization domain may comprise the sequence shown as SEQ ID NO: 1 or 2. The first dimerization domain may comprise the sequence shown as SEQ ID NO: 1 and the second dimerization domain may comprise the sequence shown as SEQ ID NO: 2, or vice versa.

```
SEQ ID NO: 1: QLEKELQALEKENAQLEWELQALEKELAQ

SEQ ID NO: 2: QLEKKLQALKKKNAQLKWKLQALKKKLAQ
```

In certain embodiments, the first and second dimerization domains may be acidic (e.g. SEQ ID NO: 1) or basic (e.g. SEQ ID NO: 2) leucine zippers. In particular, where the first heterodimerization domain is an acidic leucine zipper, the second heterodimerization is a basic leucine zipper and vice versa.

Heavy Chain and Light Chain Constant Region

Dimerisation of the first and second STAT polypeptides may be based on the dimerization domain of an antibody. In this arrangement the STAT polypeptides comprise the dimerization portion of a heavy chain constant domain (CH) and a light chain constant domain (CL) as depicted in FIG. 3(b). The dimerization portion of a constant domain is the part of the sequence which forms the inter-chain disulphide bond.

Linker Regions

Alternatively, the first and second polypeptides of STAT molecule may be linked together via a linker sequence (FIG. 3(c)). An example of an appropriate linker sequence could be the Glycine Serine linker sequence:

```
SEQ ID NO: 3: GGSG

SEQ ID NO: 4: GSGSGS

SEQ ID NO: 5: GGSGGGSG

SEQ ID NO: 6: SGGSGGSGG
```

A Gain Of Function (or GOF) mutation is a type of mutation in which the altered gene product possesses a new molecular function or a new pattern of gene expression (FIG. 3(d)). This new molecule function may be activation.

A specifically engineered GOF of a STAT molecule may be a constitutively active STAT molecule of the cell. Here, the site of the mutation is engineered at a particular residue of the STAT molecule responsible for the conformational change that occurs when the STAT molecule activates. This allows for activation without dimerization of the first and second polypeptide of a STAT dimer molecule since the mutation itself activates the STAT molecule.

A well-known example of a GOF mutation is of the STAT3 gene. This results in a condition (known as STAT3 GOF disease) wherein the STAT3 gene is hyperactive, leading to intrinsic increase of transcriptional activity and over-active T cell activity (Milner et al., Blood 2015 125: 591-599). The mutation comprises various mutations in multiple domains of the protein including the DNA binding, SH2 and C-terminal transactivation domains.

An example of a GOF mutation is S710F for STAT5, as shown in the sequence given in FIG. 10.

Inducible Stat Molecule

Alternatively, the STAT molecule may be inducible, and can be triggered to be active or inactive by, for example, addition of a small molecule such as an agent. This embodiment provides a means of controlling the activation or inactivation of a STAT molecule, in response to, for example, monitoring the progress of CAR T cell engraftment in the patient.

Agent

Dimerization of the first and second DDs of the first and second polypeptides of the inducible STAT molecule may occur only in the presence of an agent, such as with a chemical inducer of dimerization (CID). In bringing the two DDs together, the first and second polypeptides of the STAT dimer are brought together causing activation of the STAT molecule.

Alternatively, the agent may cause chemical dissociation of dimerization (CDD) of the first and second DDs by competitively binding to one of the DDs, and thus inhibiting dimerization of the first and second DDs, and therefore separating the first and second polypeptides of the STAT dimer. The CDD therefore prevents activation of the STAT molecule.

Suitable DDs and their associated agents are described in WO2015/150771, the contents of which are hereby incorporated by reference.

For example, one dimerization domain may comprise the rapamycin binding domain of FK-binding protein 12 (FKBP12), the other may comprise the FKBP12-Rapamycin Binding (FRB) domain of mTOR; and the CID agent may be rapamycin or a derivative thereof. In this embodiment, the STAT molecule is activated with addition of the agent Rapamycin since it induces dimerization of the first and second dimerization domains of the STAT molecule (see FIG. 6(a)).

One dimerization domain may comprise the FK506 (Tacrolimus) binding domain of FK-binding protein 12 (FKBP12) and the other dimerization domain may comprise the cyclosporin binding domain of cylcophilin A; and the CID may be an FK506/cyclosporin fusion or a derivative thereof.

One dimerization domain may comprise an oestrogen-binding domain (EBD) and the other dimerization domain may comprise a streptavidin binding domain; and the CID may be an estrone/biotin fusion protein or a derivative thereof.

One dimerization domain may comprise a glucocorticoid-binding domain (GBD) and the other dimerization domain may comprise a dihydrofolate reductase (DHFR) binding domain; and the CID may be a dexamethasone/methotrexate fusion protein or a derivative thereof.

One dimerization domain may comprise an 06-alkylguanine-DNA alkyltransferase (AGT) binding domain and the other dimerization domain may comprise a dihydrofolate reductase (DHFR) binding domain; and the CID may be an 06-benzylguanine derivative/methotrexate fusion protein or a derivative thereof.

One dimerization domain may comprise a retinoic acid receptor domain and the other dimerization domain may comprise an ecodysone receptor domain; and the CID may be RSL1 or a derivative thereof.

Alternatively, one dimerization domain may comprise Tet Repressor Protein (TetR) and the other dimerization domain may comprise a Transcription Inducing Peptide (TiP); and the CDD agent may be tetracycline, doxycycline or minocycline or a derivative thereof.

Membrane Tethering Molecule and Tethering Domain

In one embodiment, the cell of the invention comprising a CAR and a constitutively active STAT molecule, further comprises a membrane tethering molecule comprising a tethering domain and a first binding domain (BD). The constitutively active STAT molecule comprises a second BD, which binds specifically to the first BD.

The membrane tethering molecule may tether the first BD to the plasma membrane, as shown in FIG. 4. Alternatively, the membrane tethering molecule may tether the first BD to an endoplasmic reticulum (ER) membrane. The membrane tethering molecule may comprise an ER retention motif (ERRM) as shown in FIG. 5(b). A possible ERRM may comprise the Tyrp-1 endo peptide sequence.

First and Second Binding Domain (Bd)

As with the first and second DD, the first and second BD of the invention may be a Tet Repressor Protein (TetR) and a Transcription Inducing Peptide (TiP), respectively; and the agent may be tetracycline, doxycycline or minocycline.

Addition of a CDD agent such as tetracycline causes dissociation of the first BD (e.g., TetR) and second BD (e.g., TiP), such that the constitutively active STAT molecule is released from being tethered to the membrane (plasma or ER), freeing the molecule to translocate to the nucleus and trigger DNA transcription of the target gene. Tetracycline competitively binds to TeTR, displacing TiP from the membrane loci, so that the STAT molecule it is free to translocate through the cytosol to the nucleus.

Stat Release Molecule and Stat Release Domain

The STAT release molecule comprises a domain capable of cleaving the site between the CAR and the active STAT molecule.

The STAT release domain may comprise any sequence which enables the CAR and the STAT molecule of the cell of the invention to become separated, permitting the STAT molecule to be released and then translocate to the nucleus. The STAT release domain may comprise a cleavage site.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond).

Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

Stat Moleucle Linked to Car Target Antigen Recognition

In one embodiment, the STAT release domain is only cleaved by the STAT release molecule upon recognition of a target antigen by the CAR.

The STAT release molecule may comprise a CAR targeting domain which binds to a phosphorylated immunoreceptors tyrosine based activation motif (ITAM) on the CAR endodomain. The CAR targeting domain may comprise ZAP70 SH2 domains, as shown in FIGS. 5(a) and 5(b).

Antigen Binding Domain

The antigen-binding domain is the portion of the CAR which recognises the target antigen. It usually comprises an antibody-derived binding site, such as a scFv. Alternatively the binding site may be based on a ligand for the target antigen.

The CAR may specifically bind a tumour-associated cell-surface antigen.

Various tumour associated antigens (TAA) are known, some of which are shown in Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Spacer

The chimeric antigen receptor may comprise a spacer to connect the antigen-binding domain with the transmembrane domain and spatially separate the antigen-binding domain from the endodomain. A flexible spacer allows to the antigen-binding domain to orient in different directions to enable antigen binding.

The spacer sequence may, for example, comprise an IgG1 Fc region, an IgG1 hinge or a CD8 stalk. The linker may alternatively comprise an alternative linker sequence which has similar length and/or domain spacing properties as an IgG1 Fc region, an IgG1 hinge or a CD8 stalk.

Transmembrane Domain

The transmembrane domain is the sequence of a CAR that spans the membrane. It may comprise a hydrophobic alpha helix. The transmembrane domain may be derived from CD19 or CD28 (which gives good receptor stability).

Car Signal Peptide

The CAR described herein may comprise a signal peptide so that when it is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

Car Endodomain

The endodomain is the portion of a CAR which is located on the intracellular side of the membrane.

The endodomain is the signal-transmission portion of a CAR. After antigen recognition by the antigen binding domain, individual CAR molecules cluster, native CD45 and CD148 are excluded from the synapse and a signal is transmitted to the cell.

The CAR endodomain may be or comprise an intracellular signalling domain. In an alternative embodiment, the endodomain of the present CAR may be capable of interacting with an intracellular signalling molecule which is present in the cytoplasm, leading to signalling.

The most commonly used signalling domain component is that of CD3-zeta endodomain, which contains three ITAMs. This transmits an activation signal to the T cell after antigen is bound. CD3-zeta may not provide a fully competent activation signal and additional co-stimulatory signalling may be needed. For example, the CAR may also comprise an endodomain from OX40 or 41BB. The CAR may alternatively or additional comprise an endodomain from CD28.

The CAR endodomain may alternatively or additionally comprise one or more of the following: an ICOS endodomain, a CD27 endodomain, a BTLA endodomain, a CD30 endodomain, a GITR endodomain and an HVEM endodomain.

Nucleic Acid

The present invention provides a nucleotide sequence encoding a constitutively active STAT or an inducible STAT molecule of the invention.

Nucleic Acid Construct

The present invention further provides a nucleotide construct comprising a first nucleotide sequence encoding a constitutively active STAT or inducible STAT molecule, along with a second nucleotide sequence encoding a CAR.

The nucleic acid construct may comprise a cleavage site, such that the STAT molecule and CAR are expressed as separate polypeptides As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Vector

The present invention also provides a vector, which comprises a nucleic acid sequence(s) or nucleic acid construct of the invention. The vector may be used to introduce the nucleic acid sequence(s) into a host cell so that it expresses a CAR and a STAT molecule according to the first aspect of the invention.

The vector may, for example, be a plasmid or a viral vector, such as a retroviral vector or a lentiviral vector, or a transposon based vector or synthetic mRNA. The vector may be capable of transfecting or transducing a T cell or a NK cell.

Cell

The present invention provides a cell which comprises a CAR and a constitutively active or inducible STAT molecule.

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR-expressing cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR and STAT molecule-expressing cells are generated by introducing DNA or RNA coding for the CAR and STAT molecule by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR and constitutively active STAT molecule according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a CAR.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The present invention provides a CAR and constitutively active or inducible STAT molecule-expressing cell of the present invention for use in treating and/or preventing a disease.

The invention also relates to the use of a CAR and the constitutively active or inducible STAT molecule expressing cell of the present invention in the manufacture of a medicament for the treatment and/or prevention of a disease.

The disease to be treated and/or prevented by the methods of the present invention may be a cancerous disease, such as Acute lymphoblastic leukemia (ALL), chronic lymphoblastic leukemia (CLL), bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

The cells and pharmaceutical compositions of present invention may be for use in any of the methods described above.

Cell Comprising a Car and a Constitutively Active or Inducible Janus Kinase (JAK) Molecule The present invention also provides a cell comprising a chimeric antigen receptor (CAR) and a constitutively active or inducible JAK molecule.

The sections above relating to nucleotide sequences and constructs, vectors, pharmaceutical compositions and uses thereof, and methods also apply to the cell of the present invention which comprises a CAR and a constitutively active or inducible JAK molecule.

The invention will now be further described by way of Examples, which are meant to serve to assist one of ordinary skill in the art in carrying out the invention and are not intended in any way to limit the scope of the invention.

EXAMPLES

T-cell persistence, engraftment and exhaustion are tested in standard in vitro and in vivo assays.

Example 1: In Vitro Testing

In vitro assays comprise of a series of repetitive stimulation assays. T cells are transduced with target cells (e.g., anti-CD19 CAR) expressing the cognate ligand for 84 hours at a 1:1 target to effector ratio.

During this period of time, the rate of target cell cytolysis is assessed using automated real-time florescence measurements of the target cells. After co-incubation, the supernatant is used to measure IFN-γ release. In addition, the CAR T-cells are collected, counted and assessed for differentiation markers (e.g., CD45RA, CCR7) and exhaustion markers (e.g., PD1, Tim3 or LAG3) and then re-challenged with new target cells for a further 84 hours.

The process is repeated with several rounds of stimulation and assessed until there are not enough CAR T-cells to proceed due to a lack of proliferation or T-cell death. Proliferation of T cells and T-cell death is determined using automated real-time fluorescence measurements of the target cells.

Example 2: In Vivo Testing

In vivo assays comprise of standard immune competent mouse models where tumour is subcutaneously injected and the ability for T-cells to eliminate the tumour is assess over a period of two to ten weeks. By way of example, the assays comprise of orthotropic glioma mouse model expressing the cognate ligand EGFRVIII.

Mice are used in re-inoculation studies and surviving CAR T cells are used in adoptive cell transfer experiments where CAR T-cells from a cured mouse are transferred into a newly inoculated mouse to assess CAR T cell exhaustion. Further, engraftment/expansion of T-cells at the tumour bed or within lymphoid tissues such as lymph nodes, spleen and bone-marrow measured by flow cytometry and bioluminescence imaging of said tissues.

Example 3: Testing the Inducible and Constitutively Active STAT Constructs

A panel of constructs comprising the inducible or constitutively active STAT are placed in conjunction with a CAR directed against CD19 and subjected to an in vitro assay described in Example 1, comprising of a series of repetitive stimulations. The constitutively active STAT constructs depicted in FIGS. 5(a) and (b) comprise regions encoding an anti-CD19 CAR (aCD19) and are subjected to the same in vitro assay. The transduced T cells are challenged with target cells expressing CD19 for 84 hours at a 1:1 target to effector ratio, as described above.

SEQ ID NO: 7 is used to test the construct depicted in FIG. 3(c).

SEQ ID NO: 8 is used to test the construct depicted in FIG. 4.

SEQ ID NOs: 9 and 10 are used to test the constructs depicted in FIGS. 5(a) and (b).

SEQ ID Nos: 11 and 12 are used to test the constructs depicted in FIGS. 6(a) and (b).

The constitutively active STAT constructs tested in Example 3 comprise the following amino acid sequences:

SEQ ID NO: 7
(STAT3 - Linker - STAT5)
MAQWNQLQQLDTRYLEQLHQLYSDSFPMELRQFLAPWIESQDWAYAASKESHATL

VFHNLLGEIDQQYSRFLQESNVLYQHNLRRIKQFLQSRYLEKPMEIARIVARCLWEE

SRLLQTAATAAQQGGQANHPTAAVVTEKQQMLEQHLQDVRKRVQDLEQKMKVVE

NLQDDFDFNYKTLKSQGDMQDLNGNNQSVTRQKMQQLEQMLTALDQMRRSIVSEL

AGLLSAMEYVQKTLTDEELADWKRRQQIACIGGPPNICLDRLENWITSLAESQLQTR

QQIKKLEELQQKVSYKGDPIVQHRPMLEERIVELFRNLMKSAFVVERQPCMPMHPD

RPLVIKTGVQFTTKVRLLVKFPELNYQLKIKVCIDKDSGDVAALRGSRKFNILGTNTKV

MNMEESNNGSLSAEFKHLTLREQRCGNGGRANCDASLIVTEELHLITFETEVYHQG

LKIDLETHSLPVVVISNICQMPNAWASILWYNMLTNNPKNVNFFTKPPIGTWDQVAEV

LSWQFSSTTKRGLSIEQLTTLAEKLLGPGVNYSGCQITWAKFCKENMAGKGFSFWV

WLDNIIDLVKKYILALWNEGYIMGFISKERERAILSTKPPGTFLLRFSESSKEGGVTFT

WVEKDISGKTQIQSVEPYTKQQLNNMSFAEIIMGYKIMDATNILVSPLVYLYPDIPKEE

AFGKYCRPESQEHPEADPGSAAPYLKTKFICVTPTTCSNTIDLPMSPRTLDSLMQFG

NNGEGAEPSAGGQFESLTFDMELTSECATSPMSGGGGSGGGGSGGGGSGGGGS

GGGGSMAGWIQAQQLQGDALRQMQVLYGQHFPIEVRHYLAQWIESQPWDAIDLDN

PQDRAQATQLLEGLVQELQKKAEHQVGEDGFLLKIKLGHYATQLQKTYDRCPLELV

RCIRHILYNEQRLVREANNCSSPAGILVDAMSQKHLQINQTFEELRLVTQDTENELKK

LQQTQEYFIIQYQESLRIQAQFAQLAQLSPQERLSRETALQQKQVSLEAWLQREAQT

LQQYRVELAEKHQKTLQLLRKQQTIILDDELIQWKRRQQLAGNGGPPEGSLDVLQS

WCEKLAEIIWQNRQQIRRAEHLCQQLPIPGPVEEMLAEVNATITDIISALVTSTFIIEKQ

PPQVLKTQTKFAATVRLLVGGKLNVHMNPPQVKATIISEQQAKSLLKNENTRNECSG

EILNNCCVMEYHQATGTLSAHFRNMSLKRIKRADRRGAESVTEEKFTVLFESQFSVG

SNELVFQVKTLSLPVVVIVHGSQDHNATATVLWDNAFAEPGRVPFAVPDKVLWPQL

CEALNMKFKAEVQSNRGLTKENLVFLAQKLFNNSSSHLEDYSGLSVSWSQFNRENL

PGWNYTFWQWFDGVMEVLKKHHKPHWNDGAILGFVNKQQAHDLLINKPDGTFLLR

FSDSEIGGITIAWKFDSPERNLWNLKPFTTRDFSIRSLADRLGDLSYLIYVFPDRPKDE

VFSKYYTPVLAKAVDGYVKPQIKQVVPEFVNASADAGGSSATYMDQAPSPAVCPQA

PYNMYPQNPDHVLDQDGEFDLDETMDVARHVEELLRRPMDSLDSRLSPPAGLFTS

ARGSLS

SEQ ID NO: 8
(TIP - STAT3 - Linker - STAT5 - 2a - Myristoylation and palmitoylation sequence - Ridge Linker - TetRB)
MWTWNAYAFAAPSGGGSAQWNQLQQLDTRYLEQLHQLYSDSFPMELRQFLAPWI

ESQDWAYAASKESHATLVFHNLLGEIDQQYSRFLQESNVLYQHNLRRIKQFLQSRYL

EKPMEIARIVARCLWEESRLLQTAATAAQQGGQANHPTAAVVTEKQQMLEQHLQDV

-continued

RKRVQDLEQKMKVVENLQDDFDFNYKTLKSQGDMQDLNGNNQSVTRQKMQQLEQ

MLTALDQMRRSIVSELAGLLSAMEYVQKTLTDEELADWKRRQQIACIGGPPNICLDR

LENWITSLAESQLQTRQQIKKLEELQQKVSYKGDPIVQHRPMLEERIVELFRNLMKS

AFVVERQPCMPMHPDRPLVIKTGVQFTTKVRLLVKFPELNYQLKIKVCIDKDSGDVA

ALRGSRKFNILGTNTKVMNMEESNNGSLSAEFKHLTLREQRCGNGGRANCDASLIV

TEELHLITFETEVYHQGLKIDLETHSLPVVVISNICQMPNAWASILWYNMLTNNPKNV

NFFTKPPIGTWDQVAEVLSWQFSSTTKRGLSIEQLTTLAEKLLGPGVNYSGCQITWA

KFCKENMAGKGFSFWVWLDNIIDLVKKYILALWNEGYIMGFISKERERAILSTKPPGT

FLLRFSESSKEGGVTFTWVEKDISGKTQIQSVEPYTKQQLNNMSFAEIIMGYKIMDAT

NILVSPLVYLYPDIPKEEAFGKYCRPESQEHPEADPGSAAPYLKTKFICVTPTTCSNTI

DLPMSPRTLDSLMQFGNNGEGAEPSAGGQFESLTFDMELTSECATSPMSGGGGS

GGGGSGGGGSGGGGSGGGGSMAGWIQAQQLQGDALRQMVLYGQHFPIEVRHY

LAQWIESQPWDAIDLDNPQDRAQATQLLEGLVQELQKKAEHQVGEDGFLLKIKLGH

YATQLQKTYDRCPLELVRCIRHILYNEQRLVREANNCSSPAGILVDAMSQKHLQINQ

TFEELRLVTQDTENELKKLQQTQEYFIIQYQESLRIQAQFAQLAQLSPQERLSRETAL

QQKQVSLEAWLQREAQTLQQYRVELAEKHQKTLQLLRKQQTIILDDELIQWKRRQQ

LAGNGGPPEGSLDVLQSWCEKLAEIIWQNRQQIRRAEHLCQQLPIPGPVEEMLAEV

NATITDIISALVTSTFIIEKQPPQVLKTQTKFAATVRLLVGGKLNVHMNPPQVKATIISE

QQAKSLLKNENTRNECSGEILNNCCVMEYHQATGTLSAHFRNMSLKRIKRADRRGA

ESVTEEKFTVLFESQFSVGSNELVFQVKTLSLPVVVIVHGSQDHNATATVLWDNAFA

EPGRVPFAVPDKVLWPQLCEALNMKFKAEVQSNRGLTKENLVFLAQKLFNNSSSHL

EDYSGLSVSWSQFNRENLPGWNYTFWQWFDGVMEVLKKHHKPHWNDGAILGFVN

KQQAHDLLINKPDGTFLLRFSDSEIGGITIAWKFDSPERNLWNLKPFTTRDFSIRSLA

DRLGDLSYLIYVFPDRPKDEVFSKYYTPVLAKAVDGYVKPQIKQVVPEFVNASADAG

GSSATYMDQAPSPAVCPQAPYNMYPQNPDHVLDQDGEFDLDETMDVARHVEELL

RRPMDSLDSRLSPPAGLFTSARGSLSEGRGSLLTCGDVEENPGPMGCGCSSHPEL

EAEAAAKEAAAKEAAAKEAAAKALEAEAAAKEAAAKEAAAKEAAAKALESGGGSMS

RLDKSKVINSALELLNEVGIEGLTTRKLAQKLGVEQPTLYWHVKNKRALLDALAIEML

DRHHTHFCPLEGESWQDFLRNNAKSFRCALLSHRDGAKVHLGTRPTEKQYETLEN

QLAFLCQQGFSLENALYALSAVGHFTLGCVLEDQEHQVAKEERETPTTDSMPPLLR

QAIELFDHQGAEPAFLFGLELIICGLEKQLKCESGS

SEQ ID NO: 9
(SH2 ZAP70 - Linker - TEV - 2a - myristoylation and palmitoylation
sequence - linker - TEV cleavage site x3 - STAT3 - Linker -
STAT5- 2a - aCD19)
MPDPAAHLPFFYGSISRAEAEEHLKLAGMADGLFLLRQCLRSLGGYVLSLVHDVRFH

HFPIERQLNGTYAIAGGKAHCGPAELCEFYSRDPDGLPCNLRKPCNRPSGLEPQPG

VFDCLRDAMVRDYVRQTWKLEGEALEQAIISQAPQVEKLIATTAHERMPWYHSSLT

REEAERKLYSGAQTDGKFLLRPRKEQGTYALSLIYGKTVYHYLISQDKAGKYCIPEG

TKFDTLWQLVEYLKLKADGLIYCLKEACPNSSASNASGAAAPTLPAHPSTLTHPSGG

GGSSLFKGPRDYNPISSTICHLTNESDGHTTSLYGIGFGPFIITNKHLFRRNNGTLLVQ

SLHGVFKVKNTTTLQQHLIDGRDMIIIRMPKDFPPFPQKLKFREPQREERICLVTTNF

QTKSMSSMVSDTSCTFPSSDGIFWKHWIQTKDGQCGSPLVSTRDGFIVGIHSASNF

```
TNTNNYFTSVPKNFMELLTNQEAQQWVSGWRLNADSVLWGGHKVFMSKPEEPFQ
PVKEATQLMNELVYSQEGRGSLLTCGDVEENPGPMGCGCSSHPESGGGGSGGG
GSENLYFQGENLYFQGENLYFQGENLYFQGENLYFQGENLYFQGENLYFQGENLY
FQGENLYFQGAQWNQLQQLDTRYLEQLHQLYSDSFPMELRQFLAPWIESQDWAYA
ASKESHATLVFHNLLGEIDQQYSRFLQESNVLYQHNLRRIKQFLQSRYLEKPMEIARI
VARCLWEESRLLQTAATAAQQGGQANHPTAAVVTEKQQMLEQHLQDVRKRVQDL
EQKMKVVENLQDDFDFNYKTLKSQGDMQDLNGNNQSVTRQKMQQLEQMLTALDQ
MRRSIVSELAGLLSAMEYVQKTLTDEELADWKRRQQIACIGGPPNICLDRLENWITSL
AESQLQTRQQIKKLEELQQKVSYKGDPIVQHRPMLEERIVELFRNLMKSAFVVERQP
CMPMHPDRPLVIKTGVQFTTKVRLLVKFPELNYQLKIKVCIDKDSGDVAALRGSRKF
NILGTNTKVMNMEESNNGSLSAEFKHLTLREQRCGNGGRANCDASLIVTEELHLITF
ETEVYHQGLKIDLETHSLPVVVISNICQMPNAWASILWYNMLTNNPKNVNFFTKPPIG
TWDQVAEVLSWQFSSTTKRGLSIEQLTTLAEKLLGPGVNYSGCQITWAKFCKENMA
GKGFSFWVWLDNIIDLVKKYILALWNEGYIMGFISKERERAILSTKPPGTFLLRFSESS
KEGGVTFTWVEKDISGKTQIQSVEPYTKQQLNNMSFAEIIMGYKIMDATNILVSPLVY
LYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPMSGGGGSGGGGSGG
GGSGGGGSGGGGSMAGWIQAQQLQGDALRQMVLYGQHFPIEVRHYLAQWIESQ
PWDAIDLDNPQDRAQATQLLEGLVQELQKKAEHQVGEDGFLLKIKLGHYATQLQKT
YDRCPLELVRCIRHILYNEQRLVREANNCSSPAGILVDAMSQKHLQINQTFEELRLVT
QDTENELKKLQQTQEYFIIQYQESLRIQAQFAQLAQLSPQERLSRETALQQKQVSLE
AWLQREAQTLQQYRVELAEKHQKTLQLLRKQQTIILDDELIQWKRRQQLAGNGGPP
EGSLDVLQSWCEKLAEIIWQNRQQIRRAEHLCQQLPIPGPVEEMLAEVNATITDIISAL
VTSTFIIEKQPPQVLKTQTKFAATVRLLVGGKLNVHMNPPQVKATIISEQQAKSLLKN
ENTRNECSGEILNNCCVMEYHQATGTLSAHFRNMSLRIKRADRRGAESVTEEKFT
VLFESQFSVGSNELVFQVKTLSLPVVVIVHGSQDHNATATVLWDNAFAEPGRVPFA
VPDKVLWPQLCEALNMKFKAEVQSNRGLTKENLVFLAQKLFNNSSSHLEDYSGLSV
SWSQFNRENLPGWNYTFWQWFDGVMEVLKKHHKPHWNDGAILGFVNKQQAHDLL
INKPDGTFLLRFSDSEIGGITIAWKFDSPERNLWNLKPFTTRDFSIRSLADRLGDLSYL
IYVFPDRPKDEVFSKYYTPVLAKAVDGYVKPQIKQVVPEFVNASADAGGSSATYMD
QAPSPAVCPQAPYNMYPQNPDHVLDQDGEFDLDETMDVARHVEELLRRPMDSLDS
RLSPPAGLFTSARGSLSEGRGSLLTCGDVEENPGPMETDTLLLWVLLLWVPGSTGD
IQMTQTTSSLSASLGDRVTISCRASQDISKYLNWYQQKPDGTVKLLIYHTSRLHSGV
PSRFSGSGSGTDYSLTISNLEQEDIATYFCQQGNTLPYTFGGGTKLEITKAGGGGSG
GGGSGGGGSGGGGSEVKLQESGPGLVAPSQSLSVTCTVSGVSLPDYGVSWIRQP
PRKGLEWLGVIWGSETTYYNSALKSRLTIIKDNSKSQVFLKMNSLQTDDTAIYYCAKH
YYYGGSYAMDYWGQGTSVTVSSDPTTTPAPRPPTPAPTIASQPLSLRPEACRPAAG
GAVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDV
```

LDKRRGRDPEMGGKPRRKNPQEGLYNELQKDKMAEAYSEIGMKGERRRGKGHDG

LYQGLSTATKDTYDALHMQALPPR

SEQ ID NO: 10
(TIP - Linker - dZap70SH2 - linker - TEV - 2a - Truncated CD22 -
CD19TM - Tyro-1 endodomain - Linker - TetRB - 2A - aCD19 - linker -
TEV cleavage site × 3 - GOFSTAT5(S710F))

MWTWNAYAFAAPSGGGSMPDPAAHLPFFYGSISRAEAEEEHLKLAGMADGLFLLRQ

CLRSLGGYVLSLVHDVRFHHFPIERQLNGTYAIAGGKAHCGPAELCEFYSRDPDGLP

CNLRKPCNRPSGLEPQPGVFDCLRDAMVRDYVRQTWKLEGEALEQAIISQAPQVEK

LIATTAHERMPWYHSSLTREEAERKLYSGAQTDGKFLLRPRKEQGTYALSLIYGKTV

YHYLISQDKAGKYCIPEGTKFDTLWQLVEYLKLKADGLIYCLKEACPNSSASNASGA

AAPTLPAHPSTLTHPSGGGGSSLFKGPRDYNPISSTICHLTNESDGHTTSLYGIGFG

PFIITNKHLFRRNNGTLLVQSLHGVFKVKNTTTLQQHLIDGRDMIIIRMPKDFPPFPQK

LKFREPQREERICLVTTNFQTKSMSSMVSDTSCTFPSSDGIFWKHWIQTKDGQCGS

PLVSTRDGFIVGIHSASNFTNTNNYFTSVPKNFMELLTNQEAQQWVSGWRLNADSV

LWGGHKVFMSKPEEPFQPVKEATQLMNELVYSQEGRGSLLTCGDVEENPGPMET

DTLLLWVLLLWVPGSTGDSSGKPIPNPLLGLDSSGGGSAPRDVRVRKIKPLSEIHSG

NSVSLQCDFSSSHPKEVQFFWEKNGRLLGKESQLNFDSISPEDAGSYSCWVNNSIG

QTASKAWTLEVLYAPRRLRVSMSPGDQVMEGKSATLTCESDANPPVSHYTWFDW

NNQSLPYHSQKLRLEPVKVQHSGAYWCQGTNSVGKGRSPLSTLTVYYSPETIGRR

AVTLAYLIFCLCSLVGILHLRARRSMDEANQPLLTDQYQCYAEEYEKLQNPNQSVV

GGSGGSMSRLDKSKVINSALELLNEVGIEGLTTRKLAQKLGVEQPTLYWHVKNKRAL

LDALAIEMLDRHHTHFCPLEGESWQDFLRNNAKSFRCALLSHRDGAKVHLGTRPTE

KQYETLENQLAFLCQQGFSLENALYALSAVGHFTLGCVLEDQEHQVAKEERETPTT

DSMPPLLRQAIELFDHQGAEPAFLFGLELIICGLEKQLKCESGSEGRGSLLTCGDVEE

NPGPMETDTLLLWVLLLWVPGSTGDIQMTQTTSSLSASLGDRVTISCRASQDISKYL

NWYQQKPDGTVKLLIYHTSRLHSGVPSRFSGSGSGTDYSLTISNLEQEDIATYFCQQ

GNTLPYTFGGGTKLEITKAGGGGSGGGGSGGGGSGGGGSEVKLQESGPGLVAPS

QSLSVTCTVSGVSLPDYGVSWIRQPPRKGLEWLGVIWGSETTYYNSALKSRLTIIKD

NSKSQVFLKMNSLQTDDTAIYYCAKHYYYGGSYAMDYWGQGTSVTVSSDPTTTPA

PRPPTPAPTIASQPLSLRPEACRPAAGGAVHTRGLDFACDIYIWAPLAGTCGVLLLSL

VITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPRGGSG

GSENLYFQGENLYFQGENLYFQGENLYFQGENLYFQGENLYFQGENLYFQGENLY

FQGENLYFQGMAGWIQAQQLQGDALRQMQVLYGQHFPIEVRHYLAQWIESQPWD

AIDLDNPQDRAQATQLLEGLVQELQKKAEHQVGEDGFLLKIKLGHYATQLQKTYDRC

PLELVRCIRHILYNEQRLVREANNCSSPAGILVDAMSQKHLQINQTFEELRLVTQDTE

NELKKLQQTQEYFIIQYQESLRIQAFQAQLSPQERLSRETALQQKQVSLEAWLQ

REAQTLQQYRVELAEKHQKTLQLLRKQQTIILDDELIQWKRRQQLAGNGGPPEGSL

DVLQSWCEKLAEIIWQNRQQIRRAEHLCQQLPIPGPVEEMLAEVNATITDIISALVTST

FIIEKQPPQVLKTQTKFAATVRLLVGGKLNVHMNPPQVKATIISEQQAKSLLKNENTR

-continued

NECSGEILNNCCVMEYHQATGTLSAHFRNMSLKRIKRADRRGAESVTEEKFTVLFE

SQFSVGSNELVFQVKTLSLPVVVIVHGSQDHNATATVLWDNAFAEPGRVPFAVPDK

VLWPQLCEALNMKFKAEVQSNRGLTKENLVFLAQKLFNNSSSHLEDYSGLSVSWS

QFNRENLPGWNYTFWQWFDGVMEVLKKHHKPHWNDGAILGFVNKQQAHDLLINK

PDGTFLLRFSDSEIGGITIAWKFDSPERNLWNLKPFTTRDFSIRSLADRLGDLSYLIYV

FPDRPKDEVFSKYYTPVLAKAVDGYVKPQIKQVVPEFVNAFADAGGSSATYMDQAP

SPAVCPQAPYNMYPQNPDHVLDQDGEFDLDETMDVARHVEELLRRPMDSLDSRLS

PPAGLFTSARGSLS

The inducible STAT constructs tested comprise the following amino acid sequence:
SEQ ID NO: 11
(FRB - linker - STAT5 - 2a - FKBP12 - linker - STAT3)
ILWHEMWHEGLEEASRLYFGERNVKGMFEVLEPLHAMMERGPQTLKETSFNQAYG

RDLMEAQEWCRKYMKSGNVKDLLQAWDLYYHVFRRISKSGGGGSGGGGSGGGG

SMAGWIQAQQLQGDALRQMQVLYGQHFPIEVRHYLAQWIESQPWDAIDLDN QDR

AQATQLLEGLVQELQKKAEHQVGEDGFLLKIKLGHYATQLQKTYDRCPLELVRCIRHI

LYNEQRLVREANNCSSPAGILVDAMSQKHLQINQTFEELRLVTQDTENELKKLQQTQ

EYFIIQYQESLRIQAFAQLAQLSPQERLSRETALQQKQVSLEAWLQREAQTLQQYR

VELAEKHQKTLQLLRKQQTIILDDELIQWKRRQQLAGNGGPPEGSLDVLQSWCEKL

AEIIWQNRQQIRRAEHLCQQLPIPGPVEEMLAEVNATITDIISALVTSTFIIEKQPPQVL

KTQTKFAATVRLLVGGKLNVHMNPPQVKATIISEQQAKSLLKNENTRNECSGEILNN

CCVMEYHQATGTLSAHFRNMSLKRIKRADRRGAESVTEEKFTVLFESQFSVGSNEL

VFQVKTLSLPVVVIVHGSQDHNATATVLWDNAFAEPGRVPFAVPDKVLWPQLCEAL

NMKFKAEVQSNRGLTKENLVFLAQKLFNNSSSHLEDYSGLSVSWSQFNRENLPGW

NYTFWQWFDGVMEVLKKHHKPHWNDGAILGFVNKQQAHDLLINKPDGTFLLRFSD

SEIGGITIAWKFDSPERNLWNLKPFTTRDFSIRSLADRLGDLSYLIYVFPDRPKDEVFS

KYYTPVLAKAVDGYVKPQIKQVVPEFVNASADAGGSSATYMDQAPSPAVCPQAPYN

MYPQNPDHVLDQDGEFDLDETMDVARHVEELLRRPMDSLDSRLSPPAGLFTSARG

SLSEGRGSLLTCGDVEENPGPGVQVETISPGDGRTFPKRGQTCVVHYTGMLEDGK

KVDSSRDRNKPFKFMLGKQEVIRGWEEGVAQMSVGQRAKLTISPDYAYGATGHPGI

IPPHATLVFDVELLKLESGGGGSGGGGSGGGGSAQWNQLQQLDTRYLEQLHQLYS

DSFPMELRQFLAPWIESQDWAYAASKESHATLVFHNLLGEIDQQYSRFLQESNVLY

QHNLRRIKQFLQSRYLEKPMEIARIVARCLWEESRLLQTAATAAQQGGQANHPTAA

VVTEKQQMLEQHLQDVRKRVQDLEQKMKVVENLQDDFDFNYKTLKSQGDMQDLN

GNNQSVTRQKMQQLEQMLTALDQMRRSIVSELAGLLSAMEYVQKTLTDEELADWK

RRQQIACIGGPPNICLDRLENWITSLAESQLQTRQQIKKLEELQQKVSYKGDPIVQHR

PMLEERIVELFRNLMKSAFVVERQPCMPMHPDRPLVIKTGVQFTTKVRLLVKFPELN

YQLKIKVCIDKSGDVAALRGSRKFNILGTNTKVMNMEESNNGSLSAEFKHLTLREQ

RCGNGGRANCDASLIVTEELHLITFETEVYHQGLKIDLETHSLPVVVISNICQMPNAW

ASILWYNMLTNNPKNVNFFTKPPIGTWDQVAEVLSWQFSSTTKRGLSIEQLTTLAEK

LLGPGVNYSGCQITWAKFCKENMAGKGFSFWVWLDNIIDLVKKYILALWNEGYIMGF

ISKERERAILSTKPPGTFLLRFSESSKEGGVTFTWVEKDISGKTQIQSVEPYTKQQLN

-continued

NMSFAEIIMGYKIMDATNILVSPLVYLYPDIPKEEAFGKYCRPESQEHPEADPGSAAP

YLKTKFICVTPTTCSNTIDLPMSPRTLDSLMQFGNNGEGAEPSAGGQFESLTFDMEL

TSECATSPM

SEQ ID NO: 12

(TIP - linker - STAT5 - 2a - TetRB - linker - STAT3)
MWTWNAYAFAAPSGGGGSGGGGSGGGGSMAGWIQAQQLQGDALRQMQVLYGQ

HFPIEVRHYLAQWIESQPWDAIDLDNPQDRAQATQLLEGLVQELQKKAEHQVGEDG

FLLKIKLGHYATQLQKTYDRCPLELVRCIRHILYNEQRLVREANNCSSPAGILVDAMS

QKHLQINQTFEELRLVTQDTENELKKLQQTQEYFIIQYQESLRIQAQFAQLAQLSPQE

RLSRETALQQKQVSLEAWLQREAQTLQQYRVELAEKHQKTLQLLRKQQTIILDDELI

QWKRRQQLAGNGGPPEGSLDVLQSWCEKLAEIIWQNRQQIRRAEHLCQQLPIPGP

VEEMLAEVNATITDIISALVTSTFIIEKQPPQVLKTQTKFAATVRLLVGGKLNVHMNPP

QVKATIISEQQAKSLLKNENTRNECSGEILNNCCVMEYHQATGTLSAHFRNMSLKRI

KRADRRGAESVTEEKFTVLFESQFSVGSNELVFQVKTLSLPVVVIVHGSQDHNATAT

VLWDNAFAEPGRVPFAVPDKVLWPQLCEALNMKFKAEVQSNRGLTKENLVFLAQKL

FNNSSSHLEDYSGLSVSWSQFNRENLPGWNYTFWQWFDGVMEVLKKHHKPHWN

DGAILGFVNKQQAHDLLINKPDGTFLLRFSDSEIGGITIAWKFDSPERNLWNLKPFTT

RDFSIRSLADRLGDLSYLIYVFPDRPKDEVFSKYYTPVLAKAVDGYVKPQIKQVVPEF

VNASADAGGSSATYMDQAPSPAVCPQAPYNMYPQNPDHVLDQDGEFDLDETMDV

ARHVEELLRRPMDSLDSRLSPPAGLFTSARGSLSEGRGSLLTCGDVEENPGPMSRL

DKSKVINSALELLNEVGIEGLTTRKLAQKLGVEQPTLYWHVKNKRALLDALAIEMLDR

HHTHFCPLEGESWQDFLRNNAKSFRCALLSHRDGAKVHLGTRPTEKQYETLENQL

AFLCQQGFSLENALYALSAVGHFTLGCVLEDQEHQVAKEERETPTTDSMPPLLRQAI

ELFDHQGAEPAFLFGLELIICGLEKQLKCESGSSGGGGSGGGGSGGGGSAQWNQL

QQLDTRYLEQLHQLYSDSFPMELRQFLAPWIESQDWAYAASKESHATLVFHNLLGEI

DQQYSRFLQESNVLYQHNLRRIKQFLQSRYLEKPMEIARIVARCLWEESRLLQTAAT

AAQQGGQANHPTAAVVTEKQQMLEQHLQDVRKRVQDLEQKMKVVENLQDDFDFN

YKTLKSQGDMQDLNGNNQSVTRQKMQQLEQMLTALDQMRRSIVSELAGLLSAMEY

VQKTLTDEELADWKRRQQIACIGGPPNICLDRLENWITSLAESQLQTRQQIKKLEELQ

QKVSYKGDPIVQHRPMLEERIVELFRNLMKSAFVVERQPCMPMHPDRPLVIKTGVQ

FTTKVRLLVKFPELNYQLKIKVCIDKDSGDVAALRGSRKFNILGTNTKVMNMEESNN

GSLSAEFKHLTLREQRCGNGGRANCDASLIVTEELHLITFETEVYHQGLKIDLETHSL

PVVVISNICQMPNAWASILWYNMLTNNPKNVNFFTKPPIGTWDQVAEVLSWQFSST

TKRGLSIEQLTTLAEKLLGPGVNYSGCQITWAKFCKENMAGKGFSFWVWLDNIIDLV

KKYILALWNEGYIMGFISKERERAILSTKPPGTFLLRFSESSKEGGVTFTWVEKDISG

KTQIQSVEPYTKQQLNNMSFAEIIMGYKIMDATNILVSPLVYLYPDIPKEEAFGKYCRP

ESQEHPEADPGSAAPYLKTKFICVTPTTCSNTIDLPMSPRTLDSLMQFGNNGEGAEP

SAGGQFESLTFDMELTSECATSPM

The process is repeated with several rounds of stimulation and assessed until there are not enough CAR T-cells to proceed due to a lack of proliferation or T-cell death. Proliferation of T cells and T-cell death is determined using T-cell counts and stains for apoptosis and necrosis (e.g. AnnexinIV and 7AAD).

The same constructs used in in vitro testing are used to test function in vivo with an additional construct transduced into the CAR T cells encoding for firefly luciferase to visualise the CAR T cell population in situ.

In vivo assays comprise of standard immune competent mouse models where tumour is orthotopically or subcutaneously injected and the ability for T-cells to eliminate the tumour is assessed over a period of two to ten weeks. GL261 cell lines are transduced to express the cognate ligand human CD19 and then intracranially injected into C57Bl/6 mice. On day 11 post tumour implantation, mice received 5Gy total body irradiation followed by an intravenous injection of CAR T cells.

FIGS. 7, 8, 9, 10, 11 and 12 provide annotated sequences of SEQ ID Nos 7, 8, 9, 10, 11 and 12, respectively.

Example 4: Assessment of the Propensity to Proliferate of Cells Expressing a Constitutively Active STAT Molecule in the Absence of Stimulation Measured by CTV Dilution A 96-hour starvation assay was set up comprising of peripheral blood mononuclear cells (PBMCs) labelled with cell trace violet (CTV). Cells were cultured in complete media in the absence of stimulation and exogenous cytokines (IL2). The cells were then analysed by flow cytometry on day 4, and the CTV mean fluorescence intensity (MFI) value calculated (gated on singlet, CD3+, live cells). When cells were transduced with a STAT encoding construct, the value of the MFI was gated on the transduced population. The CTV MFI is inversely proportional to the number of cellular divisions. The control (mock) refers to the total CD3 population from non-transduced PBMCs.

The constitutively active STAT molecule tested (STAT5beta_R659C gain of function mutation) demonstrated decreased CTV dilution values compared to the wild type constructs (STAT5beta_WT) which demonstrates that this mutant has increased propensity to proliferate compared to the wild type constructs (FIG. 13).

Example 5: Assessment of Intracellular Phosphorylated STAT5beta of Cells Expressing Constitutively Active STAT Mutants Constructs Compared to Wild Type A 72-hour starvation assay was set up to analyse intracellular staining for phosphorylated STAT5 (pSTAT5_Y694). Cells were cultured in complete media in the absence of stimulation and exogenous cytokines for 3 days. Afterwards, the cells were fixed and permeabilized and stained with the pSTAT5_Y694 antibody in accordance to BD Pharmingen phospho-FLOW protocol.

The cells were then analysed by flow cytometry and the pSTAT5 value was calculated (gated on singlet, CD3+, live cells).

Both the STAT5beta_T628S and the STAT5beta1704F gain of function (GOF) mutations showed a greater area under the curve in the histograms of FIGS. 14 (*a*) and (*b*), respectively, compared to the wild type STAT5beta constructs or controls.

Example 6: Assessment of the Capacity of Cells Expressing Constitutively Active STAT5 Mutants to Induce STAT5 Dependent Gene Expression A STAT5 responsive GFP reporter cell line was generated by transducing 293T cells with a self-inactivating vector construct. The vector comprised of three STAT5 DNA responsive elements controlling the expression of GFP followed by a constitutively active PGK promoter and a marker of transduction Q8 (doi.org/10.1182). The reporter cell line was transfected with the constructs encoding STAT and JAK mutants and GFP expression assessed 3 days later via flow cytometry.

FIGS. 15(*a*) and (*b*) both show an increase in GFP expression for the constitutively activate JAK2 and STAT5beta constructs (GOF mutants), respectively, compared to the corresponding wild type constructs.

The dotted horizontal lines on each on the bar graphs of FIGS. 15(*a*) and 15(*b*) represent background expression.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

The invention claimed is:

1. An engineered cell which comprises a CAR and a constitutively active Signal Transducer and Activator of Transcription (STAT) molecule,
   wherein the constitutively active STAT molecule is
   (a) a dimerized and constitutively active STAT molecule comprising a first STAT polypeptide having a first dimerization domain and a second STAT polypeptide having a second dimerization domain which second dimerization domain specifically binds the first dimerization domain and wherein the dimerization of the first and second STAT polypeptides structurally changes the STAT molecule to a constitutively active form,
   (b) a constitutively active STAT molecule comprising a first STAT polypeptide linked to a second STAT polypeptide by a linker sequence, or
   (c) a constitutively active STAT molecule comprising a Gain of Function (GOF) mutation.

2. A cell according to claim 1(b).

3. A cell according to claim 1(a).

4. A nucleotide construct comprising a first nucleotide sequence encoding a CAR and a second nucleotide sequence encoding a constitutively active STAT molecule,
   wherein the constitutively active STAT molecule is
   (a) a dimerized and constitutively active STAT molecule comprising a first STAT polypeptide having a first dimerization domain and a second STAT polypeptide having a second dimerization domain which second dimerization domain specifically binds the first dimerization domain and wherein the dimerization of the first and second STAT polypeptides structurally changes the STAT molecule to a constitutively active form,
   (b) a constitutively active STAT molecule comprising a first STAT polypeptide linked to a second STAT polypeptide by a linker sequence, or
   (c) a constitutively active STAT molecule comprising a Gain of Function (GOF) mutation.

5. A pharmaceutical composition comprising a plurality of cells according to claim 1.

6. A method for making a cell according to claim 1, which comprises the step of introducing into a cell a nucleic acid sequence encoding the constitutively active or inducible STAT molecule.

7. A cell according to claim 1(c).

* * * * *

SEQUENCE LISTING

```
<160> NUMBER OF SEQ ID NOS: 14

<210> SEQ ID NO 1
<211> LENGTH: 29
<212> TYPE: PRT
<213> ORGANISM: Artificial Sequence
<220> FEATURE:
<223> OTHER INFORMATION: first dimerization domain sequence

<400> SEQUENCE: 1

Gln Leu Glu Lys Glu Leu Gln Ala Leu Glu Lys Glu Asn Ala Gln Leu
1               5                   10                  15

Glu Trp Glu Leu Gln Ala Leu Glu Lys Glu Leu Ala Gln
            20                  25

<210> SEQ ID NO 2
```

```
<211> LENGTH: 29
<212> TYPE: PRT
<213> ORGANISM: Artificial Sequence
<220> FEATURE:
<223> OTHER INFORMATION: second dimerization domain sequence

<400> SEQUENCE: 2

Gln Leu Glu Lys Lys Leu Gln Ala Leu Lys Lys Asn Ala Gln Leu
1               5                   10                  15

Lys Trp Lys Leu Gln Ala Leu Lys Lys Lys Leu Ala Gln
            20                  25

<210> SEQ ID NO 3
<211> LENGTH: 4
<212> TYPE: PRT
<213> ORGANISM: Artificial Sequence
<220> FEATURE:
<223> OTHER INFORMATION: linker sequence

<400> SEQUENCE: 3

Gly Gly Ser Gly
1

<210> SEQ ID NO 4
<211> LENGTH: 6
<212> TYPE: PRT
<213> ORGANISM: Artificial Sequence
<220> FEATURE:
<223> OTHER INFORMATION: linker sequence

<400> SEQUENCE: 4

Gly Ser Gly Ser Gly Ser
1               5

<210> SEQ ID NO 5
<211> LENGTH: 8
<212> TYPE: PRT
<213> ORGANISM: Artificial Sequence
<220> FEATURE:
<223> OTHER INFORMATION: linker sequence

<400> SEQUENCE: 5

Gly Gly Ser Gly Gly Gly Ser Gly
1               5

<210> SEQ ID NO 6
<211> LENGTH: 9
<212> TYPE: PRT
<213> ORGANISM: Artificial Sequence
<220> FEATURE:
<223> OTHER INFORMATION: linker sequence

<400> SEQUENCE: 6

Ser Gly Gly Ser Gly Gly Ser Gly Gly
1               5

<210> SEQ ID NO 7
<211> LENGTH: 1590
<212> TYPE: PRT
<213> ORGANISM: Artificial Sequence
<220> FEATURE:
<223> OTHER INFORMATION: constitutively active Signal Transducer and
      Activator of Transcription (STAT) construct (STAT3 - Linker -
      STAT5)

<400> SEQUENCE: 7

Met Ala Gln Trp Asn Gln Leu Gln Gln Leu Asp Thr Arg Tyr Leu Glu
```

-continued

```
1               5                   10                  15
Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
                35                  40                  45

Lys Glu Ser His Ala Thr Leu Val Phe His Asn Leu Leu Gly Glu Ile
                50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
                115                 120                 125

Ala Asn His Pro Thr Ala Ala Val Val Thr Glu Lys Gln Gln Met Leu
                130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
                180                 185                 190

Gln Ser Val Thr Arg Gln Lys Met Gln Gln Leu Glu Gln Met Leu Thr
                195                 200                 205

Ala Leu Asp Gln Met Arg Arg Ser Ile Val Ser Glu Leu Ala Gly Leu
                210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Gln Ile Lys Lys Leu Glu Glu Leu Gln
                275                 280                 285

Gln Lys Val Ser Tyr Lys Gly Asp Pro Ile Val Gln His Arg Pro Met
                290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
                355                 360                 365

Asp Lys Asp Ser Gly Asp Val Ala Ala Leu Arg Gly Ser Arg Lys Phe
                370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430
```

```
Thr Glu Glu Leu His Leu Ile Thr Phe Glu Thr Val Tyr His Gln
            435                 440                 445

Gly Leu Lys Ile Asp Leu Glu Thr His Ser Leu Pro Val Val Ile
        450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
        530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
        690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met Ser Gly Gly Gly Ser Gly Gly Gly Ser Gly Gly Gly
770                 775                 780

Gly Ser Gly Gly Gly Ser Gly Gly Gly Ser Met Ala Gly Trp
785                 790                 795                 800

Ile Gln Ala Gln Gln Leu Gln Gly Asp Ala Leu Arg Gln Met Gln Val
                805                 810                 815

Leu Tyr Gly Gln His Phe Pro Ile Glu Val Arg His Tyr Leu Ala Gln
            820                 825                 830

Trp Ile Glu Ser Gln Pro Trp Asp Ala Ile Asp Leu Asp Asn Pro Gln
        835                 840                 845
```

```
Asp Arg Ala Gln Ala Thr Gln Leu Leu Glu Gly Leu Val Gln Glu Leu
850                 855                 860

Gln Lys Lys Ala Glu His Gln Val Gly Glu Asp Gly Phe Leu Leu Lys
865                 870                 875                 880

Ile Lys Leu Gly His Tyr Ala Thr Gln Leu Gln Lys Thr Tyr Asp Arg
                    885                 890                 895

Cys Pro Leu Glu Leu Val Arg Cys Ile Arg His Ile Leu Tyr Asn Glu
                900                 905                 910

Gln Arg Leu Val Arg Glu Ala Asn Asn Cys Ser Ser Pro Ala Gly Ile
            915                 920                 925

Leu Val Asp Ala Met Ser Gln Lys His Leu Gln Ile Asn Gln Thr Phe
930                 935                 940

Glu Glu Leu Arg Leu Val Thr Gln Asp Thr Glu Asn Glu Leu Lys Lys
945                 950                 955                 960

Leu Gln Gln Thr Gln Glu Tyr Phe Ile Ile Gln Tyr Gln Glu Ser Leu
                965                 970                 975

Arg Ile Gln Ala Gln Phe Ala Gln Leu Ala Gln Leu Ser Pro Gln Glu
            980                 985                 990

Arg Leu Ser Arg Glu Thr Ala Leu  Gln Gln Lys Gln Val  Ser Leu Glu
            995                 1000                1005

Ala Trp  Leu Gln Arg Glu Ala  Gln Thr Leu Gln Gln  Tyr Arg Val
1010                1015                1020

Glu Leu  Ala Glu Lys His Gln  Lys Thr Leu Gln Leu  Leu Arg Lys
1025                1030                1035

Gln Gln  Thr Ile Ile Leu Asp  Asp Glu Leu Ile Gln  Trp Lys Arg
1040                1045                1050

Arg Gln  Gln Leu Ala Gly Asn  Gly Gly Pro Pro Glu  Gly Ser Leu
1055                1060                1065

Asp Val  Leu Gln Ser Trp Cys  Glu Lys Leu Ala Glu  Ile Ile Trp
1070                1075                1080

Gln Asn  Arg Gln Gln Ile Arg  Arg Ala Glu His Leu  Cys Gln Gln
1085                1090                1095

Leu Pro  Ile Pro Gly Pro Val  Glu Glu Met Leu Ala  Glu Val Asn
1100                1105                1110

Ala Thr  Ile Thr Asp Ile Ile  Ser Ala Leu Val Thr  Ser Thr Phe
1115                1120                1125

Ile Ile  Glu Lys Gln Pro Pro  Gln Val Leu Lys Thr  Gln Thr Lys
1130                1135                1140

Phe Ala  Ala Thr Val Arg Leu  Leu Val Gly Gly Lys  Leu Asn Val
1145                1150                1155

His Met  Asn Pro Pro Gln Val  Lys Ala Thr Ile Ile  Ser Glu Gln
1160                1165                1170

Gln Ala  Lys Ser Leu Leu Lys  Asn Glu Asn Thr Arg  Asn Glu Cys
1175                1180                1185

Ser Gly  Glu Ile Leu Asn Asn  Cys Cys Val Met Glu  Tyr His Gln
1190                1195                1200

Ala Thr  Gly Thr Leu Ser Ala  His Phe Arg Asn Met  Ser Leu Lys
1205                1210                1215

Arg Ile  Lys Arg Ala Asp Arg  Arg Gly Ala Glu Ser  Val Thr Glu
1220                1225                1230

Glu Lys  Phe Thr Val Leu Phe  Glu Ser Gln Phe Ser  Val Gly Ser
1235                1240                1245

Asn Glu  Leu Val Phe Gln Val  Lys Thr Leu Ser Leu  Pro Val Val
```

Val Ile Val His Gly Ser Gln Asp His Asn Ala Thr Ala Thr Val
1265                1270                1275

Leu Trp Asp Asn Ala Phe Ala Glu Pro Gly Arg Val Pro Phe Ala
         1280                1285                1290

Val Pro Asp Lys Val Leu Trp Pro Gln Leu Cys Glu Ala Leu Asn
    1295                1300                1305

Met Lys Phe Lys Ala Glu Val Gln Ser Asn Arg Gly Leu Thr Lys
1310                1315                1320

Glu Asn Leu Val Phe Leu Ala Gln Lys Leu Phe Asn Asn Ser Ser
    1325                1330                1335

Ser His Leu Glu Asp Tyr Ser Gly Leu Ser Val Ser Trp Ser Gln
1340                1345                1350

Phe Asn Arg Glu Asn Leu Pro Gly Trp Asn Tyr Thr Phe Trp Gln
    1355                1360                1365

Trp Phe Asp Gly Val Met Glu Val Leu Lys Lys His His Lys Pro
1370                1375                1380

His Trp Asn Asp Gly Ala Ile Leu Gly Phe Val Asn Lys Gln Gln
    1385                1390                1395

Ala His Asp Leu Leu Ile Asn Lys Pro Asp Gly Thr Phe Leu Leu
1400                1405                1410

Arg Phe Ser Asp Ser Glu Ile Gly Gly Ile Thr Ile Ala Trp Lys
    1415                1420                1425

Phe Asp Ser Pro Glu Arg Asn Leu Trp Asn Leu Lys Pro Phe Thr
1430                1435                1440

Thr Arg Asp Phe Ser Ile Arg Ser Leu Ala Asp Arg Leu Gly Asp
    1445                1450                1455

Leu Ser Tyr Leu Ile Tyr Val Phe Pro Asp Arg Pro Lys Asp Glu
1460                1465                1470

Val Phe Ser Lys Tyr Tyr Thr Pro Val Leu Ala Lys Ala Val Asp
    1475                1480                1485

Gly Tyr Val Lys Pro Gln Ile Lys Gln Val Val Pro Glu Phe Val
1490                1495                1500

Asn Ala Ser Ala Asp Ala Gly Gly Ser Ser Ala Thr Tyr Met Asp
    1505                1510                1515

Gln Ala Pro Ser Pro Ala Val Cys Pro Gln Ala Pro Tyr Asn Met
1520                1525                1530

Tyr Pro Gln Asn Pro Asp His Val Leu Asp Gln Asp Gly Glu Phe
    1535                1540                1545

Asp Leu Asp Glu Thr Met Asp Val Ala Arg His Val Glu Glu Leu
1550                1555                1560

Leu Arg Arg Pro Met Asp Ser Leu Asp Ser Arg Leu Ser Pro Pro
    1565                1570                1575

Ala Gly Leu Phe Thr Ser Ala Arg Gly Ser Leu Ser
1580                1585                1590

<210> SEQ ID NO 8
<211> LENGTH: 1896
<212> TYPE: PRT
<213> ORGANISM: Artificial Sequence
<220> FEATURE:
<223> OTHER INFORMATION: constitutively active STAT construct (TIP -
      STAT3 - Linker - STAT5 - 2a - Myristoylation and palmitoylation
      sequence - Ridge Linker - TetRB)

<400> SEQUENCE: 8

```
Met Trp Thr Trp Asn Ala Tyr Ala Phe Ala Ala Pro Ser Gly Gly Gly
1               5                   10                  15

Ser Ala Gln Trp Asn Gln Leu Gln Gln Leu Asp Thr Arg Tyr Leu Glu
            20                  25                  30

Gln Leu His Gln Leu Tyr Ser Asp Ser Phe Pro Met Glu Leu Arg Gln
        35                  40                  45

Phe Leu Ala Pro Trp Ile Glu Ser Gln Asp Trp Ala Tyr Ala Ala Ser
    50                  55                  60

Lys Glu Ser His Ala Thr Leu Val Phe His Asn Leu Leu Gly Glu Ile
65                  70                  75                  80

Asp Gln Gln Tyr Ser Arg Phe Leu Gln Glu Ser Asn Val Leu Tyr Gln
                85                  90                  95

His Asn Leu Arg Arg Ile Lys Gln Phe Leu Gln Ser Arg Tyr Leu Glu
            100                 105                 110

Lys Pro Met Glu Ile Ala Arg Ile Val Ala Arg Cys Leu Trp Glu Glu
        115                 120                 125

Ser Arg Leu Leu Gln Thr Ala Ala Thr Ala Ala Gln Gln Gly Gly Gln
    130                 135                 140

Ala Asn His Pro Thr Ala Ala Val Val Thr Glu Lys Gln Gln Met Leu
145                 150                 155                 160

Glu Gln His Leu Gln Asp Val Arg Lys Arg Val Gln Asp Leu Glu Gln
                165                 170                 175

Lys Met Lys Val Val Glu Asn Leu Gln Asp Asp Phe Asp Phe Asn Tyr
            180                 185                 190

Lys Thr Leu Lys Ser Gln Gly Asp Met Gln Asp Leu Asn Gly Asn Asn
        195                 200                 205

Gln Ser Val Thr Arg Gln Lys Met Gln Gln Leu Glu Gln Met Leu Thr
    210                 215                 220

Ala Leu Asp Gln Met Arg Arg Ser Ile Val Ser Glu Leu Ala Gly Leu
225                 230                 235                 240

Leu Ser Ala Met Glu Tyr Val Gln Lys Thr Leu Thr Asp Glu Glu Leu
                245                 250                 255

Ala Asp Trp Lys Arg Arg Gln Gln Ile Ala Cys Ile Gly Gly Pro Pro
            260                 265                 270

Asn Ile Cys Leu Asp Arg Leu Glu Asn Trp Ile Thr Ser Leu Ala Glu
        275                 280                 285

Ser Gln Leu Gln Thr Arg Gln Gln Ile Lys Lys Leu Glu Glu Leu Gln
    290                 295                 300

Gln Lys Val Ser Tyr Lys Gly Asp Pro Ile Val Gln His Arg Pro Met
305                 310                 315                 320

Leu Glu Glu Arg Ile Val Glu Leu Phe Arg Asn Leu Met Lys Ser Ala
                325                 330                 335

Phe Val Val Glu Arg Gln Pro Cys Met Pro Met His Pro Asp Arg Pro
            340                 345                 350

Leu Val Ile Lys Thr Gly Val Gln Phe Thr Thr Lys Val Arg Leu Leu
        355                 360                 365

Val Lys Phe Pro Glu Leu Asn Tyr Gln Leu Lys Ile Lys Val Cys Ile
    370                 375                 380

Asp Lys Asp Ser Gly Asp Val Ala Ala Leu Arg Gly Ser Arg Lys Phe
385                 390                 395                 400

Asn Ile Leu Gly Thr Asn Thr Lys Val Met Asn Met Glu Glu Ser Asn
                405                 410                 415
```

```
Asn Gly Ser Leu Ser Ala Glu Phe Lys His Leu Thr Leu Arg Glu Gln
            420                 425                 430
Arg Cys Gly Asn Gly Arg Ala Asn Cys Asp Ala Ser Leu Ile Val
        435                 440                 445
Thr Glu Glu Leu His Leu Ile Thr Phe Glu Thr Glu Val Tyr His Gln
    450                 455                 460
Gly Leu Lys Ile Asp Leu Glu Thr His Ser Leu Pro Val Val Val Ile
465                 470                 475                 480
Ser Asn Ile Cys Gln Met Pro Asn Ala Trp Ala Ser Ile Leu Trp Tyr
                485                 490                 495
Asn Met Leu Thr Asn Asn Pro Lys Asn Val Asn Phe Phe Thr Lys Pro
            500                 505                 510
Pro Ile Gly Thr Trp Asp Gln Val Ala Glu Val Leu Ser Trp Gln Phe
        515                 520                 525
Ser Ser Thr Thr Lys Arg Gly Leu Ser Ile Glu Gln Leu Thr Thr Leu
    530                 535                 540
Ala Glu Lys Leu Leu Gly Pro Gly Val Asn Tyr Ser Gly Cys Gln Ile
545                 550                 555                 560
Thr Trp Ala Lys Phe Cys Lys Glu Asn Met Ala Gly Lys Gly Phe Ser
                565                 570                 575
Phe Trp Val Trp Leu Asp Asn Ile Ile Asp Leu Val Lys Lys Tyr Ile
            580                 585                 590
Leu Ala Leu Trp Asn Glu Gly Tyr Ile Met Gly Phe Ile Ser Lys Glu
        595                 600                 605
Arg Glu Arg Ala Ile Leu Ser Thr Lys Pro Pro Gly Thr Phe Leu Leu
    610                 615                 620
Arg Phe Ser Glu Ser Ser Lys Glu Gly Gly Val Thr Phe Thr Trp Val
625                 630                 635                 640
Glu Lys Asp Ile Ser Gly Lys Thr Gln Ile Gln Ser Val Glu Pro Tyr
                645                 650                 655
Thr Lys Gln Gln Leu Asn Asn Met Ser Phe Ala Glu Ile Ile Met Gly
            660                 665                 670
Tyr Lys Ile Met Asp Ala Thr Asn Ile Leu Val Ser Pro Leu Val Tyr
        675                 680                 685
Leu Tyr Pro Asp Ile Pro Lys Glu Glu Ala Phe Gly Lys Tyr Cys Arg
    690                 695                 700
Pro Glu Ser Gln Glu His Pro Glu Ala Asp Pro Gly Ser Ala Ala Pro
705                 710                 715                 720
Tyr Leu Lys Thr Lys Phe Ile Cys Val Thr Pro Thr Thr Cys Ser Asn
                725                 730                 735
Thr Ile Asp Leu Pro Met Ser Pro Arg Thr Leu Asp Ser Leu Met Gln
            740                 745                 750
Phe Gly Asn Asn Gly Glu Gly Ala Glu Pro Ser Ala Gly Gly Gln Phe
        755                 760                 765
Glu Ser Leu Thr Phe Asp Met Glu Leu Thr Ser Glu Cys Ala Thr Ser
    770                 775                 780
Pro Met Ser Gly Gly Gly Ser Gly Gly Gly Ser Gly Gly Gly
785                 790                 795                 800
Gly Ser Gly Gly Gly Gly Ser Gly Gly Gly Ser Met Ala Gly Trp
                805                 810                 815
Ile Gln Ala Gln Gln Leu Gln Gly Asp Ala Leu Arg Gln Met Gln Val
            820                 825                 830
Leu Tyr Gly Gln His Phe Pro Ile Glu Val Arg His Tyr Leu Ala Gln
```

-continued

```
                835                 840                 845
Trp Ile Glu Ser Gln Pro Trp Asp Ala Ile Asp Leu Asp Asn Pro Gln
            850                 855                 860
Asp Arg Ala Gln Ala Thr Gln Leu Leu Glu Gly Leu Val Gln Glu Leu
865                 870                 875                 880
Gln Lys Lys Ala Glu His Gln Val Gly Glu Asp Gly Phe Leu Leu Lys
                885                 890                 895
Ile Lys Leu Gly His Tyr Ala Thr Gln Leu Gln Lys Thr Tyr Asp Arg
            900                 905                 910
Cys Pro Leu Glu Leu Val Arg Cys Ile Arg His Ile Leu Tyr Asn Glu
            915                 920                 925
Gln Arg Leu Val Arg Glu Ala Asn Asn Cys Ser Ser Pro Ala Gly Ile
            930                 935                 940
Leu Val Asp Ala Met Ser Gln Lys His Leu Gln Ile Asn Gln Thr Phe
945                 950                 955                 960
Glu Glu Leu Arg Leu Val Thr Gln Asp Thr Glu Asn Glu Leu Lys Lys
                965                 970                 975
Leu Gln Gln Thr Gln Glu Tyr Phe Ile Ile Gln Tyr Gln Glu Ser Leu
            980                 985                 990
Arg Ile Gln Ala Gln Phe Ala Gln Leu Ala Gln Leu Ser Pro Gln Glu
            995                 1000                1005
Arg Leu Ser Arg Glu Thr Ala Leu Gln Gln Lys Gln Val Ser Leu
        1010                1015                1020
Glu Ala Trp Leu Gln Arg Glu Ala Gln Thr Leu Gln Gln Tyr Arg
        1025                1030                1035
Val Glu Leu Ala Glu Lys His Gln Lys Thr Leu Gln Leu Leu Arg
        1040                1045                1050
Lys Gln Gln Thr Ile Ile Leu Asp Asp Glu Leu Ile Gln Trp Lys
        1055                1060                1065
Arg Arg Gln Gln Leu Ala Gly Asn Gly Gly Pro Pro Glu Gly Ser
        1070                1075                1080
Leu Asp Val Leu Gln Ser Trp Cys Glu Lys Leu Ala Glu Ile Ile
        1085                1090                1095
Trp Gln Asn Arg Gln Gln Ile Arg Arg Ala Glu His Leu Cys Gln
        1100                1105                1110
Gln Leu Pro Ile Pro Gly Pro Val Glu Glu Met Leu Ala Glu Val
        1115                1120                1125
Asn Ala Thr Ile Thr Asp Ile Ile Ser Ala Leu Val Thr Ser Thr
        1130                1135                1140
Phe Ile Ile Glu Lys Gln Pro Pro Gln Val Leu Lys Thr Gln Thr
        1145                1150                1155
Lys Phe Ala Ala Thr Val Arg Leu Leu Val Gly Gly Lys Leu Asn
        1160                1165                1170
Val His Met Asn Pro Pro Gln Val Lys Ala Thr Ile Ile Ser Glu
        1175                1180                1185
Gln Gln Ala Lys Ser Leu Leu Lys Asn Glu Asn Thr Arg Asn Glu
        1190                1195                1200
Cys Ser Gly Glu Ile Leu Asn Asn Cys Cys Val Met Glu Tyr His
        1205                1210                1215
Gln Ala Thr Gly Thr Leu Ser Ala His Phe Arg Asn Met Ser Leu
        1220                1225                1230
Lys Arg Ile Lys Arg Ala Asp Arg Arg Gly Ala Glu Ser Val Thr
        1235                1240                1245
```

```
Glu Glu Lys Phe Thr Val Leu Phe Glu Ser Gln Phe Ser Val Gly
    1250                1255                1260

Ser Asn Glu Leu Val Phe Gln Val Lys Thr Leu Ser Leu Pro Val
    1265                1270                1275

Val Val Ile Val His Gly Ser Gln Asp His Asn Ala Thr Ala Thr
    1280                1285                1290

Val Leu Trp Asp Asn Ala Phe Ala Glu Pro Gly Arg Val Pro Phe
    1295                1300                1305

Ala Val Pro Asp Lys Val Leu Trp Pro Gln Leu Cys Glu Ala Leu
    1310                1315                1320

Asn Met Lys Phe Lys Ala Glu Val Gln Ser Asn Arg Gly Leu Thr
    1325                1330                1335

Lys Glu Asn Leu Val Phe Leu Ala Gln Lys Leu Phe Asn Asn Ser
    1340                1345                1350

Ser Ser His Leu Glu Asp Tyr Ser Gly Leu Ser Val Ser Trp Ser
    1355                1360                1365

Gln Phe Asn Arg Glu Asn Leu Pro Gly Trp Asn Tyr Thr Phe Trp
    1370                1375                1380

Gln Trp Phe Asp Gly Val Met Glu Val Leu Lys Lys His His Lys
    1385                1390                1395

Pro His Trp Asn Asp Gly Ala Ile Leu Gly Phe Val Asn Lys Gln
    1400                1405                1410

Gln Ala His Asp Leu Leu Ile Asn Lys Pro Asp Gly Thr Phe Leu
    1415                1420                1425

Leu Arg Phe Ser Asp Ser Glu Ile Gly Gly Ile Thr Ile Ala Trp
    1430                1435                1440

Lys Phe Asp Ser Pro Glu Arg Asn Leu Trp Asn Leu Lys Pro Phe
    1445                1450                1455

Thr Thr Arg Asp Phe Ser Ile Arg Ser Leu Ala Asp Arg Leu Gly
    1460                1465                1470

Asp Leu Ser Tyr Leu Ile Tyr Val Phe Pro Asp Arg Pro Lys Asp
    1475                1480                1485

Glu Val Phe Ser Lys Tyr Tyr Thr Pro Val Leu Ala Lys Ala Val
    1490                1495                1500

Asp Gly Tyr Val Lys Pro Gln Ile Lys Gln Val Val Pro Glu Phe
    1505                1510                1515

Val Asn Ala Ser Ala Asp Ala Gly Gly Ser Ser Ala Thr Tyr Met
    1520                1525                1530

Asp Gln Ala Pro Ser Pro Ala Val Cys Pro Gln Ala Pro Tyr Asn
    1535                1540                1545

Met Tyr Pro Gln Asn Pro Asp His Val Leu Asp Gln Asp Gly Glu
    1550                1555                1560

Phe Asp Leu Asp Glu Thr Met Asp Val Ala Arg His Val Glu Glu
    1565                1570                1575

Leu Leu Arg Arg Pro Met Asp Ser Leu Asp Ser Arg Leu Ser Pro
    1580                1585                1590

Pro Ala Gly Leu Phe Thr Ser Ala Arg Gly Ser Leu Ser Glu Gly
    1595                1600                1605

Arg Gly Ser Leu Leu Thr Cys Gly Asp Val Glu Glu Asn Pro Gly
    1610                1615                1620

Pro Met Gly Cys Gly Cys Ser Ser His Pro Glu Leu Glu Ala Glu
    1625                1630                1635
```

```
Ala Ala Ala Lys Glu Ala Ala Ala Lys Glu Ala Ala Ala Lys Glu
        1640                1645                1650

Ala Ala Ala Lys Ala Leu Glu Ala Glu Ala Ala Lys Glu Ala
        1655                1660                1665

Ala Ala Lys Glu Ala Ala Lys Glu Ala Ala Lys Ala Leu
        1670                1675                1680

Glu Ser Gly Gly Gly Ser Met Ser Arg Leu Asp Lys Ser Lys Val
        1685                1690                1695

Ile Asn Ser Ala Leu Glu Leu Leu Asn Glu Val Gly Ile Glu Gly
        1700                1705                1710

Leu Thr Thr Arg Lys Leu Ala Gln Lys Leu Gly Val Glu Gln Pro
        1715                1720                1725

Thr Leu Tyr Trp His Val Lys Asn Lys Arg Ala Leu Leu Asp Ala
        1730                1735                1740

Leu Ala Ile Glu Met Leu Asp Arg His His Thr His Phe Cys Pro
        1745                1750                1755

Leu Glu Gly Glu Ser Trp Gln Asp Phe Leu Arg Asn Asn Ala Lys
        1760                1765                1770

Ser Phe Arg Cys Ala Leu Leu Ser His Arg Asp Gly Ala Lys Val
        1775                1780                1785

His Leu Gly Thr Arg Pro Thr Glu Lys Gln Tyr Glu Thr Leu Glu
        1790                1795                1800

Asn Gln Leu Ala Phe Leu Cys Gln Gln Gly Phe Ser Leu Glu Asn
        1805                1810                1815

Ala Leu Tyr Ala Leu Ser Ala Val Gly His Phe Thr Leu Gly Cys
        1820                1825                1830

Val Leu Glu Asp Gln Glu His Gln Val Ala Lys Glu Glu Arg Glu
        1835                1840                1845

Thr Pro Thr Thr Asp Ser Met Pro Pro Leu Leu Arg Gln Ala Ile
        1850                1855                1860

Glu Leu Phe Asp His Gln Gly Ala Glu Pro Ala Phe Leu Phe Gly
        1865                1870                1875

Leu Glu Leu Ile Ile Cys Gly Leu Glu Lys Gln Leu Lys Cys Glu
        1880                1885                1890

Ser Gly Ser
        1895

<210> SEQ ID NO 9
<211> LENGTH: 2729
<212> TYPE: PRT
<213> ORGANISM: Artificial Sequence
<220> FEATURE:
<223> OTHER INFORMATION: constitutively active STAT construct (SH2
      ZAP70 - Linker - TEV - 2a - myristoylation and palmitoylation
      sequence - linker - TEV cleavage site x3 - STAT3 - Linker -STAT5 -
      2a - aCD19)

<400> SEQUENCE: 9

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
        50                  55                  60
```

Leu Asn Gly Thr Tyr Ala Ile Ala Gly Gly Lys Ala His Cys Gly Pro
65              70                  75                  80

Ala Glu Leu Cys Glu Phe Tyr Ser Arg Asp Pro Asp Gly Leu Pro Cys
            85                  90                  95

Asn Leu Arg Lys Pro Cys Asn Arg Pro Ser Gly Leu Glu Pro Gln Pro
        100                 105                 110

Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
        130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Ser Gly Gly Gly Ser Ser Leu
        275                 280                 285

Phe Lys Gly Pro Arg Asp Tyr Asn Pro Ile Ser Ser Thr Ile Cys His
290                 295                 300

Leu Thr Asn Glu Ser Asp Gly His Thr Thr Ser Leu Tyr Gly Ile Gly
305                 310                 315                 320

Phe Gly Pro Phe Ile Ile Thr Asn Lys His Leu Phe Arg Arg Asn Asn
                325                 330                 335

Gly Thr Leu Leu Val Gln Ser Leu His Gly Val Phe Lys Val Lys Asn
            340                 345                 350

Thr Thr Thr Leu Gln Gln His Leu Ile Asp Gly Arg Asp Met Ile Ile
        355                 360                 365

Ile Arg Met Pro Lys Asp Phe Pro Pro Phe Pro Gln Lys Leu Lys Phe
        370                 375                 380

Arg Glu Pro Gln Arg Glu Glu Arg Ile Cys Leu Val Thr Thr Asn Phe
385                 390                 395                 400

Gln Thr Lys Ser Met Ser Ser Met Val Ser Asp Thr Ser Cys Thr Phe
                405                 410                 415

Pro Ser Ser Asp Gly Ile Phe Trp Lys His Trp Ile Gln Thr Lys Asp
            420                 425                 430

Gly Gln Cys Gly Ser Pro Leu Val Ser Thr Arg Asp Gly Phe Ile Val
        435                 440                 445

Gly Ile His Ser Ala Ser Asn Phe Thr Asn Thr Asn Asn Tyr Phe Thr
        450                 455                 460

Ser Val Pro Lys Asn Phe Met Glu Leu Leu Thr Asn Gln Glu Ala Gln
465                 470                 475                 480

Gln Trp Val Ser Gly Trp Arg Leu Asn Ala Asp Ser Val Leu Trp Gly

```
                485                 490                 495
Gly His Lys Val Phe Met Ser Lys Pro Glu Glu Pro Phe Gln Pro Val
                500                 505                 510

Lys Glu Ala Thr Gln Leu Met Asn Glu Leu Val Tyr Ser Gln Glu Gly
                515                 520                 525

Arg Gly Ser Leu Leu Thr Cys Gly Asp Val Glu Glu Asn Pro Gly Pro
                530                 535                 540

Met Gly Cys Gly Cys Ser Ser His Pro Glu Ser Gly Gly Gly Gly Ser
545                 550                 555                 560

Gly Gly Gly Gly Ser Glu Asn Leu Tyr Phe Gln Gly Glu Asn Leu Tyr
                565                 570                 575

Phe Gln Gly Glu Asn Leu Tyr Phe Gln Gly Glu Asn Leu Tyr Phe Gln
                580                 585                 590

Gly Glu Asn Leu Tyr Phe Gln Gly Glu Asn Leu Tyr Phe Gln Gly Glu
                595                 600                 605

Asn Leu Tyr Phe Gln Gly Glu Asn Leu Tyr Phe Gln Gly Glu Asn Leu
                610                 615                 620

Tyr Phe Gln Gly Ala Gln Trp Asn Gln Leu Gln Gln Leu Asp Thr Arg
625                 630                 635                 640

Tyr Leu Glu Gln Leu His Gln Leu Tyr Ser Asp Ser Phe Pro Met Glu
                645                 650                 655

Leu Arg Gln Phe Leu Ala Pro Trp Ile Glu Ser Gln Asp Trp Ala Tyr
                660                 665                 670

Ala Ala Ser Lys Glu Ser His Ala Thr Leu Val Phe His Asn Leu Leu
                675                 680                 685

Gly Glu Ile Asp Gln Gln Tyr Ser Arg Phe Leu Gln Glu Ser Asn Val
                690                 695                 700

Leu Tyr Gln His Asn Leu Arg Arg Ile Lys Gln Phe Leu Gln Ser Arg
705                 710                 715                 720

Tyr Leu Glu Lys Pro Met Glu Ile Ala Arg Ile Val Ala Arg Cys Leu
                725                 730                 735

Trp Glu Glu Ser Arg Leu Leu Gln Thr Ala Ala Thr Ala Ala Gln Gln
                740                 745                 750

Gly Gly Gln Ala Asn His Pro Thr Ala Ala Val Val Thr Glu Lys Gln
                755                 760                 765

Gln Met Leu Glu Gln His Leu Gln Asp Val Arg Lys Arg Val Gln Asp
                770                 775                 780

Leu Glu Gln Lys Met Lys Val Val Glu Asn Leu Gln Asp Asp Phe Asp
785                 790                 795                 800

Phe Asn Tyr Lys Thr Leu Lys Ser Gln Gly Asp Met Gln Asp Leu Asn
                805                 810                 815

Gly Asn Asn Gln Ser Val Thr Arg Gln Lys Met Gln Gln Leu Glu Gln
                820                 825                 830

Met Leu Thr Ala Leu Asp Gln Met Arg Arg Ser Ile Val Ser Glu Leu
                835                 840                 845

Ala Gly Leu Leu Ser Ala Met Glu Tyr Val Gln Lys Thr Leu Thr Asp
                850                 855                 860

Glu Glu Leu Ala Asp Trp Lys Arg Arg Gln Gln Ile Ala Cys Ile Gly
865                 870                 875                 880

Gly Pro Pro Asn Ile Cys Leu Asp Arg Leu Glu Asn Trp Ile Thr Ser
                885                 890                 895

Leu Ala Glu Ser Gln Leu Gln Thr Arg Gln Gln Ile Lys Lys Leu Glu
                900                 905                 910
```

```
Glu Leu Gln Gln Lys Val Ser Tyr Lys Gly Asp Pro Ile Val Gln His
        915                 920                 925

Arg Pro Met Leu Glu Glu Arg Ile Val Glu Leu Phe Arg Asn Leu Met
    930                 935                 940

Lys Ser Ala Phe Val Val Glu Arg Gln Pro Cys Met Pro Met His Pro
945                 950                 955                 960

Asp Arg Pro Leu Val Ile Lys Thr Gly Val Gln Phe Thr Thr Lys Val
            965                 970                 975

Arg Leu Leu Val Lys Phe Pro Glu Leu Asn Tyr Gln Leu Lys Ile Lys
        980                 985                 990

Val Cys Ile Asp Lys Asp Ser Gly Asp Val Ala Ala Leu Arg Gly Ser
        995                 1000                1005

Arg Lys Phe Asn Ile Leu Gly Thr Asn Thr Lys Val Met Asn Met
    1010                1015                1020

Glu Glu Ser Asn Asn Gly Ser Leu Ser Ala Glu Phe Lys His Leu
    1025                1030                1035

Thr Leu Arg Glu Gln Arg Cys Gly Asn Gly Arg Ala Asn Cys
    1040                1045                1050

Asp Ala Ser Leu Ile Val Thr Glu Glu Leu His Leu Ile Thr Phe
    1055                1060                1065

Glu Thr Glu Val Tyr His Gln Gly Leu Lys Ile Asp Leu Glu Thr
    1070                1075                1080

His Ser Leu Pro Val Val Val Ile Ser Asn Ile Cys Gln Met Pro
    1085                1090                1095

Asn Ala Trp Ala Ser Ile Leu Trp Tyr Asn Met Leu Thr Asn Asn
    1100                1105                1110

Pro Lys Asn Val Asn Phe Phe Thr Lys Pro Pro Ile Gly Thr Trp
    1115                1120                1125

Asp Gln Val Ala Glu Val Leu Ser Trp Gln Phe Ser Ser Thr Thr
    1130                1135                1140

Lys Arg Gly Leu Ser Ile Glu Gln Leu Thr Thr Leu Ala Glu Lys
    1145                1150                1155

Leu Leu Gly Pro Gly Val Asn Tyr Ser Gly Cys Gln Ile Thr Trp
    1160                1165                1170

Ala Lys Phe Cys Lys Glu Asn Met Ala Gly Lys Gly Phe Ser Phe
    1175                1180                1185

Trp Val Trp Leu Asp Asn Ile Ile Asp Leu Val Lys Lys Tyr Ile
    1190                1195                1200

Leu Ala Leu Trp Asn Glu Gly Tyr Ile Met Gly Phe Ile Ser Lys
    1205                1210                1215

Glu Arg Glu Arg Ala Ile Leu Ser Thr Lys Pro Pro Gly Thr Phe
    1220                1225                1230

Leu Leu Arg Phe Ser Glu Ser Ser Lys Glu Gly Gly Val Thr Phe
    1235                1240                1245

Thr Trp Val Glu Lys Asp Ile Ser Gly Lys Thr Gln Ile Gln Ser
    1250                1255                1260

Val Glu Pro Tyr Thr Lys Gln Gln Leu Asn Asn Met Ser Phe Ala
    1265                1270                1275

Glu Ile Ile Met Gly Tyr Lys Ile Met Asp Ala Thr Asn Ile Leu
    1280                1285                1290

Val Ser Pro Leu Val Tyr Leu Tyr Pro Asp Ile Pro Lys Glu Glu
    1295                1300                1305
```

```
Ala Phe Gly Lys Tyr Cys Arg Pro Glu Ser Gln Glu His Pro Glu
1310                1315                1320

Ala Asp Pro Gly Ser Ala Ala Pro Tyr Leu Lys Thr Lys Phe Ile
1325                1330                1335

Cys Val Thr Pro Thr Thr Cys Ser Asn Thr Ile Asp Leu Pro Met
1340                1345                1350

Ser Pro Arg Thr Leu Asp Ser Leu Met Gln Phe Gly Asn Asn Gly
1355                1360                1365

Glu Gly Ala Glu Pro Ser Ala Gly Gly Gln Phe Glu Ser Leu Thr
1370                1375                1380

Phe Asp Met Glu Leu Thr Ser Glu Cys Ala Thr Ser Pro Met Ser
1385                1390                1395

Gly Gly Gly Gly Ser Gly Gly Gly Gly Ser Gly Gly Gly Gly Ser
1400                1405                1410

Gly Gly Gly Gly Ser Gly Gly Gly Gly Ser Met Ala Gly Trp Ile
1415                1420                1425

Gln Ala Gln Gln Leu Gln Gly Asp Ala Leu Arg Gln Met Gln Val
1430                1435                1440

Leu Tyr Gly Gln His Phe Pro Ile Glu Val Arg His Tyr Leu Ala
1445                1450                1455

Gln Trp Ile Glu Ser Gln Pro Trp Asp Ala Ile Asp Leu Asp Asn
1460                1465                1470

Pro Gln Asp Arg Ala Gln Ala Thr Gln Leu Leu Glu Gly Leu Val
1475                1480                1485

Gln Glu Leu Gln Lys Lys Ala Glu His Gln Val Gly Glu Asp Gly
1490                1495                1500

Phe Leu Leu Lys Ile Lys Leu Gly His Tyr Ala Thr Gln Leu Gln
1505                1510                1515

Lys Thr Tyr Asp Arg Cys Pro Leu Glu Leu Val Arg Cys Ile Arg
1520                1525                1530

His Ile Leu Tyr Asn Glu Gln Arg Leu Val Arg Glu Ala Asn Asn
1535                1540                1545

Cys Ser Ser Pro Ala Gly Ile Leu Val Asp Ala Met Ser Gln Lys
1550                1555                1560

His Leu Gln Ile Asn Gln Thr Phe Glu Glu Leu Arg Leu Val Thr
1565                1570                1575

Gln Asp Thr Glu Asn Glu Leu Lys Lys Leu Gln Gln Thr Gln Glu
1580                1585                1590

Tyr Phe Ile Ile Gln Tyr Gln Glu Ser Leu Arg Ile Gln Ala Gln
1595                1600                1605

Phe Ala Gln Leu Ala Gln Leu Ser Pro Gln Glu Arg Leu Ser Arg
1610                1615                1620

Glu Thr Ala Leu Gln Gln Lys Gln Val Ser Leu Glu Ala Trp Leu
1625                1630                1635

Gln Arg Glu Ala Gln Thr Leu Gln Gln Tyr Arg Val Glu Leu Ala
1640                1645                1650

Glu Lys His Gln Lys Thr Leu Gln Leu Leu Arg Lys Gln Gln Thr
1655                1660                1665

Ile Ile Leu Asp Asp Glu Leu Ile Gln Trp Lys Arg Arg Gln Gln
1670                1675                1680

Leu Ala Gly Asn Gly Gly Pro Pro Glu Gly Ser Leu Asp Val Leu
1685                1690                1695

Gln Ser Trp Cys Glu Lys Leu Ala Glu Ile Ile Trp Gln Asn Arg
```

-continued

```
                1700                1705                1710

Gln Gln Ile Arg Arg Ala Glu His Leu Cys Gln Gln Leu Pro Ile
    1715                1720                1725

Pro Gly Pro Val Glu Glu Met Leu Ala Glu Val Asn Ala Thr Ile
    1730                1735                1740

Thr Asp Ile Ile Ser Ala Leu Val Thr Ser Thr Phe Ile Ile Glu
    1745                1750                1755

Lys Gln Pro Pro Gln Val Leu Lys Thr Gln Thr Lys Phe Ala Ala
    1760                1765                1770

Thr Val Arg Leu Leu Val Gly Gly Lys Leu Asn Val His Met Asn
    1775                1780                1785

Pro Pro Gln Val Lys Ala Thr Ile Ile Ser Glu Gln Gln Ala Lys
    1790                1795                1800

Ser Leu Leu Lys Asn Glu Asn Thr Arg Asn Glu Cys Ser Gly Glu
    1805                1810                1815

Ile Leu Asn Asn Cys Cys Val Met Glu Tyr His Gln Ala Thr Gly
    1820                1825                1830

Thr Leu Ser Ala His Phe Arg Asn Met Ser Leu Lys Arg Ile Lys
    1835                1840                1845

Arg Ala Asp Arg Arg Gly Ala Glu Ser Val Thr Glu Glu Lys Phe
    1850                1855                1860

Thr Val Leu Phe Glu Ser Gln Phe Ser Val Gly Ser Asn Glu Leu
    1865                1870                1875

Val Phe Gln Val Lys Thr Leu Ser Leu Pro Val Val Val Ile Val
    1880                1885                1890

His Gly Ser Gln Asp His Asn Ala Thr Ala Thr Val Leu Trp Asp
    1895                1900                1905

Asn Ala Phe Ala Glu Pro Gly Arg Val Pro Phe Ala Val Pro Asp
    1910                1915                1920

Lys Val Leu Trp Pro Gln Leu Cys Glu Ala Leu Asn Met Lys Phe
    1925                1930                1935

Lys Ala Glu Val Gln Ser Asn Arg Gly Leu Thr Lys Glu Asn Leu
    1940                1945                1950

Val Phe Leu Ala Gln Lys Leu Phe Asn Asn Ser Ser Ser His Leu
    1955                1960                1965

Glu Asp Tyr Ser Gly Leu Ser Val Ser Trp Ser Gln Phe Asn Arg
    1970                1975                1980

Glu Asn Leu Pro Gly Trp Asn Tyr Thr Phe Trp Gln Trp Phe Asp
    1985                1990                1995

Gly Val Met Glu Val Leu Lys Lys His His Lys Pro His Trp Asn
    2000                2005                2010

Asp Gly Ala Ile Leu Gly Phe Val Asn Lys Gln Gln Ala His Asp
    2015                2020                2025

Leu Leu Ile Asn Lys Pro Asp Gly Thr Phe Leu Leu Arg Phe Ser
    2030                2035                2040

Asp Ser Glu Ile Gly Gly Ile Thr Ile Ala Trp Lys Phe Asp Ser
    2045                2050                2055

Pro Glu Arg Asn Leu Trp Asn Leu Lys Pro Phe Thr Thr Arg Asp
    2060                2065                2070

Phe Ser Ile Arg Ser Leu Ala Asp Arg Leu Gly Asp Leu Ser Tyr
    2075                2080                2085

Leu Ile Tyr Val Phe Pro Asp Arg Pro Lys Asp Glu Val Phe Ser
    2090                2095                2100
```

```
Lys Tyr Tyr Thr Pro Val Leu Ala Lys Ala Val Asp Gly Tyr Val
2105                2110                2115

Lys Pro Gln Ile Lys Gln Val Val Pro Glu Phe Val Asn Ala Ser
2120                2125                2130

Ala Asp Ala Gly Gly Ser Ser Ala Thr Tyr Met Asp Gln Ala Pro
2135                2140                2145

Ser Pro Ala Val Cys Pro Gln Ala Pro Tyr Asn Met Tyr Pro Gln
2150                2155                2160

Asn Pro Asp His Val Leu Asp Gln Asp Gly Glu Phe Asp Leu Asp
2165                2170                2175

Glu Thr Met Asp Val Ala Arg His Val Glu Glu Leu Leu Arg Arg
2180                2185                2190

Pro Met Asp Ser Leu Asp Ser Arg Leu Ser Pro Pro Ala Gly Leu
2195                2200                2205

Phe Thr Ser Ala Arg Gly Ser Leu Ser Glu Gly Arg Gly Ser Leu
2210                2215                2220

Leu Thr Cys Gly Asp Val Glu Glu Asn Pro Gly Pro Met Glu Thr
2225                2230                2235

Asp Thr Leu Leu Leu Trp Val Leu Leu Leu Trp Val Pro Gly Ser
2240                2245                2250

Thr Gly Asp Ile Gln Met Thr Gln Thr Thr Ser Ser Leu Ser Ala
2255                2260                2265

Ser Leu Gly Asp Arg Val Thr Ile Ser Cys Arg Ala Ser Gln Asp
2270                2275                2280

Ile Ser Lys Tyr Leu Asn Trp Tyr Gln Gln Lys Pro Asp Gly Thr
2285                2290                2295

Val Lys Leu Leu Ile Tyr His Thr Ser Arg Leu His Ser Gly Val
2300                2305                2310

Pro Ser Arg Phe Ser Gly Ser Gly Ser Gly Thr Asp Tyr Ser Leu
2315                2320                2325

Thr Ile Ser Asn Leu Glu Gln Glu Asp Ile Ala Thr Tyr Phe Cys
2330                2335                2340

Gln Gln Gly Asn Thr Leu Pro Tyr Thr Phe Gly Gly Gly Thr Lys
2345                2350                2355

Leu Glu Ile Thr Lys Ala Gly Gly Gly Ser Gly Gly Gly Gly
2360                2365                2370

Ser Gly Gly Gly Gly Ser Gly Gly Gly Ser Glu Val Lys Leu
2375                2380                2385

Gln Glu Ser Gly Pro Gly Leu Val Ala Pro Ser Gln Ser Leu Ser
2390                2395                2400

Val Thr Cys Thr Val Ser Gly Val Ser Leu Pro Asp Tyr Gly Val
2405                2410                2415

Ser Trp Ile Arg Gln Pro Pro Arg Lys Gly Leu Glu Trp Leu Gly
2420                2425                2430

Val Ile Trp Gly Ser Glu Thr Thr Tyr Tyr Asn Ser Ala Leu Lys
2435                2440                2445

Ser Arg Leu Thr Ile Ile Lys Asp Asn Ser Lys Ser Gln Val Phe
2450                2455                2460

Leu Lys Met Asn Ser Leu Gln Thr Asp Asp Thr Ala Ile Tyr Tyr
2465                2470                2475

Cys Ala Lys His Tyr Tyr Tyr Gly Gly Ser Tyr Ala Met Asp Tyr
2480                2485                2490
```

```
Trp Gly Gln Gly Thr Ser Val Thr Val Ser Ser Asp Pro Thr Thr
    2495                2500                2505

Thr Pro Ala Pro Arg Pro Pro Thr Pro Ala Pro Thr Ile Ala Ser
    2510                2515                2520

Gln Pro Leu Ser Leu Arg Pro Glu Ala Cys Arg Pro Ala Ala Gly
    2525                2530                2535

Gly Ala Val His Thr Arg Gly Leu Asp Phe Ala Cys Asp Ile Tyr
    2540                2545                2550

Ile Trp Ala Pro Leu Ala Gly Thr Cys Gly Val Leu Leu Leu Ser
    2555                2560                2565

Leu Val Ile Thr Leu Tyr Cys Lys Arg Gly Arg Lys Lys Leu Leu
    2570                2575                2580

Tyr Ile Phe Lys Gln Pro Phe Met Arg Pro Val Gln Thr Thr Gln
    2585                2590                2595

Glu Glu Asp Gly Cys Ser Cys Arg Phe Pro Glu Glu Glu Glu Gly
    2600                2605                2610

Gly Cys Glu Leu Arg Val Lys Phe Ser Arg Ser Ala Asp Ala Pro
    2615                2620                2625

Ala Tyr Gln Gln Gly Gln Asn Gln Leu Tyr Asn Glu Leu Asn Leu
    2630                2635                2640

Gly Arg Arg Glu Glu Tyr Asp Val Leu Asp Lys Arg Arg Gly Arg
    2645                2650                2655

Asp Pro Glu Met Gly Gly Lys Pro Arg Arg Lys Asn Pro Gln Glu
    2660                2665                2670

Gly Leu Tyr Asn Glu Leu Gln Lys Asp Lys Met Ala Glu Ala Tyr
    2675                2680                2685

Ser Glu Ile Gly Met Lys Gly Glu Arg Arg Arg Gly Lys Gly His
    2690                2695                2700

Asp Gly Leu Tyr Gln Gly Leu Ser Thr Ala Thr Lys Asp Thr Tyr
    2705                2710                2715

Asp Ala Leu His Met Gln Ala Leu Pro Pro Arg
    2720                2725

<210> SEQ ID NO 10
<211> LENGTH: 2430
<212> TYPE: PRT
<213> ORGANISM: Artificial Sequence
<220> FEATURE:
<223> OTHER INFORMATION: constitutively active STAT construct (TIP -
      Linker - dZap70SH2 - linker - TEV - 2a - Truncated CD22 - CD19TM -
      Tyro-1 endodomain - Linker - TetRB - 2A - aCD19 - linker - TEV
      cleavage site x 3 - GOFSTAT5(S710F)

<400> SEQUENCE: 10

Met Trp Thr Trp Asn Ala Tyr Ala Phe Ala Ala Pro Ser Gly Gly Gly
1               5                   10                  15

Ser Met Pro Asp Pro Ala Ala His Leu Pro Phe Phe Tyr Gly Ser Ile
                20                  25                  30

Ser Arg Ala Glu Ala Glu Glu His Leu Lys Leu Ala Gly Met Ala Asp
        35                  40                  45

Gly Leu Phe Leu Leu Arg Gln Cys Leu Arg Ser Leu Gly Gly Tyr Val
    50                  55                  60

Leu Ser Leu Val His Asp Val Arg Phe His His Phe Pro Ile Glu Arg
65                  70                  75                  80

Gln Leu Asn Gly Thr Tyr Ala Ile Ala Gly Gly Lys Ala His Cys Gly
                85                  90                  95
```

```
Pro Ala Glu Leu Cys Glu Phe Tyr Ser Arg Asp Pro Asp Gly Leu Pro
                100                 105                 110

Cys Asn Leu Arg Lys Pro Cys Asn Arg Pro Ser Gly Leu Glu Pro Gln
        115                 120                 125

Pro Gly Val Phe Asp Cys Leu Arg Asp Ala Met Val Arg Asp Tyr Val
    130                 135                 140

Arg Gln Thr Trp Lys Leu Glu Gly Glu Ala Leu Glu Gln Ala Ile Ile
145                 150                 155                 160

Ser Gln Ala Pro Gln Val Glu Lys Leu Ile Ala Thr Ala His Glu
                165                 170                 175

Arg Met Pro Trp Tyr His Ser Ser Leu Thr Arg Glu Glu Ala Glu Arg
            180                 185                 190

Lys Leu Tyr Ser Gly Ala Gln Thr Asp Gly Lys Phe Leu Leu Arg Pro
        195                 200                 205

Arg Lys Glu Gln Gly Thr Tyr Ala Leu Ser Leu Ile Tyr Gly Lys Thr
    210                 215                 220

Val Tyr His Tyr Leu Ile Ser Gln Asp Lys Ala Gly Lys Tyr Cys Ile
225                 230                 235                 240

Pro Glu Gly Thr Lys Phe Asp Thr Leu Trp Gln Leu Val Glu Tyr Leu
                245                 250                 255

Lys Leu Lys Ala Asp Gly Leu Ile Tyr Cys Leu Lys Glu Ala Cys Pro
            260                 265                 270

Asn Ser Ser Ala Ser Asn Ala Ser Gly Ala Ala Ala Pro Thr Leu Pro
        275                 280                 285

Ala His Pro Ser Thr Leu Thr His Pro Ser Gly Gly Gly Gly Ser Ser
    290                 295                 300

Leu Phe Lys Gly Pro Arg Asp Tyr Asn Pro Ile Ser Ser Thr Ile Cys
305                 310                 315                 320

His Leu Thr Asn Glu Ser Asp Gly His Thr Thr Ser Leu Tyr Gly Ile
                325                 330                 335

Gly Phe Gly Pro Phe Ile Ile Thr Asn Lys His Leu Phe Arg Arg Asn
            340                 345                 350

Asn Gly Thr Leu Leu Val Gln Ser Leu His Gly Val Phe Lys Val Lys
        355                 360                 365

Asn Thr Thr Thr Leu Gln Gln His Leu Ile Asp Gly Arg Asp Met Ile
    370                 375                 380

Ile Ile Arg Met Pro Lys Asp Phe Pro Pro Phe Pro Gln Lys Leu Lys
385                 390                 395                 400

Phe Arg Glu Pro Gln Arg Glu Glu Arg Ile Cys Leu Val Thr Thr Asn
                405                 410                 415

Phe Gln Thr Lys Ser Met Ser Ser Met Val Ser Asp Thr Ser Cys Thr
            420                 425                 430

Phe Pro Ser Ser Asp Gly Ile Phe Trp Lys His Trp Ile Gln Thr Lys
        435                 440                 445

Asp Gly Gln Cys Gly Ser Pro Leu Val Ser Thr Arg Asp Gly Phe Ile
    450                 455                 460

Val Gly Ile His Ser Ala Ser Asn Phe Thr Asn Thr Asn Asn Tyr Phe
465                 470                 475                 480

Thr Ser Val Pro Lys Asn Phe Met Glu Leu Leu Thr Asn Gln Glu Ala
                485                 490                 495

Gln Gln Trp Val Ser Gly Trp Arg Leu Asn Ala Asp Ser Val Leu Trp
            500                 505                 510

Gly Gly His Lys Val Phe Met Ser Lys Pro Glu Glu Pro Phe Gln Pro
```

```
                515                 520                 525
Val Lys Glu Ala Thr Gln Leu Met Asn Glu Leu Val Tyr Ser Gln Glu
        530                 535                 540

Gly Arg Gly Ser Leu Leu Thr Cys Gly Asp Val Glu Asn Pro Gly
545                 550                 555                 560

Pro Met Glu Thr Asp Thr Leu Leu Leu Trp Val Leu Leu Trp Val
                        565                 570                 575

Pro Gly Ser Thr Gly Asp Ser Ser Gly Lys Pro Ile Pro Asn Pro Leu
                580                 585                 590

Leu Gly Leu Asp Ser Ser Gly Gly Ser Ala Pro Arg Asp Val Arg
        595                 600                 605

Val Arg Lys Ile Lys Pro Leu Ser Glu Ile His Ser Gly Asn Ser Val
        610                 615                 620

Ser Leu Gln Cys Asp Phe Ser Ser His Pro Lys Glu Val Gln Phe
625                 630                 635                 640

Phe Trp Glu Lys Asn Gly Arg Leu Leu Gly Lys Glu Ser Gln Leu Asn
                    645                 650                 655

Phe Asp Ser Ile Ser Pro Glu Asp Ala Gly Ser Tyr Ser Cys Trp Val
                660                 665                 670

Asn Asn Ser Ile Gly Gln Thr Ala Ser Lys Ala Trp Thr Leu Glu Val
        675                 680                 685

Leu Tyr Ala Pro Arg Arg Leu Arg Val Ser Met Ser Pro Gly Asp Gln
        690                 695                 700

Val Met Glu Gly Lys Ser Ala Thr Leu Thr Cys Glu Ser Asp Ala Asn
705                 710                 715                 720

Pro Pro Val Ser His Tyr Thr Trp Phe Asp Trp Asn Asn Gln Ser Leu
                    725                 730                 735

Pro Tyr His Ser Gln Lys Leu Arg Leu Glu Pro Val Lys Val Gln His
                740                 745                 750

Ser Gly Ala Tyr Trp Cys Gln Gly Thr Asn Ser Val Gly Lys Gly Arg
        755                 760                 765

Ser Pro Leu Ser Thr Leu Thr Val Tyr Tyr Ser Pro Glu Thr Ile Gly
        770                 775                 780

Arg Arg Ala Val Thr Leu Ala Tyr Leu Ile Phe Cys Leu Cys Ser Leu
785                 790                 795                 800

Val Gly Ile Leu His Leu Arg Ala Arg Arg Ser Met Asp Glu Ala Asn
                    805                 810                 815

Gln Pro Leu Leu Thr Asp Gln Tyr Gln Cys Tyr Ala Glu Glu Tyr Glu
                820                 825                 830

Lys Leu Gln Asn Pro Asn Gln Ser Val Val Gly Gly Ser Gly Gly Ser
        835                 840                 845

Met Ser Arg Leu Asp Lys Ser Lys Val Ile Asn Ser Ala Leu Glu Leu
        850                 855                 860

Leu Asn Glu Val Gly Ile Glu Gly Leu Thr Thr Arg Lys Leu Ala Gln
865                 870                 875                 880

Lys Leu Gly Val Glu Gln Pro Thr Leu Tyr Trp His Val Lys Asn Lys
                    885                 890                 895

Arg Ala Leu Leu Asp Ala Leu Ala Ile Glu Met Leu Asp Arg His His
                900                 905                 910

Thr His Phe Cys Pro Leu Glu Gly Glu Ser Trp Gln Asp Phe Leu Arg
        915                 920                 925

Asn Asn Ala Lys Ser Phe Arg Cys Ala Leu Leu Ser His Arg Asp Gly
        930                 935                 940
```

```
Ala Lys Val His Leu Gly Thr Arg Pro Thr Glu Lys Gln Tyr Glu Thr
945                 950                 955                 960

Leu Glu Asn Gln Leu Ala Phe Leu Cys Gln Gln Gly Phe Ser Leu Glu
                965                 970                 975

Asn Ala Leu Tyr Ala Leu Ser Ala Val Gly His Phe Thr Leu Gly Cys
            980                 985                 990

Val Leu Glu Asp Gln Glu His Gln Val Ala Lys Glu Glu Arg Glu Thr
        995                 1000                1005

Pro Thr Thr Asp Ser Met Pro Pro Leu Leu Arg Gln Ala Ile Glu
1010                1015                1020

Leu Phe Asp His Gln Gly Ala Glu Pro Ala Phe Leu Phe Gly Leu
1025                1030                1035

Glu Leu Ile Ile Cys Gly Leu Glu Lys Gln Leu Lys Cys Glu Ser
1040                1045                1050

Gly Ser Glu Gly Arg Gly Ser Leu Leu Thr Cys Gly Asp Val Glu
1055                1060                1065

Glu Asn Pro Gly Pro Met Glu Thr Asp Thr Leu Leu Leu Trp Val
1070                1075                1080

Leu Leu Leu Trp Val Pro Gly Ser Thr Gly Asp Ile Gln Met Thr
1085                1090                1095

Gln Thr Thr Ser Ser Leu Ser Ala Ser Leu Gly Asp Arg Val Thr
1100                1105                1110

Ile Ser Cys Arg Ala Ser Gln Asp Ile Ser Lys Tyr Leu Asn Trp
1115                1120                1125

Tyr Gln Gln Lys Pro Asp Gly Thr Val Lys Leu Leu Ile Tyr His
1130                1135                1140

Thr Ser Arg Leu His Ser Gly Val Pro Ser Arg Phe Ser Gly Ser
1145                1150                1155

Gly Ser Gly Thr Asp Tyr Ser Leu Thr Ile Ser Asn Leu Glu Gln
1160                1165                1170

Glu Asp Ile Ala Thr Tyr Phe Cys Gln Gln Gly Asn Thr Leu Pro
1175                1180                1185

Tyr Thr Phe Gly Gly Gly Thr Lys Leu Glu Ile Thr Lys Ala Gly
1190                1195                1200

Gly Gly Gly Ser Gly Gly Gly Gly Ser Gly Gly Gly Gly Ser Gly
1205                1210                1215

Gly Gly Gly Ser Glu Val Lys Leu Gln Glu Ser Gly Pro Gly Leu
1220                1225                1230

Val Ala Pro Ser Gln Ser Leu Ser Val Thr Cys Thr Val Ser Gly
1235                1240                1245

Val Ser Leu Pro Asp Tyr Gly Val Ser Trp Ile Arg Gln Pro Pro
1250                1255                1260

Arg Lys Gly Leu Glu Trp Leu Gly Val Ile Trp Gly Ser Glu Thr
1265                1270                1275

Thr Tyr Tyr Asn Ser Ala Leu Lys Ser Arg Leu Thr Ile Ile Lys
1280                1285                1290

Asp Asn Ser Lys Ser Gln Val Phe Leu Lys Met Asn Ser Leu Gln
1295                1300                1305

Thr Asp Asp Thr Ala Ile Tyr Tyr Cys Ala Lys His Tyr Tyr Tyr
1310                1315                1320

Gly Gly Ser Tyr Ala Met Asp Tyr Trp Gly Gln Gly Thr Ser Val
1325                1330                1335
```

-continued

Thr Val Ser Ser Asp Pro Thr Thr Pro Ala Pro Arg Pro Pro
1340                    1345            1350

Thr Pro Ala Pro Thr Ile Ala Ser Gln Pro Leu Ser Leu Arg Pro
1355                1360            1365

Glu Ala Cys Arg Pro Ala Ala Gly Gly Ala Val His Thr Arg Gly
1370            1375                1380

Leu Asp Phe Ala Cys Asp Ile Tyr Ile Trp Ala Pro Leu Ala Gly
1385            1390                1395

Thr Cys Gly Val Leu Leu Leu Ser Leu Val Ile Thr Leu Tyr Cys
1400                1405                1410

Lys Arg Gly Arg Lys Lys Leu Leu Tyr Ile Phe Lys Gln Pro Phe
1415                1420                1425

Met Arg Pro Val Gln Thr Thr Gln Glu Glu Asp Gly Cys Ser Cys
1430                1435                1440

Arg Phe Pro Glu Glu Glu Glu Gly Gly Cys Glu Leu Arg Val Lys
1445                1450                1455

Phe Ser Arg Ser Ala Asp Ala Pro Ala Tyr Gln Gln Gly Gln Asn
1460                1465                1470

Gln Leu Tyr Asn Glu Leu Asn Leu Gly Arg Arg Glu Glu Tyr Asp
1475                1480                1485

Val Leu Asp Lys Arg Arg Gly Arg Asp Pro Glu Met Gly Gly Lys
1490                1495                1500

Pro Arg Arg Lys Asn Pro Gln Glu Gly Leu Tyr Asn Glu Leu Gln
1505                1510                1515

Lys Asp Lys Met Ala Glu Ala Tyr Ser Glu Ile Gly Met Lys Gly
1520                1525                1530

Glu Arg Arg Arg Gly Lys Gly His Asp Gly Leu Tyr Gln Gly Leu
1535                1540                1545

Ser Thr Ala Thr Lys Asp Thr Tyr Asp Ala Leu His Met Gln Ala
1550                1555                1560

Leu Pro Pro Arg Gly Gly Ser Gly Gly Ser Glu Asn Leu Tyr Phe
1565                1570                1575

Gln Gly Glu Asn Leu Tyr Phe Gln Gly Glu Asn Leu Tyr Phe Gln
1580                1585                1590

Gly Glu Asn Leu Tyr Phe Gln Gly Glu Asn Leu Tyr Phe Gln Gly
1595                1600                1605

Glu Asn Leu Tyr Phe Gln Gly Glu Asn Leu Tyr Phe Gln Gly Glu
1610                1615                1620

Asn Leu Tyr Phe Gln Gly Glu Asn Leu Tyr Phe Gln Gly Met Ala
1625                1630                1635

Gly Trp Ile Gln Ala Gln Gln Leu Gln Gly Asp Ala Leu Arg Gln
1640                1645                1650

Met Gln Val Leu Tyr Gly Gln His Phe Pro Ile Glu Val Arg His
1655                1660                1665

Tyr Leu Ala Gln Trp Ile Glu Ser Gln Pro Trp Asp Ala Ile Asp
1670                1675                1680

Leu Asp Asn Pro Gln Asp Arg Ala Gln Ala Thr Gln Leu Leu Glu
1685                1690                1695

Gly Leu Val Gln Glu Leu Gln Lys Lys Ala Glu His Gln Val Gly
1700                1705                1710

Glu Asp Gly Phe Leu Leu Lys Ile Lys Leu Gly His Tyr Ala Thr
1715                1720                1725

Gln Leu Gln Lys Thr Tyr Asp Arg Cys Pro Leu Glu Leu Val Arg

```
              1730                1735                1740
Cys Ile Arg His Ile Leu Tyr Asn Glu Gln Arg Leu Val Arg Glu
              1745                1750                1755

Ala Asn Asn Cys Ser Ser Pro Ala Gly Ile Leu Val Asp Ala Met
              1760                1765                1770

Ser Gln Lys His Leu Gln Ile Asn Gln Thr Phe Glu Glu Leu Arg
              1775                1780                1785

Leu Val Thr Gln Asp Thr Glu Asn Glu Leu Lys Lys Leu Gln Gln
              1790                1795                1800

Thr Gln Glu Tyr Phe Ile Ile Gln Tyr Gln Glu Ser Leu Arg Ile
              1805                1810                1815

Gln Ala Gln Phe Ala Gln Leu Ala Gln Leu Ser Pro Gln Glu Arg
              1820                1825                1830

Leu Ser Arg Glu Thr Ala Leu Gln Gln Lys Gln Val Ser Leu Glu
              1835                1840                1845

Ala Trp Leu Gln Arg Glu Ala Gln Thr Leu Gln Gln Tyr Arg Val
              1850                1855                1860

Glu Leu Ala Glu Lys His Gln Lys Thr Leu Gln Leu Leu Arg Lys
              1865                1870                1875

Gln Gln Thr Ile Ile Leu Asp Asp Glu Leu Ile Gln Trp Lys Arg
              1880                1885                1890

Arg Gln Gln Leu Ala Gly Asn Gly Gly Pro Pro Glu Gly Ser Leu
              1895                1900                1905

Asp Val Leu Gln Ser Trp Cys Glu Lys Leu Ala Glu Ile Ile Trp
              1910                1915                1920

Gln Asn Arg Gln Gln Ile Arg Arg Ala Glu His Leu Cys Gln Gln
              1925                1930                1935

Leu Pro Ile Pro Gly Pro Val Glu Glu Met Leu Ala Glu Val Asn
              1940                1945                1950

Ala Thr Ile Thr Asp Ile Ile Ser Ala Leu Val Thr Ser Thr Phe
              1955                1960                1965

Ile Ile Glu Lys Gln Pro Pro Gln Val Leu Lys Thr Gln Thr Lys
              1970                1975                1980

Phe Ala Ala Thr Val Arg Leu Leu Val Gly Gly Lys Leu Asn Val
              1985                1990                1995

His Met Asn Pro Pro Gln Val Lys Ala Thr Ile Ile Ser Glu Gln
              2000                2005                2010

Gln Ala Lys Ser Leu Leu Lys Asn Glu Asn Thr Arg Asn Glu Cys
              2015                2020                2025

Ser Gly Glu Ile Leu Asn Asn Cys Cys Val Met Glu Tyr His Gln
              2030                2035                2040

Ala Thr Gly Thr Leu Ser Ala His Phe Arg Asn Met Ser Leu Lys
              2045                2050                2055

Arg Ile Lys Arg Ala Asp Arg Arg Gly Ala Glu Ser Val Thr Glu
              2060                2065                2070

Glu Lys Phe Thr Val Leu Phe Glu Ser Gln Phe Ser Val Gly Ser
              2075                2080                2085

Asn Glu Leu Val Phe Gln Val Lys Thr Leu Ser Leu Pro Val Val
              2090                2095                2100

Val Ile Val His Gly Ser Gln Asp His Asn Ala Thr Ala Thr Val
              2105                2110                2115

Leu Trp Asp Asn Ala Phe Ala Glu Pro Gly Arg Val Pro Phe Ala
              2120                2125                2130
```

Val Pro Asp Lys Val Leu Trp Pro Gln Leu Cys Glu Ala Leu Asn
                2135                2140                2145

Met Lys Phe Lys Ala Glu Val Gln Ser Asn Arg Gly Leu Thr Lys
                2150                2155                2160

Glu Asn Leu Val Phe Leu Ala Gln Lys Leu Phe Asn Asn Ser Ser
                2165                2170                2175

Ser His Leu Glu Asp Tyr Ser Gly Leu Ser Val Ser Trp Ser Gln
                2180                2185                2190

Phe Asn Arg Glu Asn Leu Pro Gly Trp Asn Tyr Thr Phe Trp Gln
                2195                2200                2205

Trp Phe Asp Gly Val Met Glu Val Leu Lys Lys His His Lys Pro
                2210                2215                2220

His Trp Asn Asp Gly Ala Ile Leu Gly Phe Val Asn Lys Gln Gln
                2225                2230                2235

Ala His Asp Leu Leu Ile Asn Lys Pro Asp Gly Thr Phe Leu Leu
                2240                2245                2250

Arg Phe Ser Asp Ser Glu Ile Gly Gly Ile Thr Ile Ala Trp Lys
                2255                2260                2265

Phe Asp Ser Pro Glu Arg Asn Leu Trp Asn Leu Lys Pro Phe Thr
                2270                2275                2280

Thr Arg Asp Phe Ser Ile Arg Ser Leu Ala Asp Arg Leu Gly Asp
                2285                2290                2295

Leu Ser Tyr Leu Ile Tyr Val Phe Pro Asp Arg Pro Lys Asp Glu
                2300                2305                2310

Val Phe Ser Lys Tyr Tyr Thr Pro Val Leu Ala Lys Ala Val Asp
                2315                2320                2325

Gly Tyr Val Lys Pro Gln Ile Lys Gln Val Val Pro Glu Phe Val
                2330                2335                2340

Asn Ala Phe Ala Asp Ala Gly Gly Ser Ser Ala Thr Tyr Met Asp
                2345                2350                2355

Gln Ala Pro Ser Pro Ala Val Cys Pro Gln Ala Pro Tyr Asn Met
                2360                2365                2370

Tyr Pro Gln Asn Pro Asp His Val Leu Asp Gln Asp Gly Glu Phe
                2375                2380                2385

Asp Leu Asp Glu Thr Met Asp Val Ala Arg His Val Glu Glu Leu
                2390                2395                2400

Leu Arg Arg Pro Met Asp Ser Leu Asp Ser Arg Leu Ser Pro Pro
                2405                2410                2415

Ala Gly Leu Phe Thr Ser Ala Arg Gly Ser Leu Ser
                2420                2425                2430

<210> SEQ ID NO 11
<211> LENGTH: 1813
<212> TYPE: PRT
<213> ORGANISM: Artificial Sequence
<220> FEATURE:
<223> OTHER INFORMATION: constitutively active STAT construct (FRB -
      linker - STAT5 - 2a - FKBP12 - linker - STAT3)

<400> SEQUENCE: 11

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr

```
                35                  40                  45
Ser Phe Asn Gln Ala Tyr Gly Arg Asp Leu Met Glu Ala Gln Glu Trp
 50                  55                  60
Cys Arg Lys Tyr Met Lys Ser Gly Asn Val Lys Asp Leu Leu Gln Ala
 65                  70                  75                  80
Trp Asp Leu Tyr Tyr His Val Phe Arg Arg Ile Ser Lys Ser Gly Gly
                     85                  90                  95
Gly Gly Ser Gly Gly Gly Gly Ser Gly Gly Gly Gly Ser Met Ala Gly
                100                 105                 110
Trp Ile Gln Ala Gln Gln Leu Gln Gly Asp Ala Leu Arg Gln Met Gln
                115                 120                 125
Val Leu Tyr Gly Gln His Phe Pro Ile Glu Val Arg His Tyr Leu Ala
                130                 135                 140
Gln Trp Ile Glu Ser Gln Pro Trp Asp Ala Ile Asp Leu Asp Asn Pro
145                 150                 155                 160
Gln Asp Arg Ala Gln Ala Thr Gln Leu Leu Glu Gly Leu Val Gln Glu
                165                 170                 175
Leu Gln Lys Lys Ala Glu His Gln Val Gly Glu Asp Gly Phe Leu Leu
                180                 185                 190
Lys Ile Lys Leu Gly His Tyr Ala Thr Gln Leu Gln Lys Thr Tyr Asp
                195                 200                 205
Arg Cys Pro Leu Glu Leu Val Arg Cys Ile Arg His Ile Leu Tyr Asn
210                 215                 220
Glu Gln Arg Leu Val Arg Glu Ala Asn Asn Cys Ser Ser Pro Ala Gly
225                 230                 235                 240
Ile Leu Val Asp Ala Met Ser Gln Lys His Leu Gln Ile Asn Gln Thr
                245                 250                 255
Phe Glu Glu Leu Arg Leu Val Thr Gln Asp Thr Glu Asn Glu Leu Lys
                260                 265                 270
Lys Leu Gln Gln Thr Gln Glu Tyr Phe Ile Ile Gln Tyr Gln Glu Ser
                275                 280                 285
Leu Arg Ile Gln Ala Gln Phe Ala Gln Leu Ala Gln Leu Ser Pro Gln
                290                 295                 300
Glu Arg Leu Ser Arg Glu Thr Ala Leu Gln Gln Lys Gln Val Ser Leu
305                 310                 315                 320
Glu Ala Trp Leu Gln Arg Glu Ala Gln Thr Leu Gln Gln Tyr Arg Val
                325                 330                 335
Glu Leu Ala Glu Lys His Gln Lys Thr Leu Gln Leu Leu Arg Lys Gln
                340                 345                 350
Gln Thr Ile Ile Leu Asp Asp Glu Leu Ile Gln Trp Lys Arg Arg Gln
                355                 360                 365
Gln Leu Ala Gly Asn Gly Gly Pro Glu Gly Ser Leu Asp Val Leu
                370                 375                 380
Gln Ser Trp Cys Glu Lys Leu Ala Glu Ile Ile Trp Gln Asn Arg Gln
385                 390                 395                 400
Gln Ile Arg Arg Ala Glu His Leu Cys Gln Gln Leu Pro Ile Pro Gly
                405                 410                 415
Pro Val Glu Glu Met Leu Ala Glu Val Asn Ala Thr Ile Thr Asp Ile
                420                 425                 430
Ile Ser Ala Leu Val Thr Ser Thr Phe Ile Ile Glu Lys Gln Pro Pro
                435                 440                 445
Gln Val Leu Lys Thr Gln Thr Lys Phe Ala Ala Thr Val Arg Leu Leu
                450                 455                 460
```

```
Val Gly Gly Lys Leu Asn Val His Met Asn Pro Pro Gln Val Lys Ala
465                 470                 475                 480

Thr Ile Ile Ser Glu Gln Gln Ala Lys Ser Leu Leu Lys Asn Glu Asn
                485                 490                 495

Thr Arg Asn Glu Cys Ser Gly Glu Ile Leu Asn Asn Cys Cys Val Met
            500                 505                 510

Glu Tyr His Gln Ala Thr Gly Thr Leu Ser Ala His Phe Arg Asn Met
            515                 520                 525

Ser Leu Lys Arg Ile Lys Arg Ala Asp Arg Arg Gly Ala Glu Ser Val
            530                 535                 540

Thr Glu Glu Lys Phe Thr Val Leu Phe Glu Ser Gln Phe Ser Val Gly
545                 550                 555                 560

Ser Asn Glu Leu Val Phe Gln Val Lys Thr Leu Ser Leu Pro Val Val
                565                 570                 575

Val Ile Val His Gly Ser Gln Asp His Asn Ala Thr Ala Thr Val Leu
            580                 585                 590

Trp Asp Asn Ala Phe Ala Glu Pro Gly Arg Val Pro Phe Ala Val Pro
            595                 600                 605

Asp Lys Val Leu Trp Pro Gln Leu Cys Glu Ala Leu Asn Met Lys Phe
610                 615                 620

Lys Ala Glu Val Gln Ser Asn Arg Gly Leu Thr Lys Glu Asn Leu Val
625                 630                 635                 640

Phe Leu Ala Gln Lys Leu Phe Asn Asn Ser Ser Ser His Leu Glu Asp
                645                 650                 655

Tyr Ser Gly Leu Ser Val Ser Trp Ser Gln Phe Asn Arg Glu Asn Leu
                660                 665                 670

Pro Gly Trp Asn Tyr Thr Phe Trp Gln Trp Phe Asp Gly Val Met Glu
                675                 680                 685

Val Leu Lys Lys His His Lys Pro His Trp Asn Asp Gly Ala Ile Leu
            690                 695                 700

Gly Phe Val Asn Lys Gln Gln Ala His Asp Leu Leu Ile Asn Lys Pro
705                 710                 715                 720

Asp Gly Thr Phe Leu Leu Arg Phe Ser Asp Ser Glu Ile Gly Gly Ile
                725                 730                 735

Thr Ile Ala Trp Lys Phe Asp Ser Pro Glu Arg Asn Leu Trp Asn Leu
            740                 745                 750

Lys Pro Phe Thr Thr Arg Asp Phe Ser Ile Arg Ser Leu Ala Asp Arg
            755                 760                 765

Leu Gly Asp Leu Ser Tyr Leu Ile Tyr Val Phe Pro Asp Arg Pro Lys
            770                 775                 780

Asp Glu Val Phe Ser Lys Tyr Tyr Thr Pro Val Leu Ala Lys Ala Val
785                 790                 795                 800

Asp Gly Tyr Val Lys Pro Gln Ile Lys Gln Val Val Pro Glu Phe Val
            805                 810                 815

Asn Ala Ser Ala Asp Ala Gly Gly Ser Ser Ala Thr Tyr Met Asp Gln
            820                 825                 830

Ala Pro Ser Pro Ala Val Cys Pro Gln Ala Pro Tyr Asn Met Tyr Pro
            835                 840                 845

Gln Asn Pro Asp His Val Leu Asp Gln Asp Gly Glu Phe Asp Leu Asp
            850                 855                 860

Glu Thr Met Asp Val Ala Arg His Val Glu Glu Leu Leu Arg Arg Pro
865                 870                 875                 880
```

-continued

```
Met Asp Ser Leu Asp Ser Arg Leu Ser Pro Ala Gly Leu Phe Thr
            885                 890                 895

Ser Ala Arg Gly Ser Leu Ser Glu Gly Arg Gly Ser Leu Leu Thr Cys
            900                 905                 910

Gly Asp Val Glu Glu Asn Pro Gly Pro Gly Val Gln Val Glu Thr Ile
            915                 920                 925

Ser Pro Gly Asp Gly Arg Thr Phe Pro Lys Arg Gly Gln Thr Cys Val
            930                 935                 940

Val His Tyr Thr Gly Met Leu Glu Asp Gly Lys Lys Val Asp Ser Ser
945                 950                 955                 960

Arg Asp Arg Asn Lys Pro Phe Lys Phe Met Leu Gly Lys Gln Glu Val
                965                 970                 975

Ile Arg Gly Trp Glu Glu Gly Val Ala Gln Met Ser Val Gly Gln Arg
                980                 985                 990

Ala Lys Leu Thr Ile Ser Pro Asp Tyr Ala Tyr Gly Ala Thr Gly His
            995                 1000                1005

Pro Gly Ile Ile Pro Pro His Ala Thr Leu Val Phe Asp Val Glu
    1010                1015                1020

Leu Leu Lys Leu Glu Ser Gly Gly Gly Ser Gly Gly Gly Gly
    1025                1030                1035

Ser Gly Gly Gly Gly Ser Ala Gln Trp Asn Gln Leu Gln Gln Leu
    1040                1045                1050

Asp Thr Arg Tyr Leu Glu Gln Leu His Gln Leu Tyr Ser Asp Ser
    1055                1060                1065

Phe Pro Met Glu Leu Arg Gln Phe Leu Ala Pro Trp Ile Glu Ser
    1070                1075                1080

Gln Asp Trp Ala Tyr Ala Ala Ser Lys Glu Ser His Ala Thr Leu
    1085                1090                1095

Val Phe His Asn Leu Leu Gly Glu Ile Asp Gln Gln Tyr Ser Arg
    1100                1105                1110

Phe Leu Gln Glu Ser Asn Val Leu Tyr Gln His Asn Leu Arg Arg
    1115                1120                1125

Ile Lys Gln Phe Leu Gln Ser Arg Tyr Leu Glu Lys Pro Met Glu
    1130                1135                1140

Ile Ala Arg Ile Val Ala Arg Cys Leu Trp Glu Glu Ser Arg Leu
    1145                1150                1155

Leu Gln Thr Ala Ala Thr Ala Ala Gln Gln Gly Gly Gln Ala Asn
    1160                1165                1170

His Pro Thr Ala Ala Val Val Thr Glu Lys Gln Gln Met Leu Glu
    1175                1180                1185

Gln His Leu Gln Asp Val Arg Lys Arg Val Gln Asp Leu Glu Gln
    1190                1195                1200

Lys Met Lys Val Val Glu Asn Leu Gln Asp Asp Phe Asp Phe Asn
    1205                1210                1215

Tyr Lys Thr Leu Lys Ser Gln Gly Asp Met Gln Asp Leu Asn Gly
    1220                1225                1230

Asn Asn Gln Ser Val Thr Arg Gln Lys Met Gln Gln Leu Glu Gln
    1235                1240                1245

Met Leu Thr Ala Leu Asp Gln Met Arg Arg Ser Ile Val Ser Glu
    1250                1255                1260

Leu Ala Gly Leu Leu Ser Ala Met Glu Tyr Val Gln Lys Thr Leu
    1265                1270                1275

Thr Asp Glu Glu Leu Ala Asp Trp Lys Arg Arg Gln Gln Ile Ala
```

-continued

```
            1280                1285                1290

Cys Ile Gly Gly Pro Pro Asn Ile Cys Leu Asp Arg Leu Glu Asn
            1295                1300                1305

Trp Ile Thr Ser Leu Ala Glu Ser Gln Leu Gln Thr Arg Gln Gln
            1310                1315                1320

Ile Lys Lys Leu Glu Glu Leu Gln Gln Lys Val Ser Tyr Lys Gly
            1325                1330                1335

Asp Pro Ile Val Gln His Arg Pro Met Leu Glu Glu Arg Ile Val
            1340                1345                1350

Glu Leu Phe Arg Asn Leu Met Lys Ser Ala Phe Val Val Glu Arg
            1355                1360                1365

Gln Pro Cys Met Pro Met His Pro Asp Arg Pro Leu Val Ile Lys
            1370                1375                1380

Thr Gly Val Gln Phe Thr Thr Lys Val Arg Leu Leu Val Lys Phe
            1385                1390                1395

Pro Glu Leu Asn Tyr Gln Leu Lys Ile Lys Val Cys Ile Asp Lys
            1400                1405                1410

Asp Ser Gly Asp Val Ala Ala Leu Arg Gly Ser Arg Lys Phe Asn
            1415                1420                1425

Ile Leu Gly Thr Asn Thr Lys Val Met Asn Met Glu Glu Ser Asn
            1430                1435                1440

Asn Gly Ser Leu Ser Ala Glu Phe Lys His Leu Thr Leu Arg Glu
            1445                1450                1455

Gln Arg Cys Gly Asn Gly Gly Arg Ala Asn Cys Asp Ala Ser Leu
            1460                1465                1470

Ile Val Thr Glu Glu Leu His Leu Ile Thr Phe Glu Thr Glu Val
            1475                1480                1485

Tyr His Gln Gly Leu Lys Ile Asp Leu Glu Thr His Ser Leu Pro
            1490                1495                1500

Val Val Val Ile Ser Asn Ile Cys Gln Met Pro Asn Ala Trp Ala
            1505                1510                1515

Ser Ile Leu Trp Tyr Asn Met Leu Thr Asn Asn Pro Lys Asn Val
            1520                1525                1530

Asn Phe Phe Thr Lys Pro Pro Ile Gly Thr Trp Asp Gln Val Ala
            1535                1540                1545

Glu Val Leu Ser Trp Gln Phe Ser Ser Thr Thr Lys Arg Gly Leu
            1550                1555                1560

Ser Ile Glu Gln Leu Thr Thr Leu Ala Glu Lys Leu Leu Gly Pro
            1565                1570                1575

Gly Val Asn Tyr Ser Gly Cys Gln Ile Thr Trp Ala Lys Phe Cys
            1580                1585                1590

Lys Glu Asn Met Ala Gly Lys Gly Phe Ser Phe Trp Val Trp Leu
            1595                1600                1605

Asp Asn Ile Ile Asp Leu Val Lys Lys Tyr Ile Leu Ala Leu Trp
            1610                1615                1620

Asn Glu Gly Tyr Ile Met Gly Phe Ile Ser Lys Glu Arg Glu Arg
            1625                1630                1635

Ala Ile Leu Ser Thr Lys Pro Pro Gly Thr Phe Leu Leu Arg Phe
            1640                1645                1650

Ser Glu Ser Ser Lys Glu Gly Gly Val Thr Phe Thr Trp Val Glu
            1655                1660                1665

Lys Asp Ile Ser Gly Lys Thr Gln Ile Gln Ser Val Glu Pro Tyr
            1670                1675                1680
```

```
Thr Lys Gln Gln Leu Asn Asn Met Ser Phe Ala Glu Ile Ile Met
    1685                1690                1695

Gly Tyr Lys Ile Met Asp Ala Thr Asn Ile Leu Val Ser Pro Leu
    1700                1705                1710

Val Tyr Leu Tyr Pro Asp Ile Pro Lys Glu Glu Ala Phe Gly Lys
    1715                1720                1725

Tyr Cys Arg Pro Glu Ser Gln Glu His Pro Glu Ala Asp Pro Gly
    1730                1735                1740

Ser Ala Ala Pro Tyr Leu Lys Thr Lys Phe Ile Cys Val Thr Pro
    1745                1750                1755

Thr Thr Cys Ser Asn Thr Ile Asp Leu Pro Met Ser Pro Arg Thr
    1760                1765                1770

Leu Asp Ser Leu Met Gln Phe Gly Asn Asn Gly Glu Gly Ala Glu
    1775                1780                1785

Pro Ser Ala Gly Gly Gln Phe Glu Ser Leu Thr Phe Asp Met Glu
    1790                1795                1800

Leu Thr Ser Glu Cys Ala Thr Ser Pro Met
    1805                1810

<210> SEQ ID NO 12
<211> LENGTH: 1832
<212> TYPE: PRT
<213> ORGANISM: Artificial Sequence
<220> FEATURE:
<223> OTHER INFORMATION: constitutively active STAT construct (TIP -
      linker - STAT5 - 2a - TetRB - linker - STAT3)

<400> SEQUENCE: 12

Met Trp Thr Trp Asn Ala Tyr Ala Phe Ala Ala Pro Ser Gly Gly
1               5                   10                  15

Gly Ser Gly Gly Gly Ser Gly Gly Gly Ser Met Ala Gly Trp
                20                  25                  30

Ile Gln Ala Gln Gln Leu Gln Gly Asp Ala Leu Arg Gln Met Gln Val
                35                  40                  45

Leu Tyr Gly Gln His Phe Pro Ile Glu Val Arg His Tyr Leu Ala Gln
    50                  55                  60

Trp Ile Glu Ser Gln Pro Trp Asp Ala Ile Asp Leu Asp Asn Pro Gln
65                  70                  75                  80

Asp Arg Ala Gln Ala Thr Gln Leu Leu Glu Gly Leu Val Gln Glu Leu
                85                  90                  95

Gln Lys Lys Ala Glu His Gln Val Gly Glu Asp Gly Phe Leu Leu Lys
                100                 105                 110

Ile Lys Leu Gly His Tyr Ala Thr Gln Leu Gln Lys Thr Tyr Asp Arg
            115                 120                 125

Cys Pro Leu Glu Leu Val Arg Cys Ile Arg His Ile Leu Tyr Asn Glu
    130                 135                 140

Gln Arg Leu Val Arg Glu Ala Asn Asn Cys Ser Ser Pro Ala Gly Ile
145                 150                 155                 160

Leu Val Asp Ala Met Ser Gln Lys His Leu Gln Ile Asn Gln Thr Phe
                165                 170                 175

Glu Glu Leu Arg Leu Val Thr Gln Asp Thr Glu Asn Glu Leu Lys Lys
                180                 185                 190

Leu Gln Gln Thr Gln Glu Tyr Phe Ile Ile Gln Tyr Gln Glu Ser Leu
            195                 200                 205

Arg Ile Gln Ala Gln Phe Ala Gln Leu Ala Gln Leu Ser Pro Gln Glu
```

-continued

```
            210                 215                 220
Arg Leu Ser Arg Glu Thr Ala Leu Gln Gln Lys Gln Val Ser Leu Glu
225                 230                 235                 240

Ala Trp Leu Gln Arg Glu Ala Gln Thr Leu Gln Gln Tyr Arg Val Glu
                245                 250                 255

Leu Ala Glu Lys His Gln Lys Thr Leu Gln Leu Leu Arg Lys Gln Gln
                260                 265                 270

Thr Ile Ile Leu Asp Asp Glu Leu Ile Gln Trp Lys Arg Arg Gln Gln
            275                 280                 285

Leu Ala Gly Asn Gly Gly Pro Pro Glu Gly Ser Leu Asp Val Leu Gln
            290                 295                 300

Ser Trp Cys Glu Lys Leu Ala Glu Ile Ile Trp Gln Asn Arg Gln Gln
305                 310                 315                 320

Ile Arg Arg Ala Glu His Leu Cys Gln Gln Leu Pro Ile Pro Gly Pro
                325                 330                 335

Val Glu Glu Met Leu Ala Glu Val Asn Ala Thr Ile Thr Asp Ile Ile
                340                 345                 350

Ser Ala Leu Val Thr Ser Thr Phe Ile Ile Glu Lys Gln Pro Pro Gln
            355                 360                 365

Val Leu Lys Thr Gln Thr Lys Phe Ala Ala Thr Val Arg Leu Leu Val
            370                 375                 380

Gly Gly Lys Leu Asn Val His Met Asn Pro Pro Gln Val Lys Ala Thr
385                 390                 395                 400

Ile Ile Ser Glu Gln Gln Ala Lys Ser Leu Leu Lys Asn Glu Asn Thr
                405                 410                 415

Arg Asn Glu Cys Ser Gly Glu Ile Leu Asn Asn Cys Cys Val Met Glu
                420                 425                 430

Tyr His Gln Ala Thr Gly Thr Leu Ser Ala His Phe Arg Asn Met Ser
            435                 440                 445

Leu Lys Arg Ile Lys Arg Ala Asp Arg Arg Gly Ala Glu Ser Val Thr
            450                 455                 460

Glu Glu Lys Phe Thr Val Leu Phe Glu Ser Gln Phe Ser Val Gly Ser
465                 470                 475                 480

Asn Glu Leu Val Phe Gln Val Lys Thr Leu Ser Leu Pro Val Val Val
                485                 490                 495

Ile Val His Gly Ser Gln Asp His Asn Ala Thr Ala Thr Val Leu Trp
                500                 505                 510

Asp Asn Ala Phe Ala Glu Pro Gly Arg Val Pro Phe Ala Val Pro Asp
            515                 520                 525

Lys Val Leu Trp Pro Gln Leu Cys Glu Ala Leu Asn Met Lys Phe Lys
            530                 535                 540

Ala Glu Val Gln Ser Asn Arg Gly Leu Thr Lys Glu Asn Leu Val Phe
545                 550                 555                 560

Leu Ala Gln Lys Leu Phe Asn Asn Ser Ser Ser His Leu Glu Asp Tyr
                565                 570                 575

Ser Gly Leu Ser Val Ser Trp Ser Gln Phe Asn Arg Glu Asn Leu Pro
            580                 585                 590

Gly Trp Asn Tyr Thr Phe Trp Gln Trp Phe Asp Gly Val Met Glu Val
            595                 600                 605

Leu Lys Lys His His Lys Pro His Trp Asn Asp Gly Ala Ile Leu Gly
            610                 615                 620

Phe Val Asn Lys Gln Gln Ala His Asp Leu Leu Ile Asn Lys Pro Asp
625                 630                 635                 640
```

```
Gly Thr Phe Leu Leu Arg Phe Ser Asp Ser Glu Ile Gly Ile Thr
                645                 650                 655

Ile Ala Trp Lys Phe Asp Ser Pro Glu Arg Asn Leu Trp Asn Leu Lys
                660                 665                 670

Pro Phe Thr Thr Arg Asp Phe Ser Ile Arg Ser Leu Ala Asp Arg Leu
                675                 680                 685

Gly Asp Leu Ser Tyr Leu Ile Tyr Val Phe Pro Asp Arg Pro Lys Asp
                690                 695                 700

Glu Val Phe Ser Lys Tyr Tyr Thr Pro Val Leu Ala Lys Ala Val Asp
705                 710                 715                 720

Gly Tyr Val Lys Pro Gln Ile Lys Gln Val Val Pro Glu Phe Val Asn
                725                 730                 735

Ala Ser Ala Asp Ala Gly Gly Ser Ser Ala Thr Tyr Met Asp Gln Ala
                740                 745                 750

Pro Ser Pro Ala Val Cys Pro Gln Ala Pro Tyr Asn Met Tyr Pro Gln
                755                 760                 765

Asn Pro Asp His Val Leu Asp Gln Asp Gly Glu Phe Asp Leu Asp Glu
                770                 775                 780

Thr Met Asp Val Ala Arg His Val Glu Glu Leu Leu Arg Arg Pro Met
785                 790                 795                 800

Asp Ser Leu Asp Ser Arg Leu Ser Pro Pro Ala Gly Leu Phe Thr Ser
                805                 810                 815

Ala Arg Gly Ser Leu Ser Glu Gly Arg Gly Ser Leu Leu Thr Cys Gly
                820                 825                 830

Asp Val Glu Glu Asn Pro Gly Pro Met Ser Arg Leu Asp Lys Ser Lys
                835                 840                 845

Val Ile Asn Ser Ala Leu Glu Leu Leu Asn Glu Val Gly Ile Glu Gly
                850                 855                 860

Leu Thr Thr Arg Lys Leu Ala Gln Lys Leu Gly Val Glu Gln Pro Thr
865                 870                 875                 880

Leu Tyr Trp His Val Lys Asn Lys Arg Ala Leu Leu Asp Ala Leu Ala
                885                 890                 895

Ile Glu Met Leu Asp Arg His His Thr His Phe Cys Pro Leu Glu Gly
                900                 905                 910

Glu Ser Trp Gln Asp Phe Leu Arg Asn Asn Ala Lys Ser Phe Arg Cys
                915                 920                 925

Ala Leu Leu Ser His Arg Asp Gly Ala Lys Val His Leu Gly Thr Arg
                930                 935                 940

Pro Thr Glu Lys Gln Tyr Glu Thr Leu Glu Asn Gln Leu Ala Phe Leu
945                 950                 955                 960

Cys Gln Gln Gly Phe Ser Leu Glu Asn Ala Leu Tyr Ala Leu Ser Ala
                965                 970                 975

Val Gly His Phe Thr Leu Gly Cys Val Leu Glu Asp Gln Glu His Gln
                980                 985                 990

Val Ala Lys Glu Glu Arg Glu Thr Pro Thr Thr Asp Ser Met Pro Pro
                995                 1000                1005

Leu Leu Arg Gln Ala Ile Glu Leu Phe Asp His Gln Gly Ala Glu
        1010                1015                1020

Pro Ala Phe Leu Phe Gly Leu Glu Leu Ile Ile Cys Gly Leu Glu
        1025                1030                1035

Lys Gln Leu Lys Cys Glu Ser Gly Ser Gly Gly Gly Gly Ser
        1040                1045                1050
```

```
Gly Gly Gly Gly Ser Gly Gly Gly Gly Ser Ala Gln Trp Asn Gln
        1055                1060                1065

Leu Gln Gln Leu Asp Thr Arg Tyr Leu Glu Gln Leu His Gln Leu
        1070                1075                1080

Tyr Ser Asp Ser Phe Pro Met Glu Leu Arg Gln Phe Leu Ala Pro
        1085                1090                1095

Trp Ile Glu Ser Gln Asp Trp Ala Tyr Ala Ala Ser Lys Glu Ser
        1100                1105                1110

His Ala Thr Leu Val Phe His Asn Leu Leu Gly Glu Ile Asp Gln
        1115                1120                1125

Gln Tyr Ser Arg Phe Leu Gln Glu Ser Asn Val Leu Tyr Gln His
        1130                1135                1140

Asn Leu Arg Arg Ile Lys Gln Phe Leu Gln Ser Arg Tyr Leu Glu
        1145                1150                1155

Lys Pro Met Glu Ile Ala Arg Ile Val Ala Arg Cys Leu Trp Glu
        1160                1165                1170

Glu Ser Arg Leu Leu Gln Thr Ala Ala Thr Ala Ala Gln Gln Gly
        1175                1180                1185

Gly Gln Ala Asn His Pro Thr Ala Ala Val Val Thr Glu Lys Gln
        1190                1195                1200

Gln Met Leu Glu Gln His Leu Gln Asp Val Arg Lys Arg Val Gln
        1205                1210                1215

Asp Leu Glu Gln Lys Met Lys Val Val Glu Asn Leu Gln Asp Asp
        1220                1225                1230

Phe Asp Phe Asn Tyr Lys Thr Leu Lys Ser Gln Gly Asp Met Gln
        1235                1240                1245

Asp Leu Asn Gly Asn Asn Gln Ser Val Thr Arg Gln Lys Met Gln
        1250                1255                1260

Gln Leu Glu Gln Met Leu Thr Ala Leu Asp Gln Met Arg Arg Ser
        1265                1270                1275

Ile Val Ser Glu Leu Ala Gly Leu Leu Ser Ala Met Glu Tyr Val
        1280                1285                1290

Gln Lys Thr Leu Thr Asp Glu Glu Leu Ala Asp Trp Lys Arg Arg
        1295                1300                1305

Gln Gln Ile Ala Cys Ile Gly Gly Pro Pro Asn Ile Cys Leu Asp
        1310                1315                1320

Arg Leu Glu Asn Trp Ile Thr Ser Leu Ala Glu Ser Gln Leu Gln
        1325                1330                1335

Thr Arg Gln Gln Ile Lys Lys Leu Glu Glu Leu Gln Gln Lys Val
        1340                1345                1350

Ser Tyr Lys Gly Asp Pro Ile Val Gln His Arg Pro Met Leu Glu
        1355                1360                1365

Glu Arg Ile Val Glu Leu Phe Arg Asn Leu Met Lys Ser Ala Phe
        1370                1375                1380

Val Val Glu Arg Gln Pro Cys Met Pro Met His Pro Asp Arg Pro
        1385                1390                1395

Leu Val Ile Lys Thr Gly Val Gln Phe Thr Thr Lys Val Arg Leu
        1400                1405                1410

Leu Val Lys Phe Pro Glu Leu Asn Tyr Gln Leu Lys Ile Lys Val
        1415                1420                1425

Cys Ile Asp Lys Asp Ser Gly Asp Val Ala Ala Leu Arg Gly Ser
        1430                1435                1440

Arg Lys Phe Asn Ile Leu Gly Thr Asn Thr Lys Val Met Asn Met
```

```
            1445                1450                1455

Glu Glu Ser Asn Asn Gly Ser Leu Ser Ala Glu Phe Lys His Leu
        1460                1465                1470

Thr Leu Arg Glu Gln Arg Cys Gly Asn Gly Arg Ala Asn Cys
    1475                1480                1485

Asp Ala Ser Leu Ile Val Thr Glu Glu Leu His Leu Ile Thr Phe
        1490                1495                1500

Glu Thr Glu Val Tyr His Gln Gly Leu Lys Ile Asp Leu Glu Thr
        1505                1510                1515

His Ser Leu Pro Val Val Ile Ser Asn Ile Cys Gln Met Pro
    1520                1525                1530

Asn Ala Trp Ala Ser Ile Leu Trp Tyr Asn Met Leu Thr Asn Asn
        1535                1540                1545

Pro Lys Asn Val Asn Phe Phe Thr Lys Pro Pro Ile Gly Thr Trp
        1550                1555                1560

Asp Gln Val Ala Glu Val Leu Ser Trp Gln Phe Ser Ser Thr Thr
        1565                1570                1575

Lys Arg Gly Leu Ser Ile Glu Gln Leu Thr Thr Leu Ala Glu Lys
        1580                1585                1590

Leu Leu Gly Pro Gly Val Asn Tyr Ser Gly Cys Gln Ile Thr Trp
        1595                1600                1605

Ala Lys Phe Cys Lys Glu Asn Met Ala Gly Lys Gly Phe Ser Phe
        1610                1615                1620

Trp Val Trp Leu Asp Asn Ile Ile Asp Leu Val Lys Lys Tyr Ile
        1625                1630                1635

Leu Ala Leu Trp Asn Glu Gly Tyr Ile Met Gly Phe Ile Ser Lys
        1640                1645                1650

Glu Arg Glu Arg Ala Ile Leu Ser Thr Lys Pro Pro Gly Thr Phe
        1655                1660                1665

Leu Leu Arg Phe Ser Glu Ser Ser Lys Glu Gly Gly Val Thr Phe
        1670                1675                1680

Thr Trp Val Glu Lys Asp Ile Ser Gly Lys Thr Gln Ile Gln Ser
        1685                1690                1695

Val Glu Pro Tyr Thr Lys Gln Gln Leu Asn Asn Met Ser Phe Ala
        1700                1705                1710

Glu Ile Ile Met Gly Tyr Lys Ile Met Asp Ala Thr Asn Ile Leu
        1715                1720                1725

Val Ser Pro Leu Val Tyr Leu Tyr Pro Asp Ile Pro Lys Glu Glu
        1730                1735                1740

Ala Phe Gly Lys Tyr Cys Arg Pro Glu Ser Gln Glu His Pro Glu
        1745                1750                1755

Ala Asp Pro Gly Ser Ala Ala Pro Tyr Leu Lys Thr Lys Phe Ile
        1760                1765                1770

Cys Val Thr Pro Thr Thr Cys Ser Asn Thr Ile Asp Leu Pro Met
        1775                1780                1785

Ser Pro Arg Thr Leu Asp Ser Leu Met Gln Phe Gly Asn Asn Gly
        1790                1795                1800

Glu Gly Ala Glu Pro Ser Ala Gly Gly Gln Phe Glu Ser Leu Thr
        1805                1810                1815

Phe Asp Met Glu Leu Thr Ser Glu Cys Ala Thr Ser Pro Met
        1820                1825                1830

<210> SEQ ID NO 13
```

```
<211> LENGTH: 4
<212> TYPE: PRT
<213> ORGANISM: Artificial Sequence
<220> FEATURE:
<223> OTHER INFORMATION: basic amino acid furin target sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa may be Arg or Lys

<400> SEQUENCE: 13

Arg Xaa Xaa Arg
1

<210> SEQ ID NO 14
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 14

Glu Asn Leu Tyr Phe Gln Ser
1               5
```